US012419656B2

(12) United States Patent
Mantri

(10) Patent No.: US 12,419,656 B2
(45) Date of Patent: Sep. 23, 2025

(54) SYSTEMS AND METHODS FOR REMOVAL OF BIOLOGICAL OBJECTS FROM ANATOMICAL STRUCTURES WITHIN A BODY

(71) Applicant: Ventaris Surgical, Inc., San Carlos, CA (US)

(72) Inventor: Surag Mantri, East Palo Alto, CA (US)

(73) Assignee: Ventaris Surgical, Inc., San Carlos, CA (US)

( * ) Notice: Subject to any disclaimer, the term of this patent is extended or adjusted under 35 U.S.C. 154(b) by 0 days.

(21) Appl. No.: 18/933,999

(22) Filed: Oct. 31, 2024

(65) Prior Publication Data

US 2025/0134593 A1    May 1, 2025

Related U.S. Application Data

(60) Provisional application No. 63/595,291, filed on Nov. 1, 2023, provisional application No. 63/595,272, filed on Nov. 1, 2023.

(51) Int. Cl.
*A61B 17/22* (2006.01)
*A61B 18/00* (2006.01)
(Continued)

(52) U.S. Cl.
CPC ............ *A61B 17/22* (2013.01); *A61B 18/245* (2013.01); *A61B 90/06* (2016.02);
(Continued)

(58) Field of Classification Search
CPC .. A61B 18/245; A61B 90/06; A61B 2090/064
See application file for complete search history.

(56) References Cited

U.S. PATENT DOCUMENTS 5,176,675 A    1/1993  Watson
5,320,599 A *  6/1994  Griep ................ A61M 25/0068
                                                 604/35
(Continued)

FOREIGN PATENT DOCUMENTS

CN        115243623      10/2022
WO    WO 2003/045259 A1   6/2003

OTHER PUBLICATIONS

De Coninck et al., "Ureteral Access Sheaths and Its Use in the Future: A Comprehensive Update Based on a Literature Review," J Clin Med. Aug. 31, 2022; 11(17):5128. doi: 10.3390/jcm11175128.
(Continued)

*Primary Examiner* — Benjamin J Klein
*Assistant Examiner* — Thien Jason Tran
(74) *Attorney, Agent, or Firm* — Knobbe, Martens, Olson & Bear, LLP

(57) ABSTRACT

Implementations of the present disclosure generally relate to medical aspiration devices and their methods of use. In some cases, the devices are configured to create a vacuum to capture and/or immobilize a solid deposit at a location internal to a subject. Such configurations may be useful, for example, for removing intact kidney stones small enough to pass through the ureter. In some cases, the devices further include an ablation instrument. Such devices may be useful, for example, for ablating larger solid deposits into a plurality of smaller particles at a location internal to the subject (e.g., ablating kidney stones that are too large to pass through the ureter). In some cases, the vacuum created by the devices is used to remove the plurality of smaller particles from the location internal to the subject.

27 Claims, 30 Drawing Sheets

(51) Int. Cl.
A61B 18/24 (2006.01)
A61B 90/00 (2016.01)
A61B 17/00 (2006.01)

(52) U.S. Cl.
CPC .............. *A61B 2017/00084* (2013.01); *A61B 2017/22079* (2013.01); *A61B 2018/00505* (2013.01); *A61B 2018/00577* (2013.01); *A61B 2018/00642* (2013.01); *A61B 2018/00672* (2013.01); *A61B 2018/00791* (2013.01); *A61B 2090/064* (2016.02); *A61B 2218/002* (2013.01); *A61B 2218/007* (2013.01)

(56) References Cited

U.S. PATENT DOCUMENTS

| | | | |
|---|---|---|---|
| 5,453,088 | A | 9/1995 | Boudewijn et al. |
| 5,496,267 | A | 3/1996 | Drasler et al. |
| 5,947,988 | A * | 9/1999 | Smith ............... A61B 17/3203 606/167 |
| 6,135,977 | A | 10/2000 | Drasler |
| 10,406,276 | B2 | 9/2019 | Eisner et al. |
| 11,116,530 | B2 * | 9/2021 | Yurek ............... A61M 25/005 |
| 11,324,526 | B2 | 5/2022 | Yurek |
| 11,382,693 | B2 * | 7/2022 | Harrah ............... A61B 1/126 |
| 12,023,059 | B2 | 7/2024 | Yurek |
| 12,256,989 | B2 | 3/2025 | Yurek |
| 12,318,099 | B2 | 6/2025 | Yurek |
| 12,329,396 | B2 | 6/2025 | Tong et al. |
| 12,329,399 | B2 | 6/2025 | Tong et al. |
| 2001/0051811 | A1 | 12/2001 | Bonnette |
| 2003/0178030 | A1 | 9/2003 | Constantz |
| 2007/0244353 | A1 | 10/2007 | Larsen |
| 2012/0089047 | A1 | 4/2012 | Ryba et al. |
| 2013/0066166 | A1 | 3/2013 | Burnett et al. |
| 2020/0085378 | A1 | 3/2020 | Burnett et al. |
| 2022/0218367 | A1 | 7/2022 | Ghani et al. |
| 2023/0248434 | A1 | 8/2023 | Altshuler et al. |
| 2025/0082348 | A1 | 3/2025 | Pereira et al. |
| 2025/0134538 | A1 | 5/2025 | Mantri |

OTHER PUBLICATIONS

Geavlete et al., "Retrograde Intrarenal Surgery for Lithiasis Using Suctioning Devices: A Shift in Paradigm?," J Clin Med. Apr. 24, 2024;13(9):2493. doi: 10.3390/jcm13092493.

Lua et al., "Optimal deflection techniques for flexible and navigable suction ureteral access sheaths (FANS): a comparative in vitro PEARLS analysis," World J Urol. Oct. 30, 2024;42(1):606. doi: 10.1007/s00345-024-05297-3.

Madden et al., "Direct In-scope Suction: An In Vitro Evaluation Of A Single-use Flexible Ureteroscope With Integrated Suction Capability," Journal of Urology, Sep. 1, 2024; 211(5S):e984. doi.org/10.1007/s00345-024-05203-x.

Solano et al., "Optimizing Outcomes in Flexible Ureteroscopy: A Narrative Review of Suction Techniques," J Clin Med. Apr. 11, 2023;12(8):2815. doi: 10.3390/jcm12082815.

Stern et al., "Steerable Ureteroscopic Renal Evacuation (SURE) for Large Renal Stones: A Multi-Institutional Center Study," J Endourol. Nov. 2023;37(11):1179-83. doi: 10.1089/end.2023.0424.

Sur et al., "Initial Safety and Feasibility of Steerable Ureteroscopic Renal Evacuation: A Novel Approach for the Treatment of Urolithiasis," J Endourol. Sep. 2022;36(9):1161-1167. doi: 10.1089/end.2021.0759.

Yuen et al., "Scoping Review of Experimental and Clinical Evidence and Its Influence on Development of the Suction Ureteral Access Sheath," Diagnostics (Basel). May 16, 2024;14(10):1034. doi: 10.3390/diagnostics14101034.

International Search Report and Written Opinion Received in International Application No. PCT/US2024/053980, mailed Feb. 14, 2025, 9 pages.

\* cited by examiner

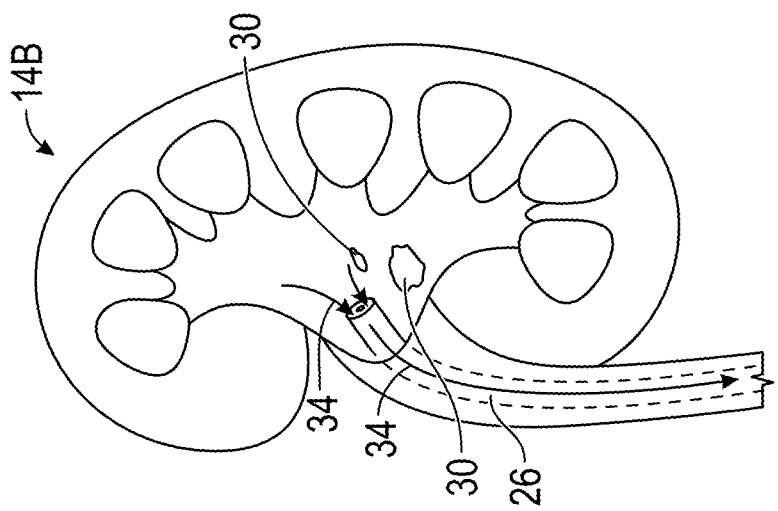
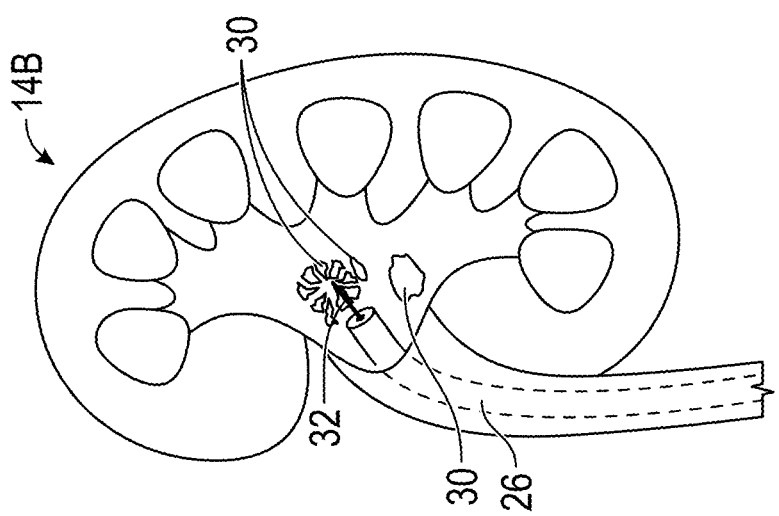
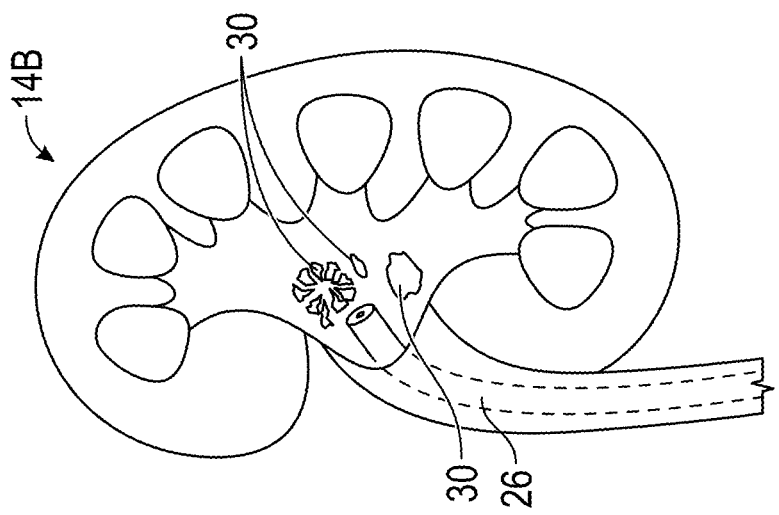

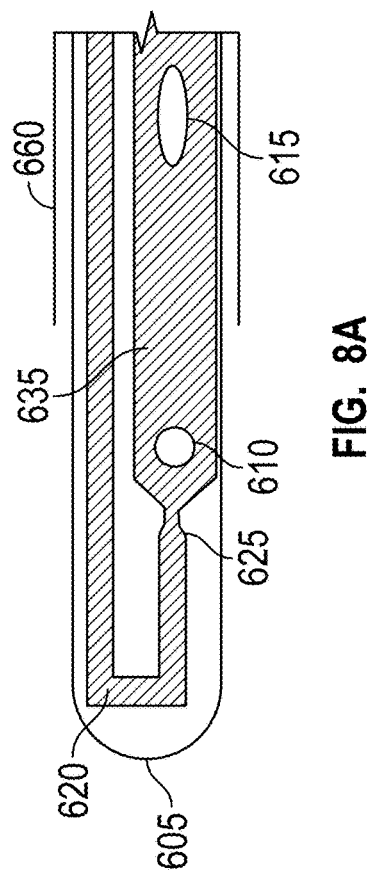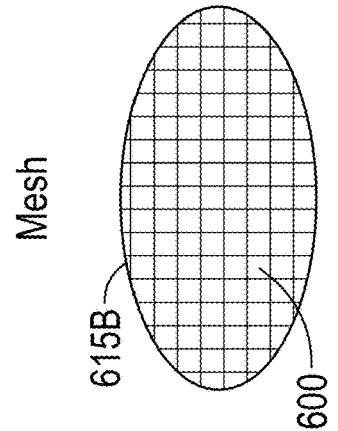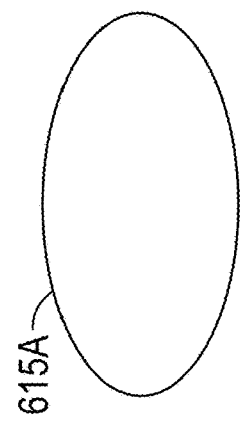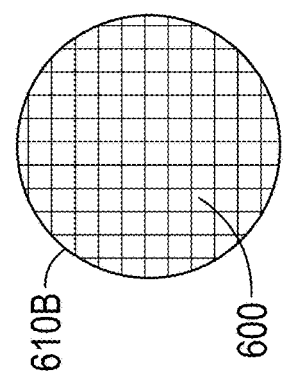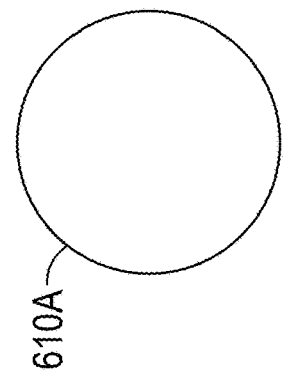

SYSTEMS AND METHODS FOR REMOVAL OF BIOLOGICAL OBJECTS FROM ANATOMICAL STRUCTURES WITHIN A BODY

INCORPORATION BY REFERENCE TO ANY PRIORITY APPLICATIONS

This application claims priority to U.S. Provisional Patent Application Nos. 63/595,272 and 63/595,291, filed on Nov. 1, 2023, the disclosure of each of which is incorporated by reference in its entirety.

TECHNICAL FIELD

The present disclosure generally relates to medical systems and related methods, such as minimally invasive surgical devices and systems for manipulating and removing biological objects from an anatomical structure.

DESCRIPTION OF THE RELATED ART

Minimally invasive surgeries offer numerous advantages over traditional open surgical techniques. These encompass reduced surgical trauma, decreased recovery time, shorter hospital stays, and/or potentially a diminished risk of infection and other complications. However, certain challenges persist in minimally invasive surgery, notably the requirement for precise manipulation and removal of objects within the body while preventing damage to the adjacent tissues. This precision is of paramount importance in fluid-filled environments and/or intact organs, such as the kidney, gall bladder, urinary bladder, urinary tract, blood vessels, or other body cavities or organs.

For kidney stone treatment, the two primary approaches include ureteroscopic lithotripsy and percutaneous nephrolithotomy (PCNL), which incorporates its variant, the mini-PCNL. Both procedures, whether utilizing a ureteroscope or a nephroscope, generally encounter parallel challenges, including extended operation times, an obscured visual field, difficulties in extracting residual fragments, stone retropulsion, high intra-luminal pressure, challenges with temperature regulation, and/or instrument size that limit ureteral access. Accordingly, improved systems and methods are needed for safe and effective removal of biological objects.

SUMMARY

Described herein are systems, devices and methods for removal of a biological object from an anatomical structure. Certain systems, devices and methods may be applied to removing a biological object such as a kidney stone from a urinary tract. Certain systems and methods described herein can use a Venturi-effect to attract the biological object towards the one or more openings.

A system for use in a removal procedure of a biological object from a urinary tract can include: a catheter body including a proximal end and a distal end configured to be inserted into the urinary tract, the catheter body including one or more openings configured to receive at least a portion of the biological object; an evacuation lumen positioned at least partially within the catheter body, wherein the evacuation lumen is in fluid communication with the one or more openings; and a supply lumen positioned at least partially within the catheter body and configured to transport a liquid from a liquid source to the distal end of the catheter body, the supply lumen configured to eject the liquid as a liquid jet outside the supply lumen and create a vacuum at the one or more openings via a Venturi effect; wherein the vacuum created via the Venturi effect is configured to attract the biological object toward the one or more openings and the system is configured to remove a plurality of fragments of the biological object from the urinary tract through the evacuation lumen toward the proximal end of the catheter body with a regulated fluid flow.

A system for use in a removal procedure of a biological object from a urinary tract can include: a catheter body including a proximal end and a distal end configured to be inserted into the urinary tract, the catheter body including one or more openings configured to receive at least a portion of the biological object; an evacuation lumen positioned at least partially within the catheter body, the evacuation lumen in fluid communication with the one or more openings, the evacuation lumen configured to be in fluid communication with a vacuum source, the vacuum source configured to supply vacuum at a first vacuum level to facilitate aspiration of a plurality of fragments of the biological object and transportation of the plurality of fragments of the biological object from the one or more openings toward the proximal end of the catheter body; and a supply lumen positioned at least partially within the catheter body and configured to transport a liquid from a liquid source to the distal end of the catheter body, the supply lumen configured to eject the liquid as a liquid jet outside the supply lumen and create a vacuum at the one or more openings at a second vacuum level via a Venturi effect to attract the biological object toward the one or more openings.

A system for use in a removal procedure of a biological object from a urinary tract can include: a catheter body including a proximal end and a distal end configured to be inserted into the urinary tract, the catheter body including an opening at a tip of the distal end of the catheter body configured to receive at least a portion of the biological object; a supply lumen positioned at least partially within the catheter body and configured to transport a liquid from the proximal end toward the distal end of the catheter body, eject the liquid, and cause a vacuum to be created at the opening to aspirate a plurality of fragments of the biological object; and an evacuation lumen positioned at least partially within the catheter body in fluid communication with the opening, wherein the evacuation lumen is configured to transport the plurality of fragments of the biological object from the distal end toward the proximal end of the catheter body, wherein the catheter body is configured to receive an ablation device configured to fragment the biological object into the plurality of fragments, and wherein the supply lumen is configured to direct liquid to flow toward the distal end of the catheter body and be redirected at the distal end to flow toward the proximal end of the catheter body.

A system for use in a removal procedure of a biological object from a urinary tract can include: a catheter body including a proximal end and a distal end configured to be inserted into the urinary tract, the catheter body including one or more openings configured to receive the biological object; an evacuation lumen positioned at least partially within the catheter body in fluid communication with the one or more openings, wherein the evacuation lumen is configured to aspirate a plurality of fragments of the biological object and transport the plurality of fragments of the biological object from the one or more openings toward the proximal end of the catheter body; a supply lumen positioned at least partially within the catheter body and configured to transport a liquid to the distal end of the catheter body, the supply lumen including a first portion that directs a flow of the liquid from the proximal end of the catheter body toward the distal end of the catheter body and a second portion that redirects the flow of the liquid toward the proximal end of the catheter body, wherein the second portion is configured to eject the liquid outside the supply lumen and create vacuum at the one or more openings via a Venturi effect to facilitate attracting the biological object at the one or more openings; and a plurality of vents formed in the catheter body and fluidically connected to the evacuation lumen, the plurality of vents configured to resupply into the urinary tract at least some of the liquid ejected from the supply lumen and aspirated by the evacuation lumen.

In some implementations, a plurality of vent port openings can be formed in the catheter body and fluidically connected to the evacuation lumen, the plurality of vent port openings can be configured to resupply into the urinary tract at least some of the liquid ejected from the supply lumen to maintain a fluid balance and pressure balance in the urinary tract.

In some implementations, the supply lumen can include a first portion that directs a flow of the liquid from the proximal end of the catheter body toward the distal end of the catheter body and a second portion that redirects the flow of the liquid toward the proximal end of the catheter body.

In some implementations, a controller can be configured to regulate a flow rate of the liquid by the supply lumen to maintain a temperature in the urinary tract at or below a temperature threshold indicative of safe operating temperature.

In some implementations, a temperature sensor can be configured to monitor a temperature, and the controller can be configured to regulate the flow rate of the liquid in the supply lumen based on the temperature.

In some implementations, the catheter body can be configured to receive an ablation device configured to fragment the biological object into a plurality of fragments.

In some implementations, a vacuum source can be in fluid communication with the evacuation lumen to regulate fluid flow through the evacuation lumen.

In some implementations, liquid-jet powered aspiration and/or Venturi-assisted medical instruments are provided. In some instances, a medical instrument includes an evacuation tube including at least one aspiration port opening formed in a side wall of the evacuation tube and at least one vent port opening positioned downstream of the at least one aspiration port opening, when the instrument is in operation, wherein the at least one aspiration port opening is positioned downstream relative to an outlet when the instrument is in operation, and wherein a first vent port opening is positioned on a different side of the evacuation tube relative to a second vent port opening, when the instrument is in operation, a liquid supply lumen including a nozzle suitable for forming a liquid jet at an outlet of the liquid supply lumen, the outlet configured and positioned to direct the liquid jet formed by the nozzle into and along an evacuation lumen of the evacuation tube, wherein the at least one aspiration port opening is positioned downstream relative to the outlet when the instrument is in operation, and wherein, upon exiting the nozzle, the liquid flows past at least a portion of the at least one aspiration port opening, generating a vacuum at the at least one aspiration port opening relative to an environment external to the evacuation lumen, when the instrument is in operation.

In some implementations, a medical instrument includes an evacuation tube including at least one aspiration port opening formed in a side wall of the evacuation tube and at least one vent port opening positioned downstream of the at least one aspiration port opening, when the instrument is in operation, a liquid supply lumen including a nozzle suitable for forming a liquid jet at an outlet of the liquid supply lumen, the outlet configured and positioned to direct the liquid jet formed by the nozzle into and along an evacuation lumen of the evacuation tube, a liquid source in fluidic communication with the liquid supply lumen configured to supply pressurized liquid to the liquid supply lumen, such that, when the liquid flows through the nozzle and past the at least one aspiration port, a vacuum is generated at the aspiration port, relative to an environment external to the evacuation lumen, sufficient to aspirate at least a portion of a surrounding liquid from the location internal to the subject, and a controller configured to operate or regulate operation of the liquid source such that the at least one vent port opening ejects at least a portion of the liquid supplied by the liquid source from the lumen of the evacuation tube into the location internal to the subject, said portion being less than a volume of the liquid aspirated into the evacuation lumen when the system is in operation.

In some implementations, a medical instrument includes an evacuation tube including at least one aspiration port opening formed in a side wall of the evacuation tube and at least one vent port opening positioned downstream of the at least one aspiration port opening, when the instrument is in operation, a liquid supply lumen including a nozzle suitable for forming a liquid jet at an outlet of the liquid supply lumen, the outlet configured and positioned to direct the liquid jet formed by the nozzle into and along an evacuation lumen of the evacuation tube, a liquid source in fluidic communication with the liquid supply lumen configured to supply pressurized liquid to the liquid supply lumen, such that, when the pressurized liquid flows through the nozzle and past the at least one aspiration port, a vacuum is generated at the aspiration port, relative to an environment external to the evacuation lumen, sufficient to aspirate at least a portion of the surrounding liquid from the location internal to the subject, and a controller configured to operate or regulate operation of the liquid source such that a pressure and/or a volume of the surrounding liquid during operation of the instrument system is within less than or equal to 50% of an initial pressure and/or an initial volume of the surrounding liquid prior to operation of the instrument.

In some implementations, a medical instrument includes a liquid supply lumen configured to receive and transport a pressurized liquid to a nozzle positioned at an end of the liquid supply lumen when connected to a source of the liquid, an evacuation tube providing an evacuation lumen and includes at least one aspiration port in the form of one or more openings in a side wall of the evacuation tube configured so that liquid ejected from the nozzle is directed past the aspiration port to generate a Venturi-created or Venturi-assisted vacuum for capturing a biological object at the location internal to the subject, when the instrument is in operation.

In some implementations, a medical instrument includes a liquid-jet forming aspiration catheter including an evacuation tube including at least one aspiration port opening formed in a side wall of the evacuation tube, a liquid supply lumen including a nozzle suitable for forming the liquid jet at an outlet of the liquid supply lumen, the outlet configured and positioned to direct the liquid jet formed by the nozzle into and along an evacuation lumen of the evacuation tube, wherein the at least one aspiration port opening is positioned downstream relative to the nozzle when the instrument is in operation such that a liquid, upon exiting the nozzle, flows past at least a portion of the at least one aspiration opening generating a vacuum at the at least one aspiration opening relative to an environment external to the evacuation lumen when the instrument is in operation, and an outer sheath in which the liquid-jet forming aspiration catheter is disposed, wherein the liquid-jet forming aspiration catheter is axially and rotationally movable within the sheath to enable adjustment of an angular orientation of a distal end of the liquid-jet forming aspiration catheter and exposure of the at least one aspiration port to the environment external to the evacuation lumen when the instrument is in operation.

In some implementations, a medical aspiration-ablation system includes a liquid-jet powered aspiration instrument including a nozzle configured and positioned to direct a liquid jet into an evacuation lumen of the instrument to create a vacuum at an aspiration port in fluidic communication with the evacuation lumen, wherein the aspiration port is sized and shaped to retain and immobilize a solid deposit within the enclosed location of the subject, when the system is aspirating, an ablation instrument forming part of or functionally and structurally integrated with the liquid-jet powered aspiration instrument, such that an ablation device of the ablation instrument is movable with respect to the liquid-jet powered aspiration instrument to enable an operator of the system to position the ablation device in proximity with the aspiration port to breakdown the solid deposit into a plurality of smaller deposits, when the system is in operation.

In some implementations, a method includes forming a liquid jet with a nozzle and directing the liquid jet into an evacuation lumen of an evacuation tube and proximate one or more aspiration port openings in a side wall of the evacuation tube to generate a Venturi-created or venture-assisted vacuum at the one or more aspiration port openings, and capturing and retaining the biological object at the one or more aspiration openings, venting into the location a selectable fraction of a total volumetric flow rate of liquid aspirated by the Venturi-created or Venturi-assisted vacuum in the forming step, wherein vented liquid exits the evacuation lumen into the location surrounding the evacuation tube through one or more vent port openings in a side wall of the evacuation tube that are located downstream of the one or more aspiration port openings.

In some implementations, a method includes forming a liquid jet with a nozzle and directing the liquid jet into an evacuation lumen of an evacuation tube and proximate one or more aspiration port openings in a side wall of the evacuation tube to generate a Venturi-created or venture-assisted vacuum at the one or more aspiration port openings, and capturing and retaining the biological object at the one or more aspiration port openings, ablating the biological object into a plurality of particles using an ablation device, and removing the plurality of particles from the location internal to the subject via the Venturi-based vacuum at the one or more aspiration port openings.

The present disclosure encompasses methods of making one or more of the implementations described herein, for example, an aspiration device. In still another instance, the present disclosure encompasses methods of using one or more of the implementations described herein, for example, an aspiration device.

BRIEF DESCRIPTION OF THE DRAWINGS

Non-limiting examples of the present disclosure will be described by way of example with reference to the accompanying figures. For purposes of clarity, not every component is labeled in every figure, nor is every component of each example of the disclosure shown where illustration is not necessary to allow those of ordinary skill in the art to understand the disclosure.

FIGS. 2C-2H are cross-sectional views of steps of removing a kidney stone from a patient's kidney.

FIG. 8A is a schematic diagram of a distal end of an example liquid-jet powered Venturi-assisted medical aspiration instrument with at least one aspiration port opening.

FIGS. 8B-8C are schematic diagrams of example configurations for the aspiration port openings of the liquid-jet powered Venturi-assisted medical aspiration instrument of FIG. 8A, with and without a mesh for blocking entry of larger debris from passing through the aspiration port opening.

FIGS. 8D-8E are schematic diagrams of example configurations for the one or more vent port openings of an instrument such as depicted in FIG. 8A, with and without a mesh for blocking entry of larger debris from passing through the one or more vent port openings.

DETAILED DESCRIPTION

Figure 1:
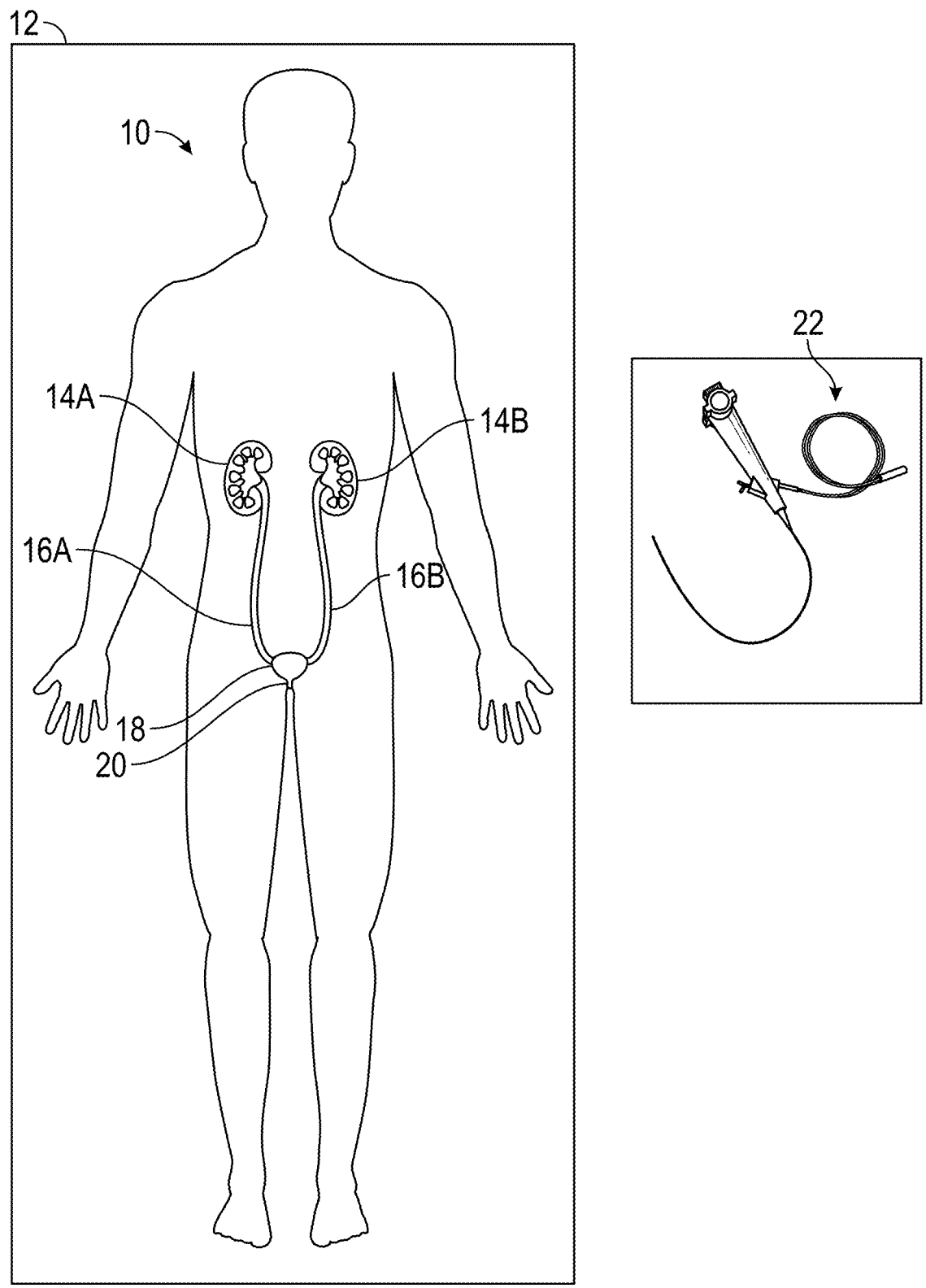
FIG. 1 is a top view of a patient prepared for a ureteroscopy.

Implementations of the present disclosure generally relate to biological object removal systems, devices, and related methods. Certain implementations generally relate to devices and systems configured to generate a vacuum, for instance, capable of manipulating, immobilizing, and/or aspirating a solid object and/or debris from an ablated or comminuted solid object in a liquid filled environment. In some cases, the vacuum is generated and/or maintained via a Venturi effect. Configurations described herein may be useful, for example, for capturing, manipulating, immobilizing, and/or removing biological objects from anatomical structures inside the body, such as intact kidney stones, or portions of kidney stones, or debris from ablated kidney stones. For example, some kidney stones may be generally small enough to pass through the ureter of a subject but may be unable to due to, for example, a disease state of the subject. In some cases, the kidney stones are too large or are otherwise unable to pass through the ureter of the subject. In some cases, the systems and devices described herein include an ablation instrument, such as a laser or ultrasound, configured to ablate one or more solid objects into a plurality of smaller solid objects. Ultrasound can include an ultrasound ablation tool configured to provide ultrasonic lithotripsy. Such systems may be useful, for example, for breaking up kidney stones that are too large to pass through the ureter of a subject. Additionally, or alternatively, the vacuum created by the devices and systems described herein may be useful for aspirating a plurality of smaller solid objects into the device, thus removing it from the liquid filled environment (e.g., the kidney).

Some implementations generally relate to methods of using the systems and devices disclosed herein. For example, the devices and systems described herein may be useful for capturing and/or removing a biological object at a location internal to a subject (such as, from an anatomical structure). Biological objects can include blood clots, tumors, tissue samples, and unitary or fragmented urinary calculi such as bladder stones, ureter stones, and kidney stones.

The phrase "location internal to a subject" as used herein generally refers to a cavity, orifice, anatomical structure, or organ within a subject. For example, in some cases, the location internal to the subject is a kidney, a bladder, a heart, a colon, a duodenum, an ileum, a jejunum, a stomach, an esophagus, an intestine, a mouth, a liver, a lung, a pancreas, a spleen, a lymph node, a (blood) vessel, a gland, an ear canal, a urethra, a uterus, a gallbladder, an ovary, or a nasal cavity. In an example set of cases, the location internal to the subject is a kidney or bladder.

The term "subject," as used herein, refers to an individual organism such as a human or an animal. In some cases, the subject is a mammal (e.g., a human, a non-human primate, or a non-human mammal), a vertebrate, a laboratory animal, a domesticated animal, an agricultural animal, or a companion animal. In some cases, the subject is a human. In some cases, the subject is a rodent, a mouse, a rat, a hamster, a rabbit, a dog, a cat, a cow, a goat, a sheep, or a pig.

In some cases, the articles and systems described herein are administered to a subject. In certain cases, the system may be administered surgically (e.g., inserted), through an incision, typically endoscopically using a catheter or similar, in other cases, the devices may be inserted into the body orally, rectally, vaginally, nasally, or uretherally. In certain cases, the system is administered such that at least a portion of the system accesses a location internal to the subject such as an organ (e.g., the kidney).

In some cases, the system is configured to manipulate a liquid at the location internal to the subject. As used herein, a "liquid" is given its ordinary meaning. A liquid generally cannot maintain a defined shape and will flow during an observable time frame to fill the container in which it is put. Thus, the liquid may have any suitable viscosity that permits flow. If two or more liquids are present, each liquid may be independently selected among essentially any liquids by those of ordinary skill in the art. Typically, the liquid will be sterile water or sterile normal saline or phosphate buffered saline or other osmotically balanced liquid or another IV fluid suitable for use in a human patient.

Implementations of the disclosure are related to devices and systems suitable for use in a surgical procedure at a location internal to a subject. In some cases, the devices are suitable for use at a location internal to a subject at least partially filled with a surrounding liquid (e.g., an organ of the subject).

In some cases, the devices described herein are liquid-jet powered instruments. In some cases, the instruments described herein are Venturi-assisted instruments. In some cases, the instruments described herein are useful for ablation and/or ablation assistance (e.g., of a solid deposit such as a kidney stone). For example, the instruments described herein may be useful for capturing a solid deposit such that it may be ablated (e.g., by an ablation instrument such as a laser, ultrasound probe, or other suitable ablation instruments). As described herein, the liquid-jet powered instruments, Venturi-assisted instruments, and/or other instruments can refer to a catheter, an aspiration catheter, and/or an evacuation catheter.

Overview

Kidney stones affect approximately 10% of individuals in the United States, with nearly 470,000 surgeries performed annually to relieve symptoms and prevent complications. Current treatment modalities include extracorporeal shock wave lithotripsy (ESWL), ureteroscopy (URS), and percutaneous nephrolithotomy (PCNL). Of these, URS is the most prevalent, accounting for approximately two-thirds of all kidney stone surgeries due to its versatility in treating a broad range of stone sizes using lithotripsy devices to break up stones and baskets to remove fragments and small stones. URS procedures have been steadily increasing by about 15% annually since 2012.

Kidney stone procedures aim to maximize the removal of stones and fragments. Despite advancements in lithotripsy and ureteroscopy technology, stone clearance remains inconsistent, particularly for larger or more complex stones, with stone-free rates (defined as no stones remaining on follow-up CT scan imaging) often declining to 50% in these cases. Residual fragments can lead to symptoms and complications, including acute stone events, regrowth, and infection. Consequently, achieving complete stone clearance is critical to reducing reintervention rates and optimizing long-term outcomes.

There are still necessary improvements in the efficiency and safety of URS, including pressure and temperature management inside the kidney, maintaining a clear visual field, and preventing stone fragments from moving away from operative devices. Enhancing these aspects of URS aims to prevent injury and reduce procedure times.

Recent innovations, such as direct in-scope suction (DISS) and flexible and navigable sheaths (FANS) aim to improve stone-free rates and procedural efficiency, though these technologies have limitations. DISS uses the ureteroscope's small working channel to aspirate dust and small debris, which enhances visibility and helps regulate intrarenal pressure (IRP). However, the narrow diameter of the working channel restricts the removal of larger fragments and causes vacuum pressure loss at the distal end, reducing its ability to effectively clear debris and control retropulsion. This compromised visibility and resulting retropulsion increase the risk of unintended ablation of kidney walls and reduce procedural efficiency. Furthermore, the reduction in suction can lead to an increase in IRP which can have significant consequences (as described below).

Ureteral access sheaths (UAS), including vacuum-assisted FANS models, offer an alternative approach by combining suction with irrigation to maintain low IRP and reduce the "snow globe" effect caused by debris during lithotripsy. FANS provide additional maneuverability, allowing for navigation through renal calyces to suction larger fragments. To use FANS efficiently, high-pressure irrigation is required notably to remove fragments. However, manual control of irrigation and suction often causes kidney distension or collapse during procedures due to difficulties in balancing in and out flow and maintaining IRP. This complexity adds to the surgeon's workload, as they must also manage laser ablation time and wattage to prevent temperature spikes, further diverting their focus and decreasing procedural efficiency, while amplifying the risks associated with managing pressure and temperature Limitations in current laser lithotripsy techniques during URS often lead to prolonged procedures and incomplete stone clearance. Surgeons may attempt mechanical capture and removal of residual fragments with stone retrieval tools, adding time and complexity and requiring coordination with support staff. Alternatively, "dusting" techniques may be employed to break stones into passable particles, though residual dust and small fragments can lead to acute stone events. Limited visibility, often caused by dust clouds and bubbles, hampers precise targeting which leads to residual stone fragments and requires increased irrigation, prolonging the procedure. To prevent thermal injury, surgeons may lower laser wattage or operate it intermittently, which also increases procedure times.

Effective IRP management is essential to prevent complications during ureteroscopy. Although elevated irrigation flow improves visibility during lasing, it can concurrently increase IRP, raising the risk of pyelovenous, pycolymphatic, and pyelosinus backflow, which can lead to severe outcomes like urosepsis, systemic infection, and kidney damage. These risks not only increase the cost of the procedure due to prolonged hospital stay but also increase the risk of patient death. While UAS and FANS improve fluid outflow to help manage IRP, their use entails risks. Larger-diameter UAS, though effective at reducing IRP, increases the risk of ureteral injury, especially in patients with narrow ureters. One study found that nearly 50% of patients experience ureteral wall damage with UAS over 11 Fr, with the risk rising for even larger sheaths. Although UAS and FANS technologies can control IRP to prevent overpressure and distension, they risk kidney collapse under vacuum suction, leading to bleeding and other complications.

Emerging pressure-sensing ureteroscopes offer real-time IRP monitoring but do not actively control it, leaving pressure regulation in the hands of the surgeon, who must monitor pressure and manually adjust irrigation or use aspiration to lower IRP. This reactive approach relies on the surgeon's ability to interpret and respond promptly to prevent complications.

Temperature management with lasers, particularly Holmium: YAG and Thulium fiber lasers, also presents challenges. Temperatures above 43° C. can cause tissue damage, necessitating techniques like increased or chilled irrigation and reduced laser activation or wattage, which often prolong procedures.

Despite advancements, the current ureteroscopic lithotripsy paradigm challenges surgeons' ability to see, effectively clear stones and fragments, and manage pressure and temperature to safely navigate and treat renal calculi in the upper urinary tract. Existing methods frequently leave fragments behind, resulting in complications for over 40% of patients and requiring re-treatment within a year for up to ⅓ of cases.

The systems and methods described herein aim to address many of these limitations, offering substantial improvements in efficacy, safety, and efficiency. This novel approach has the potential to reduce complications, decrease re-treatment rates, and set a new standard for kidney stone surgery.

Removal of Biological Objects

As shown in FIG. 1, a patient 10 can include a first kidney 14A and a second kidney 14B. The patient 10 can further include a first ureter 16A, a second ureter 16B, a bladder 18, and a urethra 20.

The first kidney 14A and the second kidney 14B can be internal organs located within the torso of the patient 10 and positioned below or inferior to the ribcage and laterally on either side of the patient's spine. The first kidney 14A and the second kidney 14B can be configured to process fluids.

For example, the first kidney 14A and the second kidney 14B can filter blood, remove waste and extra fluid, balance fluids, and produce hormones and red blood cells. The first kidney 14A and the second kidney 14B can filter fluids resulting in urine. In some cases, the first kidney 14A and/or the second kidney 14B can produce solid deposits or kidney stones. The solid deposits can be formed when the fluids within the first kidney 14A and/or the second kidney 14B include too many crystal-forming substances in relation to the amount of fluid. In some examples, the first kidney 14A and/or the second kidney 14B can include a high concentration of calcium, oxalate, and/or uric acid in relation to the amount of fluid. Accordingly, the fluid is insufficient to dilute the crystal-forming substances and is insufficient to prevent the crystal-forming substances from forming solid deposits.

The first ureter 16A and the second ureter 16B can each be a hollow tube configured to transport fluids. The first ureter 16A and the second ureter 16B can be located in the patient's torso or abdomen.

The bladder 18 can be a hollow, elastic internal organ located in the lower part of a patient's abdomen. The bladder 18 can be configured to collect and store fluids. For example, the bladder 18 can be configured to collect and store urine from the first kidney 14A and/or the second kidney 14B.

The urethra 20 can be a hollow tube configured to transport fluids. The urethra can be in fluid communication with an external environment. Accordingly, the urethra 20 can be configured to expel fluids from the patient's body.

The first kidney 14A and the second kidney 14B can be in fluid communication with the bladder 18 via a corresponding first ureter 16A or second ureter 16B. For example, the first ureter 16A can extend between the first kidney 14A and the bladder 18 and the second ureter 16B can extend between the second kidney 14B and the bladder 18. Accordingly, fluids can be passed from the first kidney 14A and/or the second kidney 14B to the bladder 18 via the corresponding first ureter 16A or second ureter 16B. The bladder can be in fluid communication with an external environment via the urethra 20.

The above identified organs can define the urinary tract or urinary system of a patient. In a healthy patient, fluids such as urine can pass unobstructed through the urinary system. Solid deposits formed within the kidneys can block fluid flow within the urinary system. Blocking the fluid flow can result in a buildup of fluid and pressure causing pain and/or discomfort to the patient. Additionally, in some cases, the solid deposits can have an irregular shape. For example, the solid deposits can have sharp edges. The sharp edges can puncture tissue resulting in additional pain, discomfort, bleeding, and possible infection. To alleviate pain, discomfort, and/or otherwise treat or prevent further risk of injury, methods have been developed to remove solid deposits.

The devices and methods for removing solid deposits from a patient's urinary system can include an operating table 12 and instruments (i.e., devices) including an evacuation tube such as a ureteroscope 22.

The operating table 12 can be a device configured to support and/or restrain a patient during a medical procedure. For example, the operating table 12 may support an unconscious and/or medicated patient 10 for the duration of a medical procedure such as a ureteroscopy.

The ureteroscope 22 can include a thin, tube-shaped shaft. The thin, tube-shaped shaft can have an interior lumen sized to receive at least a portion of a solid deposit. The ureteroscope 22 can be configured to pass through the patient's urinary system to reach the solid deposit (such as, a kidney stone). The ureteroscope 22 can further include a light and a lens to assist a physician in navigating the patient's urinary system and/or identifying solid deposits. The ureteroscope 22 can include a working channel. In some cases, a laser can be placed into the working channel of the ureteroscope 22. The laser can be configured to apply energy to and break up solid deposits. Additionally or alternatively, in some cases, a gripping mechanism can be placed into the working channel of the ureteroscope 22. The gripping mechanism can be configured to secure one or more solid deposits for extraction.

FIGS. 2A-2H illustrate methods and steps of using a ureteroscope 22 to remove solid deposits from a patient's kidney. While FIGS. 2A-2H illustrate the ureteroscope 22 being applied to the second kidney 14B, the approaches described herein can be utilized for removing solid deposits from either kidney and/or anywhere along the urinary system or, more generally, from any location in the body.

Figure 2A:
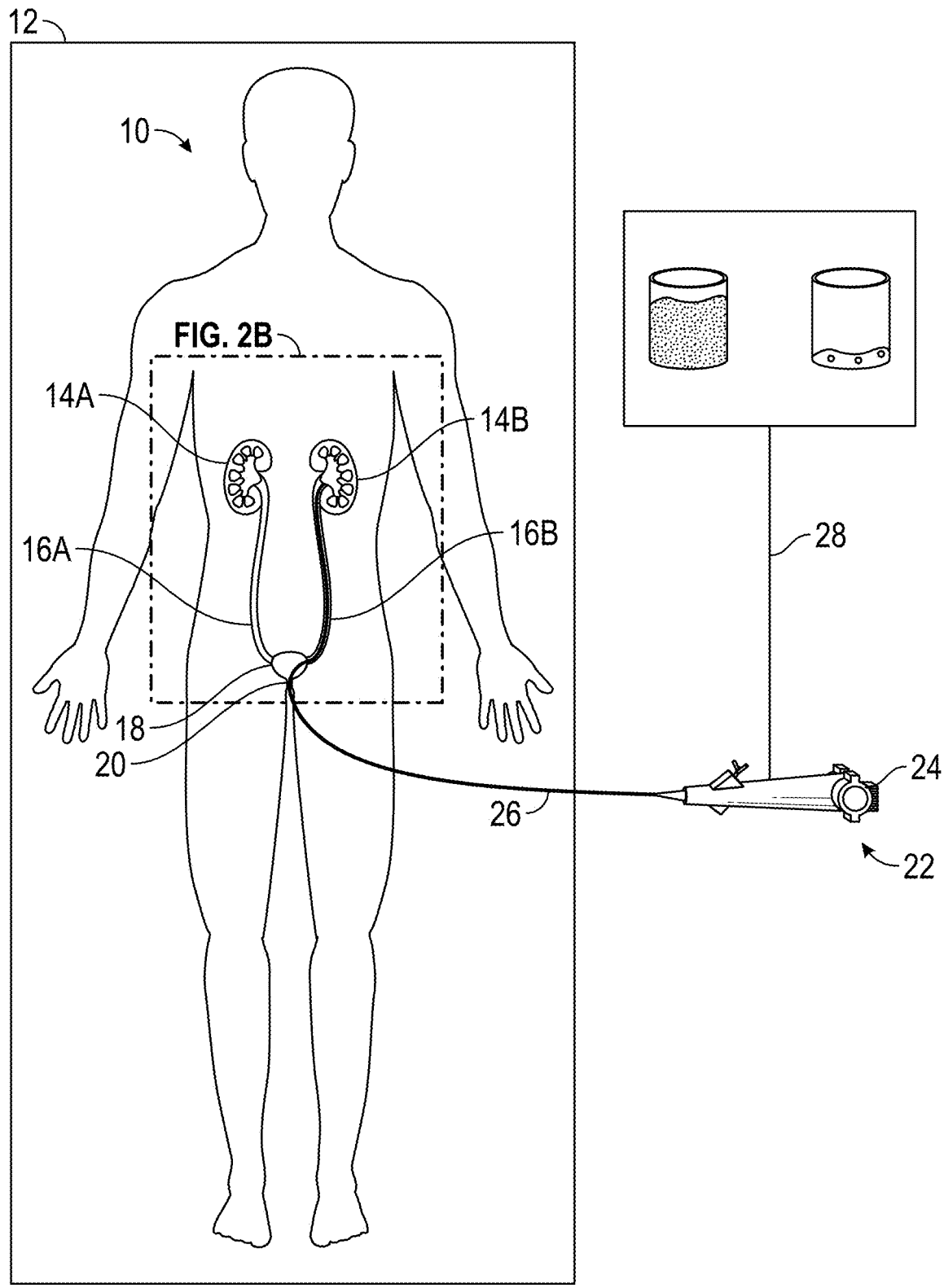
FIG. 2A is a top view of a ureteroscope being inserted into a patient.

As shown in FIG. 2A, a patient 10 can be supported on an operating table 12. In some cases, the patient 10 can be medicated. For example, the patient 10 can be generally and/or locally anesthetized. The ureteroscope 22 can be introduced to the patient's urinary system. For example, the ureteroscope 22 can be introduced via the urethra 20. In some cases, the ureteroscope 22 can include a sheath 26 sized to pass through the patient's urethra 20, bladder 18, ureter 16A/16B and/or kidney 14A/14B. The sheath 26 can be a tube. For example, the sheath 26 can have an outer diameter between about 0.5 and 4 mm, or between about 1.5 and 3.5 mm. In some cases, the sheath 26 can have a length between 40 cm and 100 cm. In some cases, the sheath 26 can have a length between 50 cm and 70 cm. For example, the sheath 26 can be about 60 cm in length. The sheath 26 can include the working channel of the ureteroscope 22. The working channel can extend through the length of the sheath 26. The working channel can have an outer diameter smaller than the outer diameter than the sheath 26. In some cases, the working channel can have an outer diameter between about 1.2 mm and 1.5 mm. The ureteroscope 22 can further include a handle portion 24 and a fluid supply catheter 28. The handle portion 24 can include an eyepiece or camera for a physician to see for navigation and identification of solid deposits. For example, the handle portion 24 can include a digital complementary metal oxide semiconductor ("CMOS") camera. The handle portion 24 can be a Y-connector configured to fluidly connect the ureteroscope 22 to a first fluid supply (also referred to as a first fluid source and/or a first fluid reservoir) for irrigation, a second fluid supply (also referred to as a second fluid source and/or a second fluid reservoir) for aspiration, and/or laser or gripping mechanism insertion.

Figure 2B:
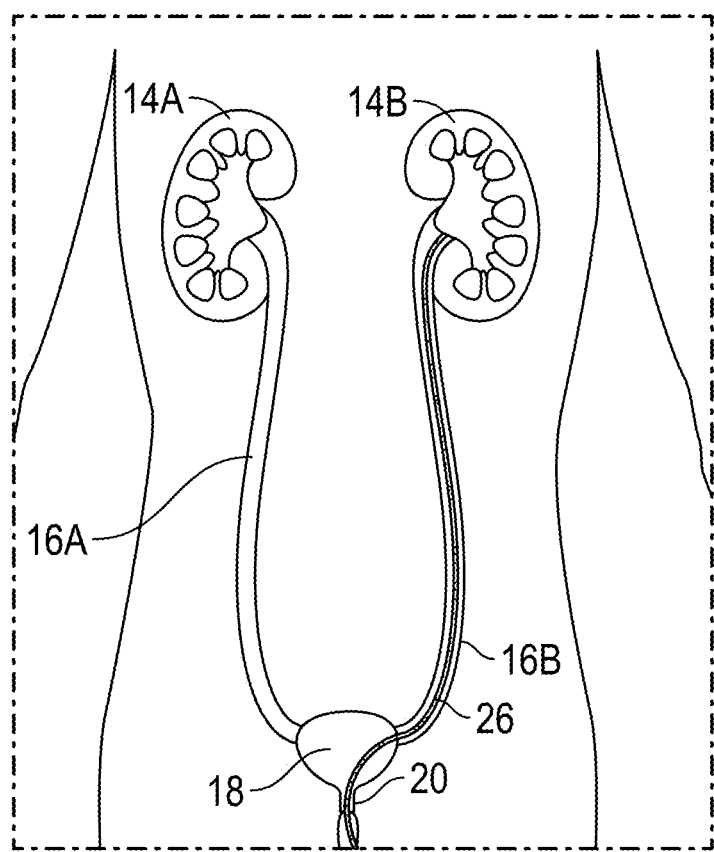
FIG. 2B is a top view of a ureteroscope being positioned within a patient's kidney.

FIG. 2B illustrates a sheath 26 extending through the patient's urinary system and positioned in the second kidney 14B via the second ureter 16B, bladder 18, and urethra 18. The ureteroscope 22 may be generally used to identify and remove solid deposits.

Figure 2E:
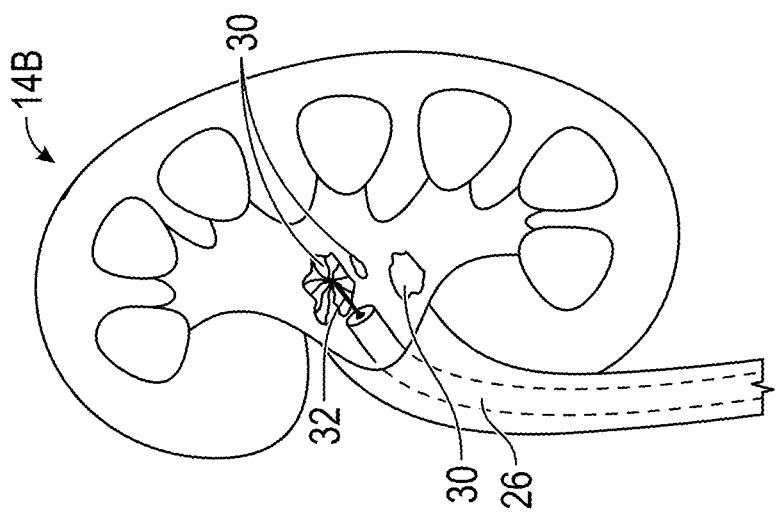
Figure 2D:
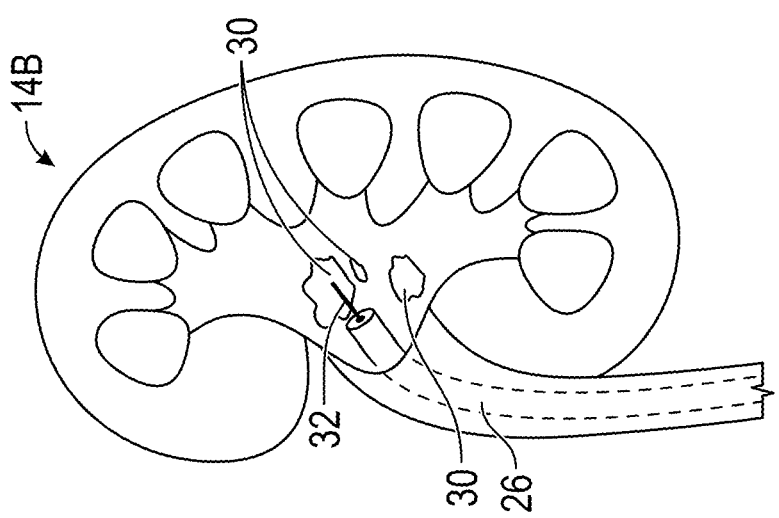
Figure 2C:
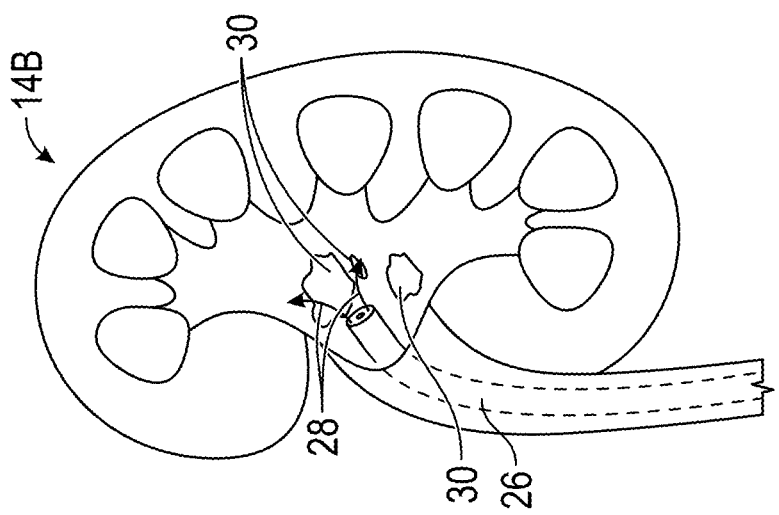

FIG. 2C illustrates a step of inflating the second kidney 14B. As described herein, the ureteroscope 22 can include a sheath 26. The sheath 26 can be in fluid communication with a fluid source. The fluid source can also be referred to as a fluid supply and/or a fluid reservoir. The fluid source can be an input supply of a fluid to be used by a ureteroscope 22 to irrigate and/or flush the patient's urinary system. In some cases, the sheath 26 can introduce a fluid 28 into the second kidney 14B to expand the kidney and enhance visibility. For example, expanding the second kidney 14B can assist a physician in identifying one or more solid deposits 30.

In some cases, the ureteroscope 22 can include an end-effector located at the distal end of the sheath 26. The end-effector can be configured to grasp and secure a solid deposit. After securing the solid deposit, the sheath 26 and/or ureteroscope 22 can be removed from the patient 10. In some cases, the ureteroscope 22 can be in fluid communication with an aspiration source. For example, the ureteroscope 22 can be in fluid communication with a vacuum source. Accordingly, the ureteroscope 22 can be configured to aspirate solid deposits through the sheath 26. In some cases, the solid deposits may be too large to be removed by the ureteroscope 22.

FIG. 2D illustrates a step of applying energy 32 to at least one of the one or more solid deposits 30. In some cases, the energy 32 can be a laser. For example, a laser fiber can extend through the sheath 26 and be configured to emit laser energy toward at least one of the one or more solid deposits 30.

As shown in FIG. 2E-2G, the energy 32 can be sufficient to fracture and/or break up the solid deposits 30 into debris of fragmented solid deposits. The fragmented solid deposits can be smaller than the original solid deposit. For example, the fragmented solid deposits can be reduced to dust particles. Accordingly, the fragments may be sized sufficiently small to be aspirated through the sheath 26. In some cases, the fragments may remain too large to be aspirated through the sheath 26. Accordingly, the energy 32 can be applied to the fragments to further fracture and/or break up the solid deposits 30 as shown in FIG. 2G.

FIG. 2H illustrates a step of aspirating the solid deposits through the sheath 26. The ureteroscope 22 can be withdrawn and removed from the patient 10 after the solid deposits are successfully removed from the patient 10.

Figure 3A:
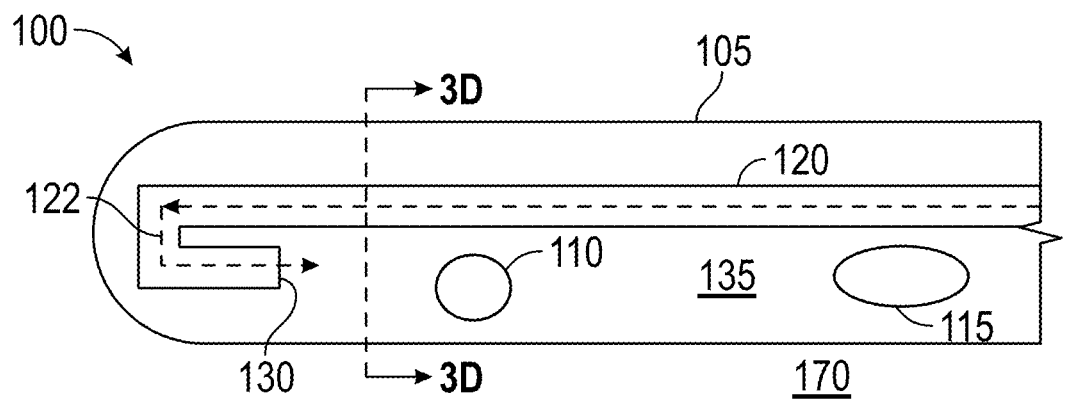
FIG. 3A is a schematic diagram of a distal end of an example liquid jet aspiration device.

In some implementations, an instrument 100 (sometimes referred to as devices) described herein can include a liquid-jet powered aspiration tool or catheter. Such a device will typically include an evacuation tube. For example, as illustrated in FIG. 3A (which depicts the distal end of a liquid-jet powered aspiration catheter), instrument 100 can include an evacuation tube 105. In some cases, the instrument 100 can be the same as the ureteroscope 22 described herein. In some cases, the evacuation tube 105 can include one or more aspiration port openings 110 and the one or more vent port openings 115. In some cases, the one or more aspiration port openings 110 are formed on a sidewall of the evacuation tube 105. In some cases, the one or more vent port openings 115 is positioned downstream (e.g., relative to the flow of liquid within the evacuation tube 105, when the device is in operation) of the one or more aspiration port openings 110, as described in more detail herein and shown in FIG. 3A. Those of ordinary skill in the art would understand, based upon the teachings of this specification, that the instrument 100 is generally considered in operation when a liquid is flowing within one or more components of the instrument 100 (e.g., the evacuation tube, a liquid supply lumen, etc.).

As described herein, the instrument 100 can be configured, in some cases, to remove a biological object from a location internal to a subject (e.g., via ablation of the biological object such as a solid deposit and aspiration of at least a portion of the biological object from the location internal to the subject).

In some cases, the biological object can be a urinary calculus. For example, in some cases, the biological object can be a solid deposit or stone that forms in an anatomical structure such as the urinary tract. For example, the biological object can be formed in the kidneys, ureter, bladder, prostate gland, and/or urethra. In some cases, the stone is a kidney stone, a bladder stone, and/or a ureter stone. In some cases, the stone can be unitary (i.e., non-fragmented) or fragmented. A fragmented urinary calculus can include at least a portion of the urinary calculus. In some cases, the anatomical structure can include another specific, identifiable part of a patient's body. For example, the anatomical structure can include the gallbladder, salivary glands, and pancreas.

While FIG. 3A shows a single one of the one or more aspiration port openings 110 and a single one of the one or more vent port openings 115, the instrument 100 may include any suitable number of aspiration port openings 110 (e.g., one or more, two or more, three or more, four or more, etc. aspiration port openings 110) and/or any suitable number of vent port openings 115 (e.g., one or more, two or more, three or more, four or more, etc. vent port openings 115). In some cases, instrument 100 can include a liquid supply lumen 120.

While FIG. 3A shows the one or more aspiration port openings 110 and the one or more vent port openings 115 on the same side of the evacuation tube 105, in some cases, the one or more aspiration port openings 110 and the one or more vent port openings 115 may be located on different sides of the evacuation tube 105, as described in more detail herein.

In some cases, the evacuation tube 105 can include a liquid supply lumen 120. In some cases, the liquid supply lumen 120 can include an outlet 130. In some cases, the liquid supply lumen 120 can include a nozzle suitable for forming a liquid jet at the outlet 130. The liquid jet can have a flow rate between 20 and 60 ml/min. In some cases, the liquid jet can have a flow rate of about 40 ml/min. In some cases, the outlet 130 may be configured and positioned to direct a liquid jet (e.g., a liquid jet formed at a nozzle associated with the outlet 130) e.g., into the evacuation tube 105 (e.g., along an evacuation lumen 135 of the evacuation tube 105). In some cases, upon exiting the outlet 130 (and/or a nozzle positioned at the outlet 130), the liquid 122 flows past at least a portion of the one or more aspiration port openings 110 thereby generating a vacuum at the one or more aspiration port openings 110, relative to an environment external to the evacuation tube 105 e.g., while the instrument 100 is in operation. In some cases, the vacuum generated is sufficient to aspirate at least a portion of the surrounding liquid 170 from an environment external to the evacuation tube 105 (e.g., at a location internal to a subject or patient, as described in more detail herein). In some cases, the liquid jet, at the one or more aspiration port openings 110, generates a Venturi-created and/or Venturi-assisted vacuum while the instrument 100 is in operation, (e.g., sufficient for capturing and/or immobilizing and/or evacuating a solid deposit e.g., kidney stone, bladder stone, gall stone, etc., at a location internal to a subject). Nozzles suitable for use with the articles and systems are described in more detail, below. Taking advantage of the Venturi-effect (as explained herein) at or near the distal end of the ureteroscope to produce negative pressure can overcome the limitations of existing ureteroscopes that only include an aspiration pump at the proximal end. Higher suction can improve surgical efficacy by maintaining the solid deposits at an optimal distance from an ablation instrument thereby reducing possible retropulsion. Additionally, improved suction may position solid deposits away from organ tissue thereby reducing the risk of patient movement and accidental tissue ablation.

In some cases, the one or more vent port openings 115 may be sized, positioned and configured to eject at least a portion of the liquid 122 flowing along the evacuation lumen 135 under at least some conditions of normal operation, as described in more detail herein. The evacuation lumen 135 may comprise any suitable cross-sectional shape. Non-limiting examples of suitable cross-sectional shapes include triangles, squares, rectangles (e.g., having any suitable aspect ratio) circles, ovals, polygons (e.g., pentagons, hexagons, heptagons, octagons, nonagons, dodecagons, or the like), rings, irregular shapes, or the like. In some cases, the instrument 100 disclosed herein comprise a liquid source. Any suitable liquid source capable of being pressurized and passed through the devices disclosed herein may be used. For example, in some cases, the liquid source is a physiological fluid. In some cases, the physiological fluid is a saline solution (e.g., 0.9% wt NaCl), dextrose solutions (e.g., 5% wt), lactated ringers solution, ringers solution, dextran solution, plasmalyte solution or the like. Other solutions are also possible, according to other cases.

As would be understood by those of ordinary skill in the art, based upon the teachings of the specification, the one or more aspiration port openings 110 and/or the one or more vent port openings 115 can be configured and designed such that an internal portion (i.e., lumen) of the evacuation tube 105 is in fluidic communication with a surrounding liquid 170 (e.g., during operation of the instrument). In some cases, the one or more vent port openings 115 may be configured and designed such that at least a portion of the surrounding liquid 170 enters the evacuation tube 105 via the one or more vent port openings 115, when the instrument 100 is in operation. In some cases, the aspiration port openings 110 may be configured and designed such that at least a portion of a liquid 122 present and/or flowing within the evacuation tube 105 exits the evacuation tube 105 via the aspiration port openings 110 (e.g., to a surrounding environment at the location internal to the subject) during operation of the instrument 100. In some cases, liquid may not substantially pass through one or more aspiration port openings 110 when the instrument 100 is in operation. See FIG. 4B and associated discussion herein for more details regarding flow patterns and operational modes related to the aspiration and vent ports.

Figure 3B:
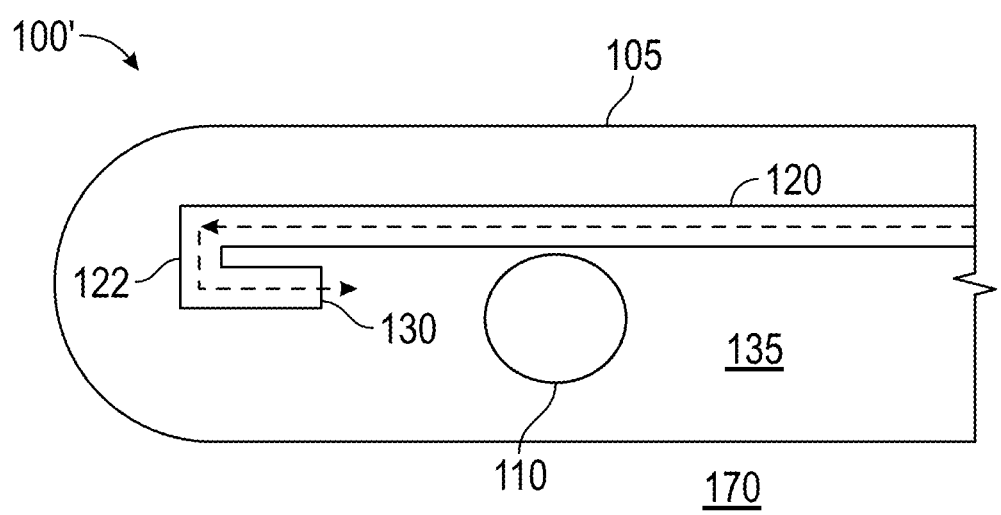
FIG. 3B is a schematic diagram of a distal end of an example liquid jet aspiration device.

While FIG. 3A shows an instrument 100 including the one or more vent port openings 115, in some cases, the instrument 100 may not include any of the one or more vent port openings 115, (only aspiration port openings 110) as shown in FIG. 3B and as described in more detail below.

The instrument 100 may be configured as a liquid-jet powered aspiration medical instrument. For example, as illustrated in FIG. 4A, the instrument 200 (which can be similar to the instrument 100 or any other instrument described herein except for the differences described herein) can include an evacuation tube 205. In some cases, the evacuation tube 205 may be sized with respect to the size of the one or more aspiration port openings 210 such that a biological object (e.g., solid deposit such as a kidney stone, at least a portion of an ablated kidney stone, etc.) may be aspirated through the aspiration port opening(s) 210 and removed via the evacuation tube 205 (see e.g., FIG. 3D which depicts the relative size of an evacuation tube 105 and the one or more aspiration port openings 110).

In some cases, the evacuation tube 205 can include one or more aspiration port openings 210 e.g., formed in a side wall of the evacuation tube. In some cases, evacuation tube 205 can include one or more vent port openings 215. The one or more vent port openings 215 can be positioned downstream (e.g., when the instrument is in operation) of one or more aspiration port openings 210. In some cases, the instrument includes a liquid supply lumen 220. As shown in FIG. 4A, the liquid supply lumen 220 can be positioned against a sidewall of the evacuation tube 205. In some cases, the liquid supply lumen 220 includes a nozzle 225. The nozzle 225 can be configured to form a liquid jet at an outlet 230 of the liquid supply lumen 220. In some cases, the outlet 230 of the liquid supply lumen 220 may be configured and positioned to direct the liquid jet formed by the nozzle 225 into and along an evacuation lumen 235 of the evacuation tube 205. As shown in FIG. 4A, the evacuation lumen 235 can extend from a sidewall of the evacuation tube 205 opposite the liquid supply lumen 220 up to the medial sidewall of the liquid supply lumen 220. In some cases, one or more aspiration port openings 210 is positioned downstream relative to the outlet 230 when the instrument 200 is in operation (e.g., relative to the flow of liquid within the evacuation tube 205, when the instrument 200 is in operation). As described herein, the instrument 200 may include any suitable number of aspiration port openings 210 (e.g., one or more aspiration port openings 210, two or more aspiration port openings 210, three or more aspiration port openings 210, four or more aspiration port openings 210, five or more aspiration port openings 210, ten or more aspiration port openings 210, or any suitable plurality of aspiration port openings 210, e.g., distributed circumferentially around the evacuation tube).

In some cases, one or more vent port openings 215 may be positioned on a different side of the evacuation tube 205 relative to at least another one of the one or more vent port openings 215 and may be positioned downstream relative to the one or more aspiration port openings 210 when the instrument 200 is in operation. For example, in some cases, a first vent port opening 215 may be positioned on a different side of the evacuation tube 205, relative to a second vent port opening 215. As described herein, the instrument 200 may include any suitable number of vent port openings 215 (e.g., one or more vent port openings 215, two or more vent port openings 215, three or more vent port openings 215, four or more vent port openings 215, five or more vent port openings 215, ten or more vent port openings 215, or any suitable plurality of vent port openings 215).

In some cases, the number of aspiration port openings 210 and vent port openings 215 may include any suitable combination of each (e.g., one or more aspiration port openings 210 and one or more vent port openings 215, as described herein).

In some cases, the positioning of the aspiration port openings 210 relative to the vent port openings 215 can be such that a liquid (e.g., liquid contained within the liquid source 240), upon exiting the nozzle, flows past at least a portion of one or more aspiration port openings 210 generating a vacuum at the one or more aspiration port openings 210, relative to an environment external to the evacuation lumen 235, when the instrument 200 is in operation. As described in more detail herein, in some cases, the flow of the liquid past the one or more aspiration port openings 210 generates Venturi-effect suction, thereby producing the above-mentioned vacuum at the one or more aspiration port openings 210.

Figure 3C:
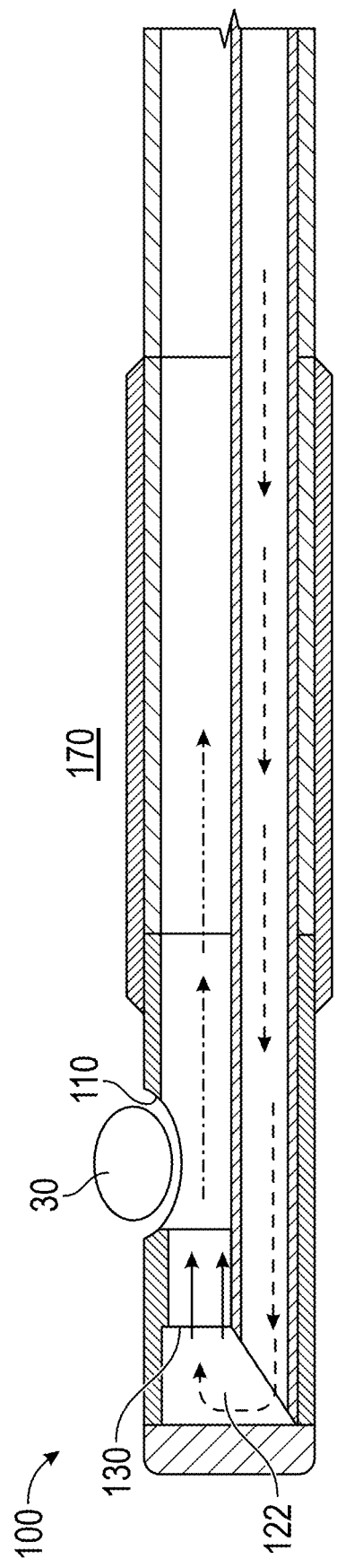
FIG. 3C is a schematic diagram of an example liquid jet aspiration device demonstrating a Venturi principle effect.

For example, as shown illustratively in FIG. 3C, and without wishing to be bound by theory, the flow of a liquid within a liquid supply lumen 120 (e.g., pressure, flow rate) may be altered, as may be the design of the nozzle, such that a desired level of Venturi-effect suction is produced proximate at least one of the one or more aspiration port openings 110.

Without wishing to be bound by any particular theory, the Venturi effect can explain a reduction in fluid pressure resulting from an increase in fluid flow of a fluid flowing through a constricted section. The Venturi effect can adhere to a conservation of flow rates relative to pressure and velocity. For example, the Venturi effect can follow Bernoulli's principle relating pressure and kinetic energy density. For example, the Venturi effect can follow the relationship $P_1 + \frac{1}{2}\rho V_1^2 = P_2 + \frac{1}{2}\rho V_2^2$ wherein $P_1$ is the pressure at the first location along a flow path, $V_1$ is the velocity of the fluid at the first location along the flow path, $P_2$ is the pressure at a second location along the flow path, and $V_2$ is the velocity of the fluid at the second location along the flow path, $\rho$ is the fluid density assumed constant, wherein the first location and the second location are at the same height. Accordingly, the velocity and pressure are inversely related. For example, the pressure decreases proportional to the square of the velocity increase and vice versa. $P_2 = P_1 + \frac{1}{2}\rho(V_1^2 - V_2^2)$. Based on this relationship as fluid velocities increase, negative pressure (suction) can be created.

A fluid flow rate can also be defined as the velocity of the fluid passing through an area. For example, a fluid flow rate can follow the relationship: AV, wherein A is the cross-sectional area of a tube, conduit, or other channel, and V is the velocity of the fluid passing through the cross-sectional area. The flow rate within an internal passageway can be constant for non-compressible fluids. Thus, the following relationship can apply for a constant flow rate: $A_1V_1 = A_2V_2$, wherein $A_1$ is the cross-sectional area at a first location along a flow path, $V_1$ is the velocity of the fluid at the first location along the flow path, $A_2$ is the cross-sectional area at a second location along the flow path, and $V_2$ is the velocity of the fluid at the second location along the flow path. Accordingly, the velocity and area are inversely related. For example, the velocity can increase as the cross-sectional area decreases. Thus, the Venturi effect can be related to the constant flow rate such that the change in pressure is proportionally related to the square of the change in cross-sectional area. Accordingly, the pressure can decrease as the cross-sectional area decreases and vice versa. Thus, a nozzle or constriction in the fluid flow path can increase the velocity of the fluid flow and decrease pressure creating a vacuum.

In some cases, the instrument 100, device, and/or system may not include one or more vent port openings 115. For example, referring again to FIG. 3B, the instrument 100' can include one or more aspiration port openings 110 but does not include one or more vent port openings 115. The instrument 100' can be substantially similar to the instrument 100 described herein. In some cases, the instrument 100' may be a modified version of the instrument 100. For example, the instrument 100' may not include one or more vent port openings 115.

Figure 3D:
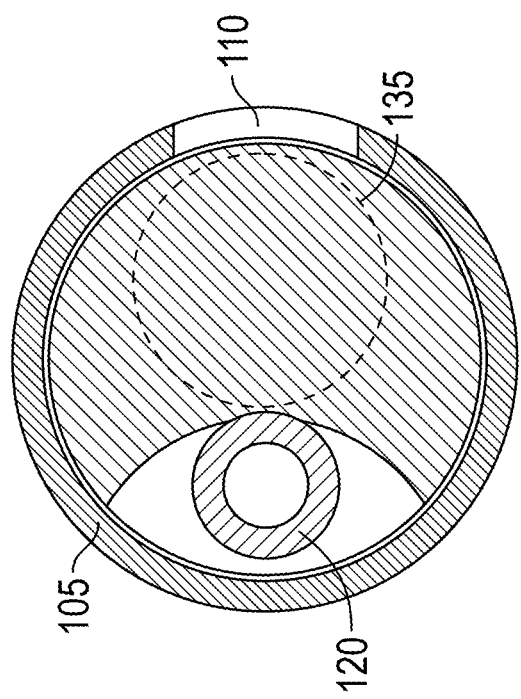
FIG. 3D is a cross-sectional view of the example liquid jet aspiration device of FIG. 3A along line D-D.
Figure 4A:
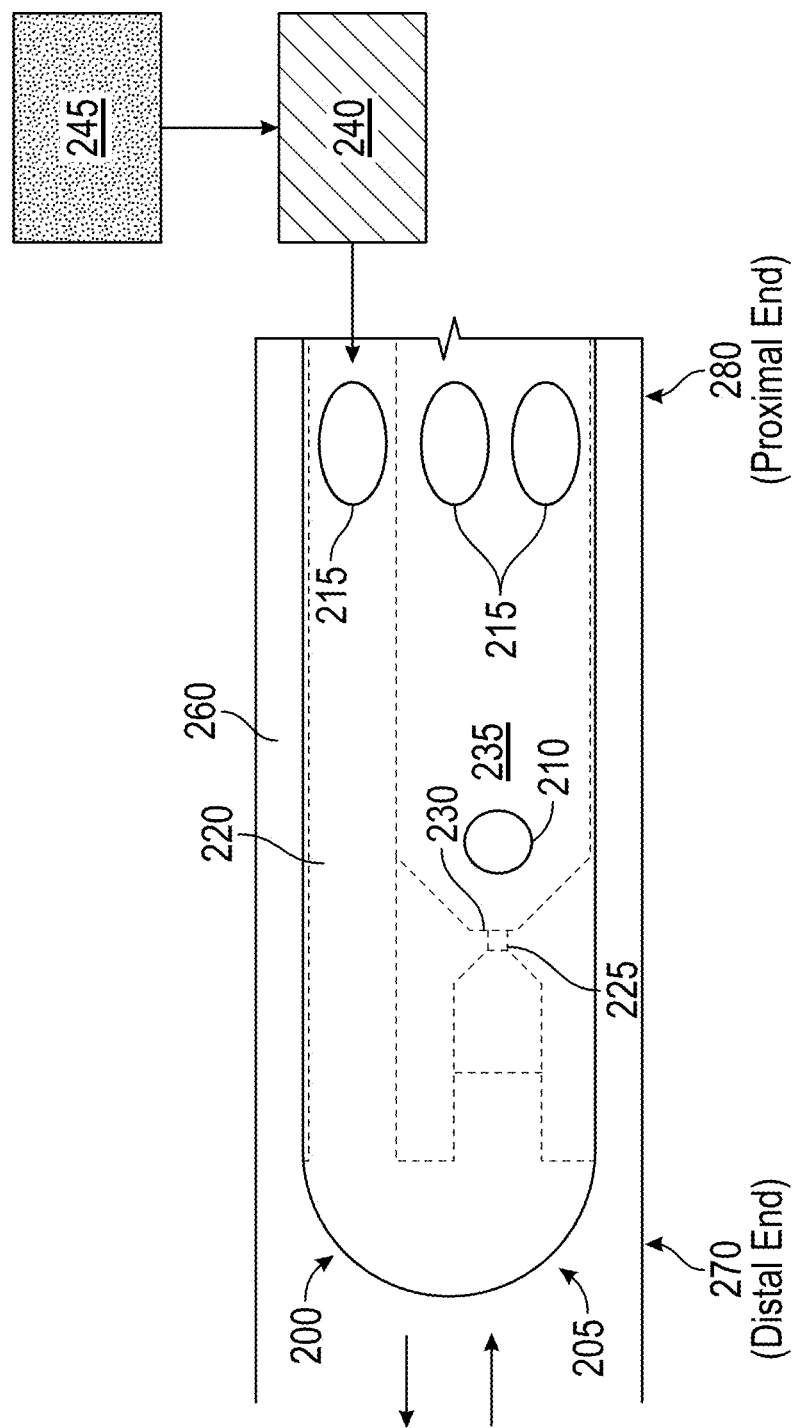
FIG. 4A is a schematic diagram of a distal end of a liquid-jet powered medical instrument movable within a surrounding guide channel or sheath and suitable for use in a surgical procedure at a location internal to a subject.

FIG. 3D illustrates a cross-sectional view of the evacuation tube 105. The aspiration catheters described herein may have any suitable maximum outer diameter and cross-sectional dimension. For example, in some cases, the evacuation catheter can be sized for administration to a subject (e.g., via a ureter or endoscopically via conventionally sized trocars or access catheters). In some cases, the evacuation tube 105 can have an outer diameter greater than or equal to 1 French (Fr), greater than or equal to 2 Fr, greater than or equal to 3 Fr, greater than or equal to 3.6 Fr, greater than or equal to 4 Fr, greater than or equal to 5 Fr, greater than or equal to 6 Fr, greater than or equal to 7, Fr, greater than or equal to 8 Fr, greater than or equal to 9 Fr, greater than or equal to 10 Fr, greater than or equal to 12 Fr, greater than or equal to 14 Fr, greater than or equal to 16 Fr, greater than or equal to 18 Fr, or 20 Fr. In some cases, the evacuation tube has an outer diameter less than or equal to 25 Fr, less than or equal to 18 Fr, less than or equal to 16 Fr, less than or equal to 14 Fr, less than or equal to 12 Fr, less than or equal to 10 Fr, less than or equal to 9 Fr, less than or equal to 8 Fr, less than or equal to 7 Fr, less than or equal to 6 Fr, less than or equal to 5 Fr, less than or equal to 4 Fr, less than or equal to 3.6 Fr, less than or equal to 3 Fr, or less than or equal to 2 Fr. In an example set of cases, the evacuation tube has an outer diameter of greater than or equal to 2 Fr and less than or equal to 4 Fr. Other combinations of ranges are also possible (e.g., greater than or equal to 1 Fr and less than or equal to 20 Fr). Other ranges are also possible.

Turning to FIGS. 4A-4E, the instrument 200 may include a liquid-jet forming aspiration catheter. In some cases, the aspiration catheter can include the evacuation tube 205 including one or more aspiration port openings 210 formed in the side wall of the evacuation tube. In some cases, the evacuation tube 205 can include the liquid supply lumen 220 including the nozzle 225. In some cases, the nozzle 225 may be suitable for forming a liquid jet at the outlet 230 of the liquid supply lumen 220. In some cases, the outlet 230 may be configured and positioned to direct the liquid jet formed by the nozzle 225 into and along the evacuation lumen 235 of the evacuation tube 205. The instrument 200 can include one or more aspiration port openings 210 formed in a side wall of evacuation tube 205. In some cases, the one or more aspiration port openings 210 may be positioned downstream relative to the outlet 230 and/or the nozzle 225. In some cases, the one or more aspiration port openings 210 may be configured and positioned at or near a distal end of the evacuation lumen 235. In some cases, during operation of the instrument 100, a liquid exiting the nozzle 225 can flow past at least a portion of the one or more aspiration port openings 210. Without wishing to be bound by any particular theory, it is believed that such configurations permit creation of a vacuum (e.g., via the Venturi-effect) at the one or more aspiration port openings 210, relative to an environment external to evacuation lumen 235. For example, the pressure within the evacuation lumen 235 at the one or more aspiration port openings 210 may be less than the pressure exterior to the evacuation tube 205. Accordingly, fluid can flow into the one or more aspiration port openings 210 in an attempt to equalize or balance the respective pressures. In some cases, the fluid flow can carry solid deposits along with the fluid thereby aspirating the solid deposits into the evacuation tube 205.

In some cases, the instrument 200 may include one or more vent port openings 215, for example, one or more vent port openings 215 including holes in a sidewall of the evacuation tube 205 providing fluidic communication with the evacuation lumen 235. The one or more vent port openings 215 can be configured and positioned closer a proximal end of the evacuation lumen 235 than the aspiration port openings 210. Those of ordinary skill in the art would understand, based upon the teachings of the specification, that the one or more vent port openings 215 may be configured and positioned at any suitable location of the instrument 200.

Figure 6A:
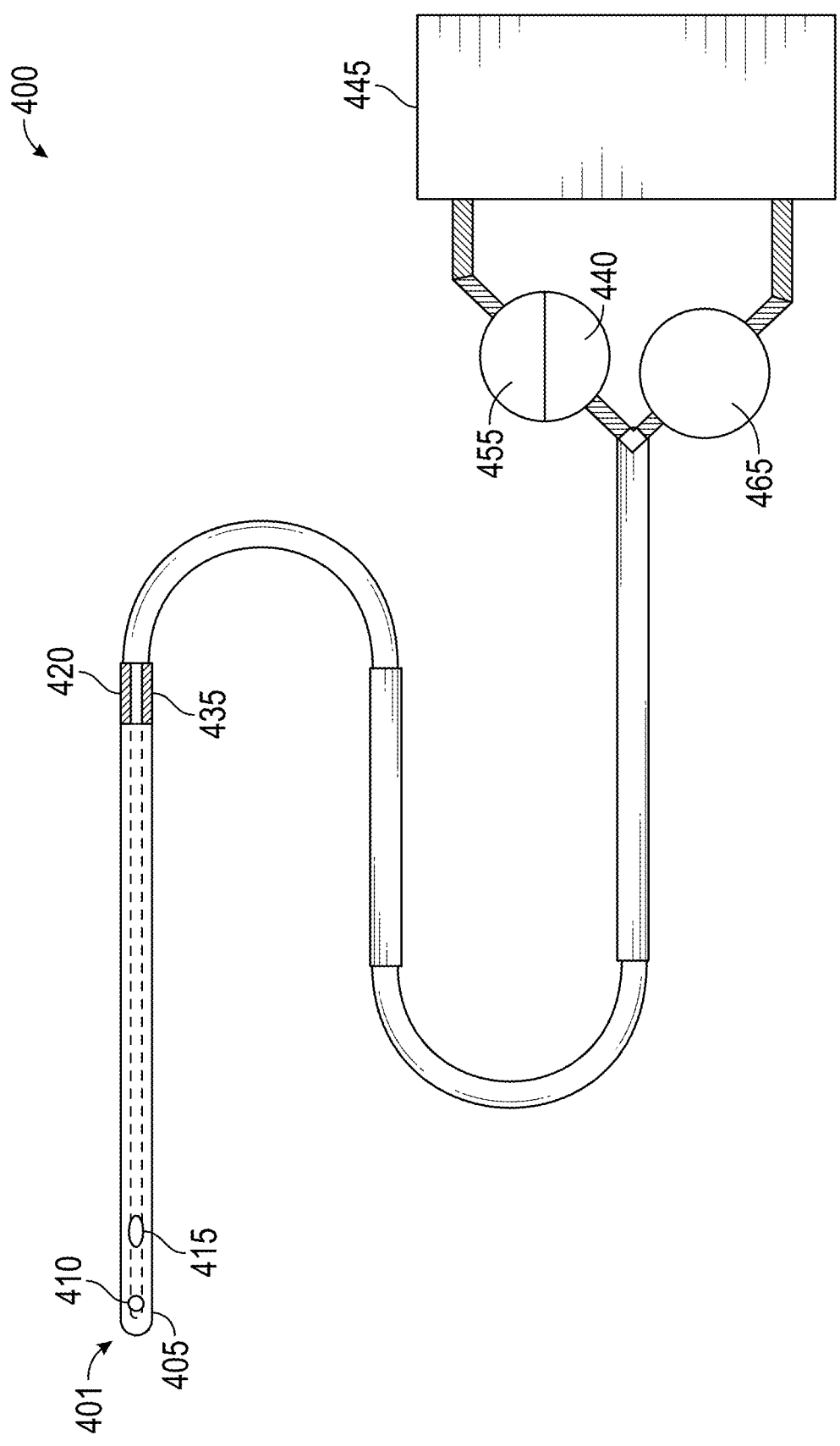
FIG. 6A is a schematic diagram of an example operational system for powering and controlling operation of a liquid-jet powered Venturi-assisted medical aspiration instrument for use at a within an organ or other location internal to a subject.
Figure 6B:
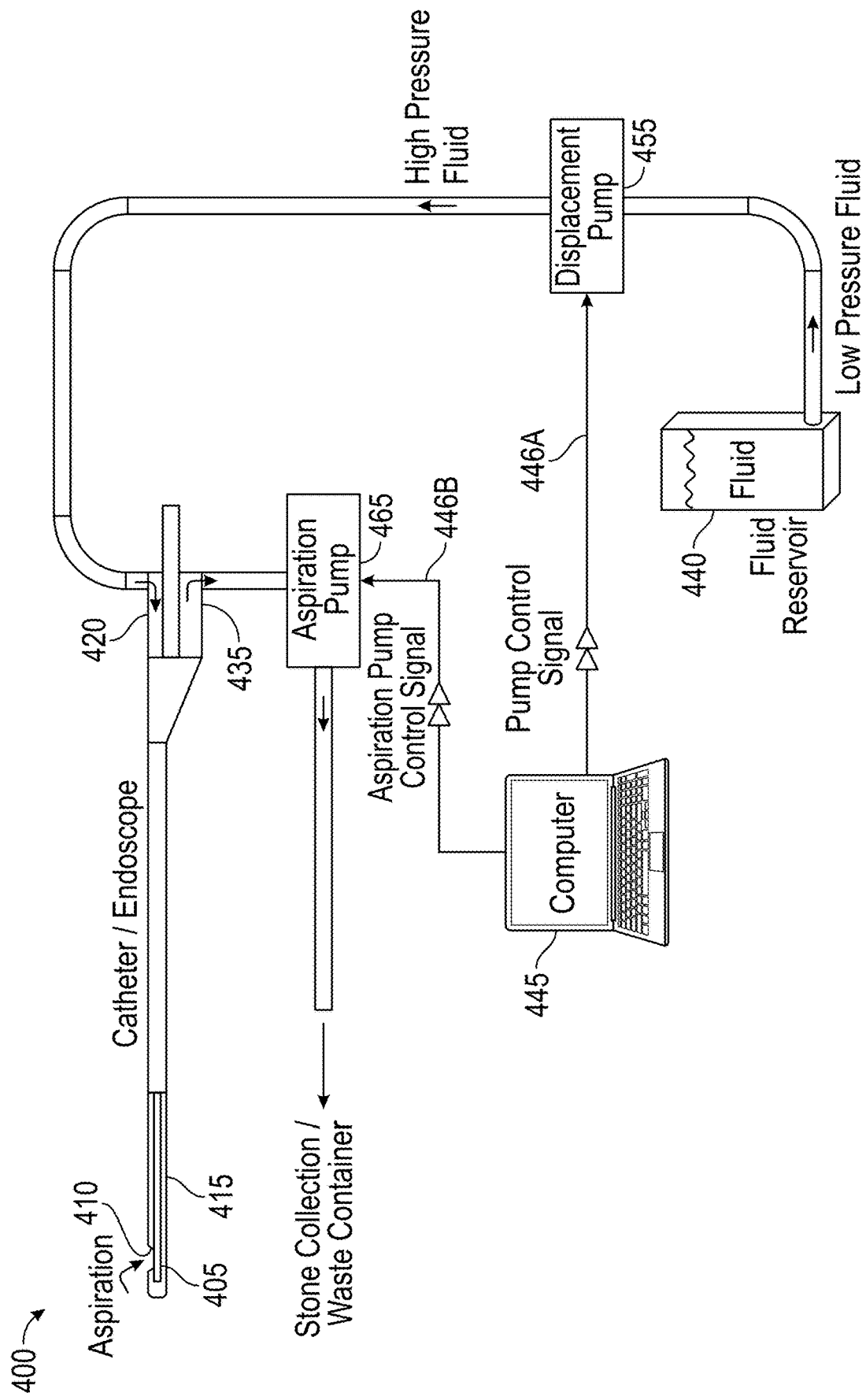
FIGS. 6B-6F are schematic diagrams of various specific and example implementations of the operational system for powering and controlling operation of a liquid-jet powered Venturi-assisted medical aspiration instrument shown in FIG. 6A.

In some cases, the instrument 200 can be an aspiration catheter disposed within an outer sheath 260 (which may in some cases be a lumen of a multilumen trocar or access catheter, such as shown in FIGS. 6A and 6B. In some cases, the instrument 200 may be axially and/or rotationally movable within the outer sheath 260.

In some cases, the outer sheath 260 may be axially and/or rotationally movable with respect to the evacuation tube 205. Such configurations, for example, may enable adjustment of an angular orientation of a distal end 270 of the instrument 200 and exposure of at least one of the one or more aspiration port openings 210 and, optionally, one or more vent port openings 215 to the environment external to the outer sheath 260 when the instrument 100 is in operation. In some cases, the axial movement of the instrument 100, with respect to the sheath 260, may enable an operator to control exposure of the one or more aspiration port openings 210 and/or the one or more vent port openings 215 to the surrounding environment to facilitate different modes of operation. For example, in some cases, an operator, such as a physician, may move the outer sheath 260 relative to the instrument 200 such that at least a portion of, or all of, the one or more vent port openings 215 are closed (e.g., such that no liquid may pass through the one or more vent port openings 215). In some cases, an operator, such as a physician, may move the outer sheath 260 relative to the evacuation tube 205 such that at least a portion of, or all of, the one or more vent port openings 215 are open (e.g., such that liquid may pass through the one or more vent port openings 215).

FIGS. 4B-4E illustrate example ingress and egress flow patterns of an aspiration catheter in response to a position of the outer sheath 260. For example, as illustrated in FIGS. 4B-4E, the one or more vent port openings 215 and/or the aspiration port openings 210 may be selectively opened or closed during operation of the device (e.g., using an outer sheath 260).

Figure 4C:
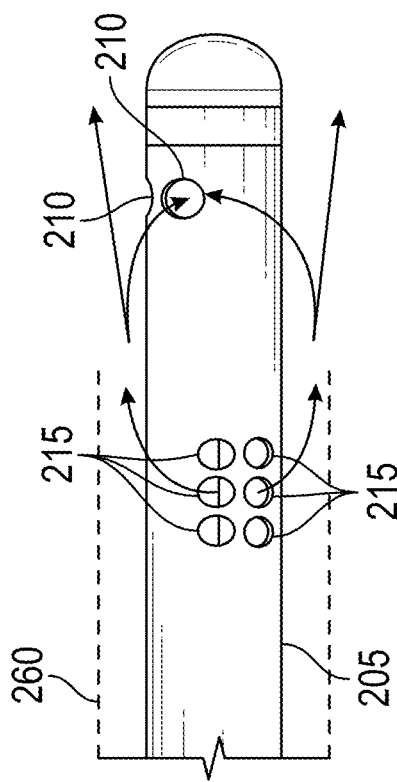
FIG. 4C is an illustration of a liquid-jet powered medical instrument similar to that depicted in FIG. 4A illustrating typical liquid ingress and egress patterns with the surrounding sheath in a first axial position with respect to a distal tip of the instrument.
Figure 4E:
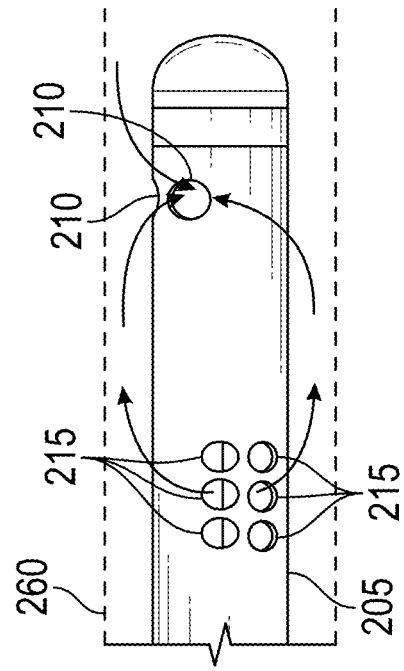
FIG. 4E is an illustration of a liquid-jet powered medical instrument similar to that depicted in FIG. 4A illustrating typical liquid ingress and egress patterns with the surrounding sheath in a third axial position with respect to a distal tip of the instrument.
Figure 4B:
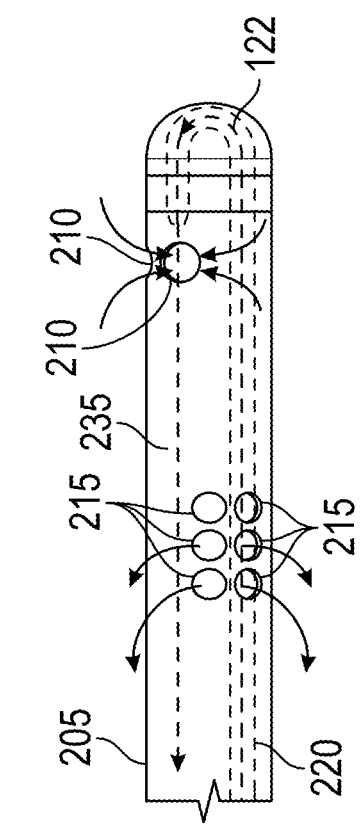
FIG. 4B is an illustration of a liquid-jet powered medical instrument similar to that depicted in FIG. 4A illustrating (arrows) typical liquid ingress and egress patterns with the surrounding sheath removed.

As shown in FIG. 4B, the outer sheath 260 may not be disposed around the aspiration catheter. Accordingly, the one or more vent port openings 215 and the aspiration port openings 210 may be unobstructed. The unobstructed one or more vent port openings 215 and unobstructed one or more aspiration port openings 210 may provide for a fluid flow to pass through the one or more vent port openings 215 and the aspiration port openings 210. As shown in FIG. 4B, the Venturi effect may create a low-pressure zone within the evacuation lumen 235 at the aspiration port openings 210. Accordingly, external liquids (and solid deposits) may ingress into the evacuation lumen 235 via the aspiration port openings 210. In some cases, the liquid from the evacuation lumen 235 can egress from the evacuation lumen 235 to the external environment via the one or more vent port openings 215. As shown in FIG. 4B, the egress of liquid can flow in any direction away from the one or more vent port openings 215. In some cases, pressure can build up within the evacuation lumen 235 downstream from the aspiration port openings 210. Accordingly, the one or more vent port openings 215 can provide an outlet to release pressure downstream of the aspiration port openings 210. In some cases, the vent port openings 215 can allow for increased volumetric flow at the aspiration port openings 215 by providing recirculation. For example, the vent port openings 215 can increase volumetric flow at an aspiration port opening 215 positioned at the distal tip of the evacuation tube 205 as described herein. Without vent port openings 215, a vacuum source such as a peristaltic pump, as described herein, may slow the volumetric flow of fluid pulled by the instrument 200 and/or from an anatomical structure thereby reducing vacuum creation at the distal end of the evacuation tube 205. The vent port openings 215 can also be used to filter fragments and/or debris. In some cases, the vent port openings 215 can prevent the evacuation tube 205 from becoming clogged or obstructing a volumetric fluid flow through the evacuation tube 205. Accordingly, the vent port openings 215 may mitigate the risk of over-pressurization within the anatomical structure.

As shown in FIG. 4C, the outer sheath 260 can be positioned at a first axial position relative to the distal end of the aspiration catheter. In the first axial position, the outer sheath 260 can cover and/or obstruct at least a portion of the one or more vent port openings 215 while the aspiration port openings 210 remain unobstructed. In such cases, a side suction of a liquid can be generated. As shown in FIG. 4C, the Venturi effect may create a low-pressure zone within the evacuation lumen 235 at the aspiration port openings 210. Accordingly, external liquids (and solid deposits) may ingress into the evacuation lumen 235 via the aspiration port openings 210. As further shown in FIG. 4C, the liquid from the evacuation lumen 235 can egress from the evacuation lumen 235 to the external environment via the one or more vent port openings 215. However, due to the outer sheath 260 covering and/or obstructing the one or more vent port openings 215, the liquid flow can flow along the outer sheath 260. In some cases, the liquid can flow laterally toward the distal end of the aspiration catheter and the aspiration port openings 210. At least part of the egressed liquid can remain in the external volume.

Figure 4D:
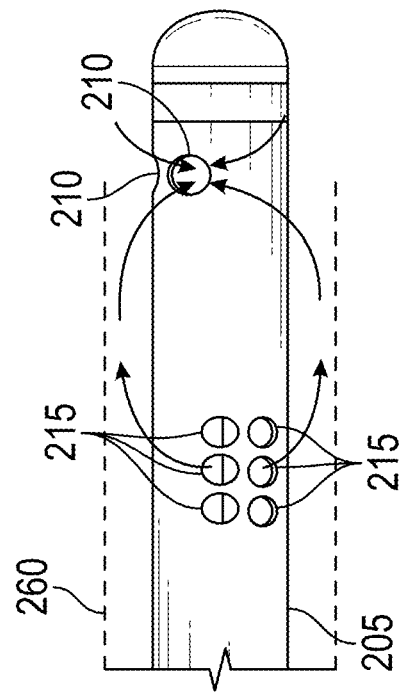
FIG. 4D is an illustration of a liquid-jet powered medical instrument similar to that depicted in FIG. 4A illustrating typical liquid ingress and egress patterns with the surrounding sheath in a second axial position with respect to a distal tip of the instrument.

As shown in FIG. 4D, the outer sheath 260 can be positioned in a second axial position relative to the distal end of the aspiration catheter. In the second axial position, the outer sheath 260 can cover and/or obstruct at least a portion of the one or more vent port openings 215 while the aspiration port openings 210 remain unobstructed. In such cases, a forced irrigation and/or repulsion of a liquid can be generated. As shown in FIG. 4C, the Venturi effect may create a low-pressure zone within the evacuation lumen 235 at the aspiration port openings 210. Accordingly, external liquids (and solid deposits) may ingress into the evacuation lumen 235 via the aspiration port openings 210. As further shown in FIG. 4D, the liquid from the evacuation lumen 235 can egress from the evacuation lumen 235 to the external environment via the one or more vent port openings 215. However, due to the outer sheath 260 covering and/or obstructing the one or more vent port openings 215, the fluid flow can flow along the outer sheath 260. In some cases, the fluid can flow laterally toward the distal end of the aspiration catheter and the aspiration port openings 210. At least part of the egressed liquid can remain in the external volume.

As shown in FIG. 4E, the outer sheath 260 can be positioned in a third axial position relative to the distal end of the aspiration catheter. In the third axial position, the outer sheath 260 can cover and/or obstruct at least a portion of the one or more vent port openings such that a substantially front-oriented (e.g., distal) suction is generated. Sheaths and other mechanisms for controlling flow through the one or more vent port openings 215 and/or aspiration port openings 210 are described in more detail herein.

In some cases, one or more aspiration port openings 110 are positioned downstream relative to a nozzle 225, as illustrated in FIG. 4A. In some cases, the one or more aspiration port openings are configured and positioned at a distal end of evacuation lumen 235. In some cases, during operation of the instrument 100, a liquid exiting the nozzle 225 can flow past at least a portion of the one or more aspiration port openings 110, thereby generating a vacuum at the one or more aspiration port openings, relative to an environment external to evacuation lumen 135. In some cases, each of the one or more aspiration port openings 110 may be characterized by a maximum opening dimension that is less than the minimum cross-sectional dimension of evacuation lumen 135 to ensure that no solid particle is aspirated that is likely to clog the evacuation lumen 135. In specific such cases, each of the one or more aspiration port openings 110 may be characterized by a maximum opening dimension that does not exceed 80% of the minimum cross-sectional dimension of evacuation lumen 135. In some cases, the maximum opening dimension does not exceed about 5%, about 10%, about 15%, about 20%, about 25%, about 30%, about 35%, about 40%, about 45%, about 50%, about 55%, about 60%, about 65%, about 70%, about 75%, or about 80% of the minimum cross-sectional dimension of evacuation lumen 135.

In some cases, the maximum opening dimension is greater than or equal to 5%, greater than or equal to 10%, greater than or equal to 20%, greater than or equal to 30%, greater than or equal to 40%, greater than or equal to 50%, greater than or equal to 60%, or greater than or equal to 70% of the minimum cross-sectional dimension of evacuation lumen 135. In some cases, the maximum opening dimension is less than or equal to 80%, less than or equal to 70%, less than or equal to 60%, less than or equal to 50%, less than or equal to 40%, less than or equal to 30%, less than or equal to 20%, less than or equal to 10%, or less than or equal to 5% of the minimum cross-sectional dimension of evacuation lumen 135.

With reference to FIG. 4A, the instrument 200 includes a nozzle 225 with an outlet 230 disposed within or immediately or in close proximity upstream of an inlet of the lumen of the evacuation lumen 235. In some cases, the outlet 230 may be configured and positioned at or near a distal end 270 of the instrument 200 such that the outlet 230 of the nozzle 225 faces and ejects a liquid jet directed towards a proximal end 280 of the instrument 200. In some cases, one or more aspiration port openings 210 may be positioned closer to the proximal end 280 of the instrument 200 than the outlet 230. The one or more vent port openings 215 can be generally positioned closer to the proximal end 280 of the instrument 100 than the one or more aspiration port openings 210.

In some cases, a portion of the liquid aspirated by the instrument 100 through the one or more aspiration port openings 210 can be ejected from the evacuation lumen 235 of the evacuation tube into a surrounding environment via the one or more vent port openings 215 while the instrument is in operation. In some cases, greater than or equal to 1%, greater than or equal to 5%, greater than or equal to 10%, greater than or equal to 15%, greater than or equal to 20%, greater than or equal to 30%, greater than or equal to 40%, or greater than or equal to 50% of the liquid aspirated by the instrument is ejected from the lumen of the evacuation lumen 235 into a surrounding environment via each of the one or more vent port openings 215 while the instrument 200 is in operation. In some cases, less than or equal to 50%, less than or equal to 40%, less than or equal to 30%, less than or equal to 20%, less than or equal to 15%, less than or equal to 10%, or less than or equal to 5%, or less than or equal to 1%, of the liquid aspirated by the instrument 200 is ejected from the evacuation lumen 235 into a surrounding environment via each of the one or more vent port openings 215 while the instrument 200 is in operation. Combinations of the above-referenced ranges are also possible (e.g., greater than or equal to 1% and less than or equal to 50%). For example, referring again to FIGS. 4B-4E, operational modes which permit liquid ejected into the surrounding environment which is aspirated by the instrument 200 may prevent e.g., excess pressure and/or volume from accumulating within the surrounding organ during operation of the instrument.

In some cases, the instrument is part of an operation and control system (see, for instance, FIGS. 6A-6F) that further includes a controller (e.g., controller 245 of FIG. 4A) configured to operate a liquid source (e.g., liquid source 240 of FIG. 4A) to create pressure and flow conditions for the delivered liquid so that—in combination with adjustment of the relative axial position of the instrument 200 within a surrounding sheath 260 or channel as depicted in FIG. 4B for instruments so configured—the one or more vent port openings 215 ejects at least a portion of the liquid volume supplied by the liquid source 240 from the evacuation lumen 235 of the evacuation tube 205 into the location internal to the subject (e.g., patient). By controlling ingress and egress of liquid in this manner, favorable recirculation flows within the organ (e.g., kidney) for visualization, capture, and retaining solid deposits can be established, and, advantageously, total pressure and liquid volume conditions within the organ or operating space can be balanced and maintained within safe, physiological operational limits. More detailed operational and control systems for this purpose are illustrated in FIGS. 6A-6F and described in more detail herein. For purposes of this disclosure, the terms "capturing" or "retaining" do not require that the biological object and/or solid deposits be physically and fixedly secured to an aspiration port opening. Instead, "capturing" or "retaining" can mean continually attracting the biological objects and/or solid deposits toward the aspiration port opening.

In some cases, during at least some periods during operation, a volume of liquid ejected back into the location internal to the subject (e.g., via the one or more vent port openings 215) can be less than or equal to a volume of the liquid aspirated into evacuation lumen 235 when the system is in operation (e.g., via the one or more aspiration port openings 210). In some cases, a volume of liquid ejected back into the location internal to the subject is greater than or equal to the volume of the liquid aspirated into the evacuation lumen 235 when the system is in operation. In an example set of cases, averaged over the total time of operation of the system, the volume of liquid ejected is substantially the same as the volume of liquid aspirated (e.g., the volume ejected is within less than or equal to 10%, less than or equal to 5%, less than or equal to 2%, or less than or equal to 1% of the volume aspirated).

In some cases, a total flow rate of an aspirated liquid through the one or more aspiration port openings 210 during at least some periods during operation is greater than or equal to a total flow rate of the liquid egress into the operating space through the one or more vent port openings 215. In some cases, during at least some periods during operation a total flow rate of a liquid through the one or more aspiration port openings 210 is greater than or equal to a total flow rate of the liquid through the one or more vent port openings 215. In an example set of cases, integrated over substantial operating times, the total flow rate of liquid ejected is substantially the same as the total flow rate of liquid aspirated (e.g., the total flow rate of liquid ejected via the one or more vent port openings 215 is within less than or equal to 10%, less than or equal to 5%, less than or equal to 2%, or less than or equal to 1% of the total flow rate of the liquid aspirated via the one or more aspiration port openings 210).

In some cases, the controller 245 is configured to operate the liquid source 240 such that a pressure and/or volume of the surrounding liquid during operation of the instrument 200 is regulated, as alluded to herein. For example, in some cases, the controller 245 may be configured to operate the liquid source 240 and other operational parameters such that a pressure and/or volume of the surround liquid during operation of the instrument 200 is within less than or equal to 50% of an initial pressure and/or initial volume of the surrounding liquid. Without wishing to be bound by any particular theory, control over the pressure and/or volume of the liquid source may be useful to ensure patency of the location within the subject, such as the pelvis or calyces of the kidney and/or the ureter (e.g., to ensure the location within the subject does not substantially collapse or expand while the instrument is in operation). In some cases, the controller 245 can be configured to operate the liquid source 240 such that the pressure and/or volume of the surrounding liquid during operation of the instrument 200 is within to 50%, within 40%, within 30%, within 20%, within 10%, or within 5% of an initial pressure and/or initial volume of the surrounding liquid at any point during the operation of the instrument 200. Referring again to the example operational modes in FIG. 4B, e.g., in cases in which the instrument 200 is axially and/or rotationally movable within a surrounding outer sheath 260 or with a guide catheter (e.g., 302 in FIG. 5A), the ingress and/or egress of a liquid through the one or more aspiration port openings 210 and/or the one or more vent port openings 215 may be controlled (e.g., to control volume and/or pressure balance and/or patterns of recirculation of the liquid). In some such cases, control of the ingress and/or egress of liquid through the one or more aspiration port openings 210 and/or the one or more vent port openings 215 may advantageously provide desirable control of liquid pressure, flow, and/or volume balance and/or control of the liquid supply.

As described herein, in some cases, the devices and systems are suitable for use in a surgical procedure e.g., at a location internal to a subject. In some cases, the devices and systems described herein are suitable for use at a location internal to a subject at least partially filled with a surrounding liquid, such that the aspiration port openings 210 and, optionally, the one or more vent port openings 215 are submerged during operation. In some cases, the devices and/or systems described combine any one or more of the Venturi-assisted medical instruments or liquid jet powered aspiration medical instruments disclosed herein and an ablation tool (e.g., a laser, an ultrasound ablation tool (such as, high-intensity focused ultrasound (HIFU) tool) or the like). In some cases, the Venturi-assisted medical instrument or a liquid jet powered aspiration medical instrument disclosed herein, and an ablation tool are on the same instrument.

Figure 5A:
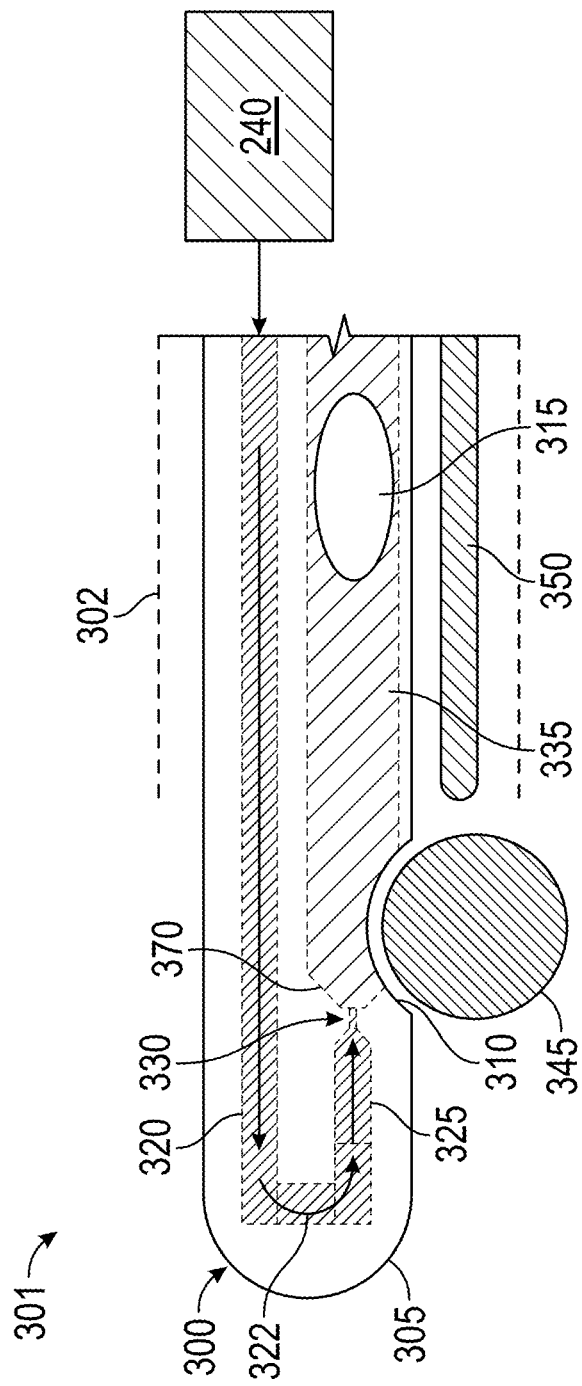
FIG. 5A is a schematic diagram of distal end of an example combination aspiration-ablation system.

FIG. 5A illustrates a system 301 including an ablation system. For example, as illustrated in FIG. 5A, the system 301 can include an aspiration instrument 300, a sheath 302, and an ablation instrument 350. In some cases, the aspiration instrument 300 can be provided via a catheter and can be liquid jet powered. The aspiration instrument 300 can include a nozzle 325 configured and positioned to direct a liquid jet into an evacuation lumen 335 to create a vacuum at an aspiration port opening 310, which is in fluidic communication with the evacuation lumen 335. In some cases, the evacuation lumen 335 can be positioned within and/or in fluidic communication with the sheath 302. The sheath 302 can be a guide catheter or trocar. In some cases, the sheath 302 can in fluid communication with one or more fluid sources. For example, the sheath 302 may be in fluid communication with a liquid source 340. The liquid source 340 can also be referred to as a liquid supply or a liquid reservoir. In some cases, a liquid reservoir can be a body or housing defining a volume to contain a liquid body. Additionally or alternatively, the liquid source 340 can be referred to as a fluid source, a fluid supply, and/or a fluid reservoir. In some cases, the sheath 302 can be in fluid communication with a vacuum source. For example, the sheath 302 may be configured to apply an external vacuum (e.g., a suction force beyond that created by the aspiration resulting from the liquid jet) to the evacuation lumen 335. In other cases of this or any other Venturi-assisted medical instrument or a liquid jet powered aspiration medical instrument disclosed herein, an evacuation lumen 335 may be connected with its proximal end in fluidic communication with an external vacuum to supplemental or assist or replace aspiration created by liquid jet aspiration. In some cases, the one or more aspiration port openings 310 can be selectively sized and shaped to retain and immobilize a solid deposit 345 of predetermined size and shape within the enclosed location of the subject (e.g., a kidney stone of measured size).

In some cases, an ablation instrument 350 can form part of, or is functionally and structurally integrated with, aspiration instrument 300. In some cases, the ablation instrument 350 can include an ablation device that is movable with respect to the aspiration instrument 300. Such configurations may be useful, for example, to enable an operator of the system to position the ablation device in proximity with the one or more aspiration port openings 310 (holding a solid deposit 345, for example) to pulverize the solid deposit 345. In some cases, the ablation instrument 350 can be operably linked to the aspiration instrument 300 (e.g., the aspiration instrument 300 and the ablation instrument 350 can be mechanically coupled to a common component, e.g., the sheath 302 as illustrated and/or a guide catheter/trocar). In some cases, aspiration instrument 300 and ablation instrument 350 can be separate instruments.

In some cases, the evacuation lumen 335 can include one or more aspiration port openings 310 and/or one or more vent port openings 315. In some cases, the one or more aspiration port openings 310 can be positioned at or near a distal end 370 of evacuation lumen 335. The one or more vent port openings 315 can be configured and positioned proximal to the aspiration port openings 310 on the evacuation tube 305.

Figure 5B:
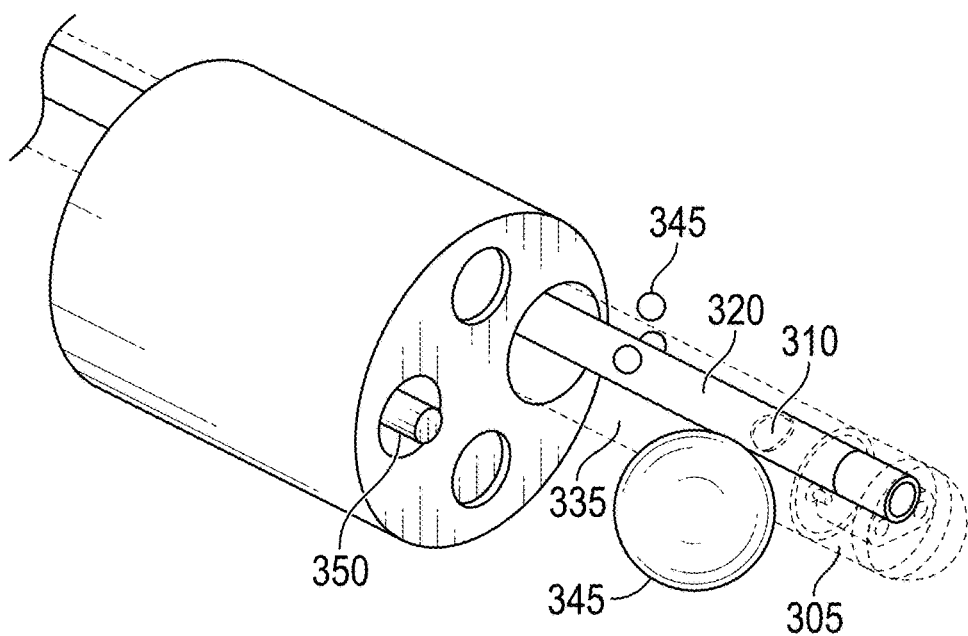
FIGS. 5B and 5C are depictions of a combination aspiration-ablation system similar to that depicted schematically in FIG. 5A, but as deployed with a multi-lumen access catheter or access catheter containing a multi-lumen guide insert (as illustrated), having guide channels for the aspiration catheter (immobilizing a kidney stone as illustrated) and an ablation tool.
Figure 5C:
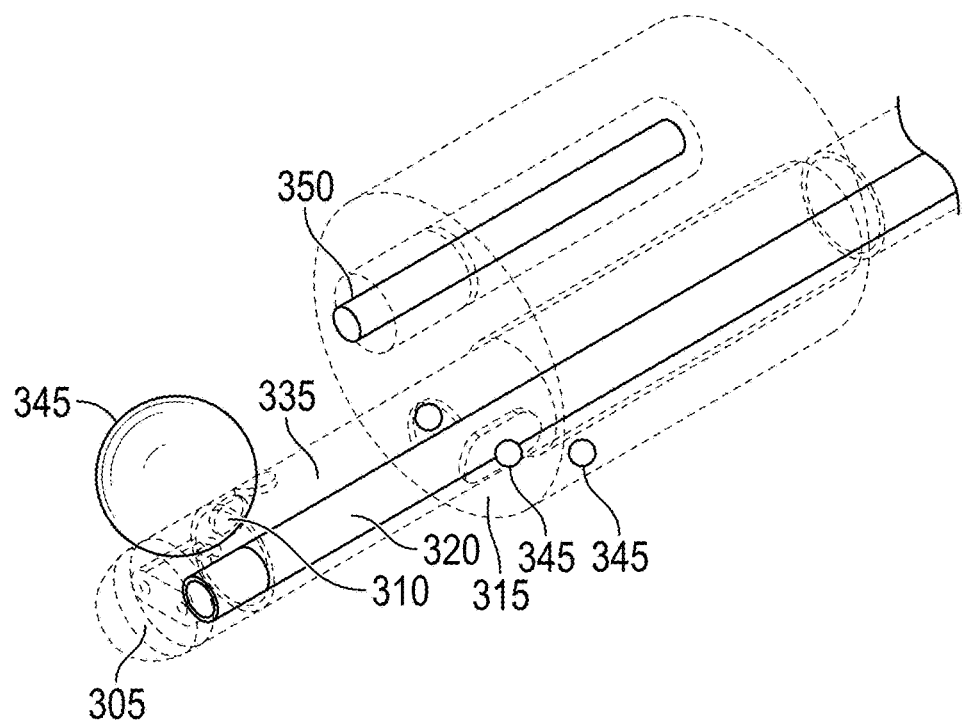

Other configurations are also possible. In some cases, the system can be a multi-lumen system. FIGS. 5B and 5C show example configurations of a multi-lumen system, as descried herein. For example, in some cases, the system can include a liquid supply lumen 320 disposed within an evacuation tube 305. Additionally, or alternatively, in some cases, the system can include a dual lumen sheath. In some cases, the dual lumen sheath can include a first lumen including a movable liquid jet powered aspiration instrument and a second lumen including a movable ablation instrument 350. The aspiration instrument may be any suitable aspiration instrument known to the skilled artisan, including, but not limited to the aspiration devices of the present disclosure. For example, the aspiration instrument can be an evacuation tube 305. In some cases, the instrument can include a dual lumen evacuation tube 305 with a first lumen including evacuation lumen 335 of FIG. 5A and a second lumen including an ablation instrument (e.g., laser, ultrasonic instrument, electrohydraulic instrument, pneumatic instrument, cryo, RF, waterjet, morcellation blades, etc., such as ablation instrument 350 of FIG. 5A). In some cases, the ablation instrument can include a laser.

FIG. 6A shows a case of a system 400 including a liquid jet powered aspiration instrument 401 including a liquid supply lumen 420 configured to receive and transport a pressurized liquid to a nozzle positioned at an end of the liquid supply lumen 420 when connected to a liquid source 440. In some cases, the aspiration instrument 401 can include an evacuation tube 405 including an evacuation lumen 435. The liquid supply lumen 420 can be configured to output a liquid jet into the evacuation lumen 435. As described herein, the pressure can be inversely proportional to the velocity of the fluid. The evacuation lumen 435 can contain a high flow rate. For example, as described above the liquid jet can have a high flow rate between about 20 mL/min and 60 mL/min, which may cause formation of low pressure. In some cases, the evacuation tube 405 can further include one or more aspiration port openings 410 in the form of one or more openings in the sidewall of the evacuation tube 405. In some cases, the evacuation tube 405 can be configured so that liquid ejected from a nozzle is directed past one or more aspiration port openings 410 to generate a Venturi-created or Venturi-assisted vacuum. For example, the pressure difference between the environment and the low pressure resulting from the flow of the liquid jet can result in a relative negative pressure or suction through the one or more aspiration port openings 410. The Venturi-created or Venturi-assisted vacuum can be a first vacuum level. Accordingly, the liquid jet can create a negative pressure at the distal end of the evacuation lumen 435. In some cases, the first vacuum level is sufficient for capturing a biological object, such as a solid deposit, within the one or more aspiration port openings 410 at the location internal to the subject when the aspiration instrument 401 is in operation. In some cases, the aspiration instrument 401 can further include one or more vent port openings 415 in the side wall of the evacuation tube 405. The one or more vent port openings 415 can be positioned downstream of the one or more aspiration port opening 410 and can be configured to eject at least a portion of liquid flowing along evacuation lumen 435.

In some cases, the system 400 can further include a high-pressure fluidic pump 455 configured to pump a liquid from the liquid source 440 into the liquid supply lumen 420. In some cases, a vacuum source 465 can be connected at a proximal end of evacuation lumen 435. The vacuum source 465 can be configured to assist aspiration from the evacuation lumen 435 by pumping fluid from the evacuation lumen 435 into a waste container. The vacuum source 465 can generate a second vacuum level. For example, the vacuum source 465 can create negative pressure at the proximal end of the evacuation lumen 435. In some cases, the second vacuum level can be less than the second vacuum level. For example, the second vacuum level generated by the vacuum source 465 may be result in a fluid flow rate slower than the flow rate of the liquid jet. For example, the second vacuum level may cause a fluid flow rate between about 0 mL/min and 150 mL/min. In some cases, the second vacuum level may cause a nominal fluid flow rate of about 70 mL/min. Accordingly, the vacuum source 465 can act as a flow regulator to regulate fluid flow through the evacuation lumen 435 and to counteract the higher vacuum level created by the flow of the liquid jet. In some examples, another flow regulator for regulating fluid flow through the evacuation lumen 435 can be used in addition to or instead of the vacuum source 465. For example, a valve can be utilized.

A controller 445 can be programmed and configured to operate the high-pressure fluidic pump 455 and/or the vacuum source 465. In some cases, the controller 445 can be used to ensure the pressure and/or volume of the location internal to the subject remains substantially constant during operation of the system 400. In some cases, the system 400 can further include a peristaltic pump connected at a proximal end of the evacuation lumen 435. A peristaltic pump can include a pinch-and-roll mechanism to create negative pressure or suction at an inlet. In some cases, the controller 445 can be programmed and configured to operate the high-pressure fluidic pump 455 and the optional peristaltic pump, when present, such that the pressure and/or volume of the location internal to the subject remains substantially constant during operation of the system 400. In some cases, the vacuum source 465 and the peristaltic pump may be operated simultaneously in parallel or in series. In some examples, the controller 445 can be configured to control a flow regulator (such as, a valve) for regulating fluid flow through the evacuation lumen 435. In some cases, the controller 445 can be configured to control the high-pressure fluidic pump 455 and the vacuum source 465 independently.

Internal pressure within the aspiration instrument 401 can be regulated and/or controlled by the fluidic pump 455 and the vacuum source 465. In some cases, the fluidic pump 455 and the vacuum source 465 can be matched 1:1. For example, the controller 445 can be configured to operate the fluidic pump 455 and the vacuum source 465 simultaneously to regulate and control pressure within the aspiration instrument 401.

FIGS. 6B-6F show example systems with various open loop and closed loop control systems. Although some examples describe one or more sensors positioned proximally of the aspiration instrument 401, the one or more sensors may also be disposed within the aspiration instrument 401, positioned at a distal end of the aspiration instrument 401, between the distal end and the proximal end of the aspiration instrument 401. In some cases, one or more sensors can be positioned within an evacuation tube 405. In some cases, one or more sensors can be positioned within an evacuation lumen 435. The one or more sensors can be configured to monitor pressure and/or temperatures within the system 400.

FIG. 6B shows an example implementation of the system 400 including at least an open loop control of one or more pumps. In some cases, the one or more pumps can include a displacement pump and/or an aspiration pump. For example, the system 400 can include a high-pressure fluidic pump 455 and a vacuum source 465. The controller 445 can be in electrical communication with the one or more pumps. For example, as shown in FIG. 6B, the controller 445 can be configured to transmit a first control signal 446A to the high-pressure fluidic pump 455 and a second control signal 446B to the vacuum source 465. In such cases, the first control signal 446A can control the fluid flow of the liquid from the liquid source 440 toward to evacuation tube 405 and the second control signal 446B can control the aspiration assistance from the vacuum source 465. In some examples, a flow regulator can be used in addition to or in place of the vacuum source 465, as described herein. As further shown in FIG. 6B, the controller 445 can be configured to operate without receiving a feedback signal. Open loop control can operate without requiring feedback from sensors. Accordingly, the system can implement a simple control system without sensors thereby reducing costs. The open loop control can also passively control fluid flow through the system without actively changing flow rates based on sensed or measured values.

Figure 6C:
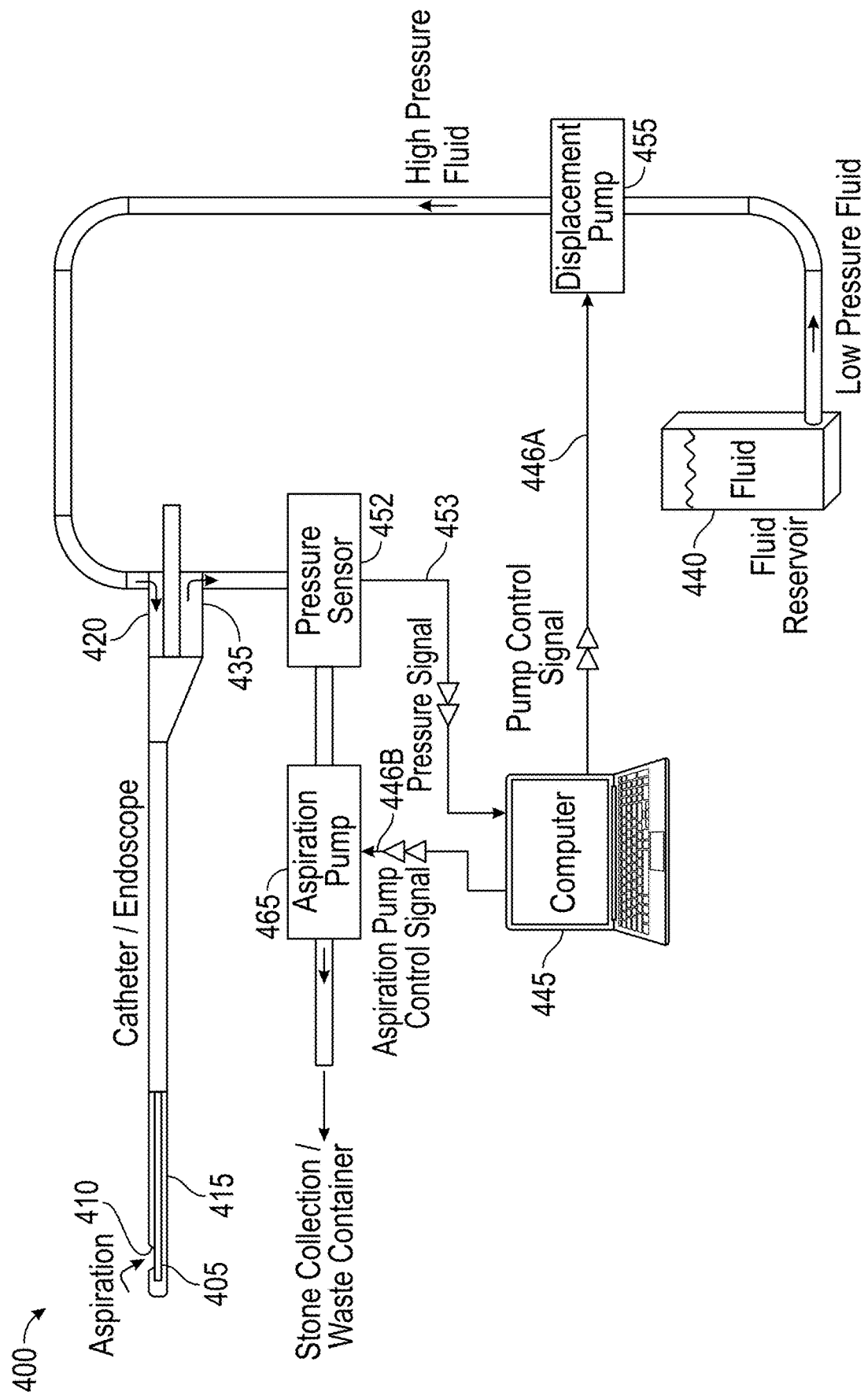

FIG. 6C shows an example implementation of the system 400 including at least an open loop control of a first set of one or more pumps and a closed loop control of a second set of one or more pumps. In some cases, the first set of one or more pumps can include a displacement pump. For example, the first set of one or more pumps can include a high-pressure fluidic pump 455. In some cases, the second set of one or more pumps can include an aspiration pump. For example, the second set of one or more pumps can include a vacuum source 465. The controller 445 can be in electrical communication with the first set of one or more pumps and the second set of one or more pumps. For example, as shown in FIG. 6C, the controller 445 can be configured to transmit a first control signal 446A to the high-pressure fluidic pump 455 and a second control signal 446B to the vacuum source 465. In some examples, a flow regulator can be used in addition to or in place of the vacuum source 465, as described herein. In some cases, the system 400 can further include one or more sensors. For example, the system 400 can include a pressure sensor 452. The pressure sensor can be configured to monitor the pressure at the aspiration port openings 410 and/or to detect occlusions within the evacuation lumen 435. The controller 445 can be in electrical communication with the one or more sensors. In some cases, the one or more sensors can be configured to provide a feedback signal 453 to the controller 445. For example, the pressure sensor 452 can provide the controller 445 with a pressure signal in the evacuation lumen 435. The controller 445 can adjust one or more control signals based on the feedback. Accordingly, the system 400 can provide an open loop control of the high-pressure fluidic pump 455 with inline pressure monitoring for a closed loop control of the vacuum source 465 (and/or a flow regulator). As discussed herein, open loop control can operate without requiring feedback from sensors thereby reducing costs.

Figure 6D:
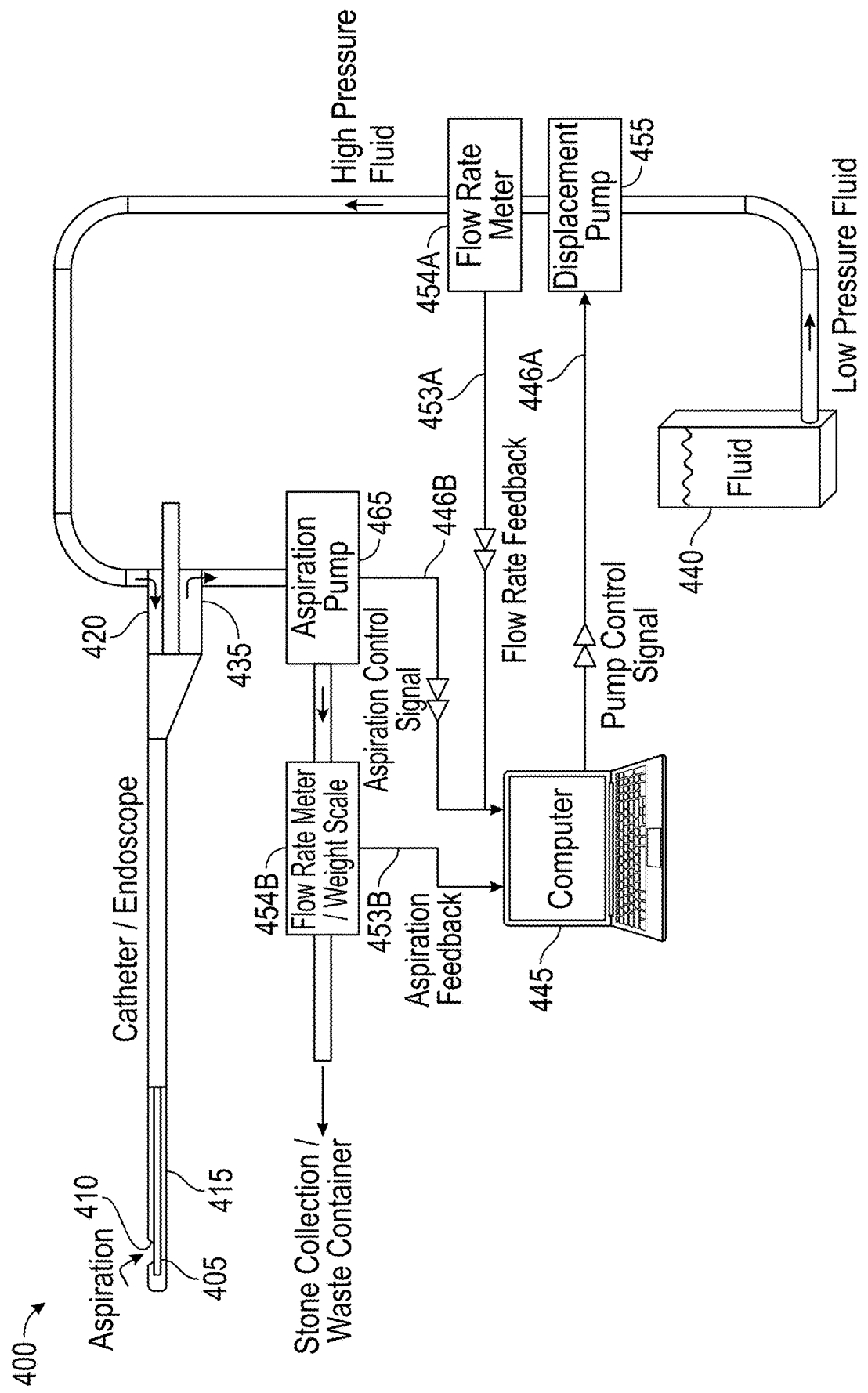

FIG. 6D shows an example implementation of system 400 including at least a closed loop control of one or more pumps. In some cases, the one or more pumps can include a displacement pump and an aspiration pump. For example, the one or more pumps can include a high-pressure fluidic pump 455 and a vacuum source 465. In some examples, a flow regulator can be used in addition to or in place of the vacuum source 465, as described herein. The controller 445 can be in electrical communication with the one or more pumps. For example, the controller 445 can be configured to transmit a first control signal 446A to the high-pressure fluidic pump 455 and a second control signal 446B to the vacuum source 465 (and/or a flow regulator). In some cases, the system 400 can further include one or more sensors. For example, as shown in FIG. 6D, the system 400 can include a first flow rate meter 454A and a second flow rate meter 454B. The first flow rate meter 454A can be configured to measure a flow rate within the liquid supply lumen 420. The second flow rate meter 454B can be configured to measure a flow rate within the evacuation lumen 435. The controller 445 can be in electrical communication with the one or more sensors. In some cases, the one or more sensors can be configured to provide a feedback signal to the controller 445. For example, the first flow rate meter 454A can be configured to provide a first feedback signal 453A to the controller 445 and the second flow rate meter 454B can be configured to provide a second feedback signal 453B to the controller 445. The controller 445 can adjust one or more control signals based on the feedback. Accordingly, the system 400 can provide a closed loop control of the high-pressure fluidic pump 455 and the vacuum source 465 (and/or a flow regulator) via flow rate feedback. Closed loop control can increase accuracy of fluid flow by actively reacting to sensed or measured values. Additionally, the system can react to unexpected events detected by sensors.

Figure 6E:
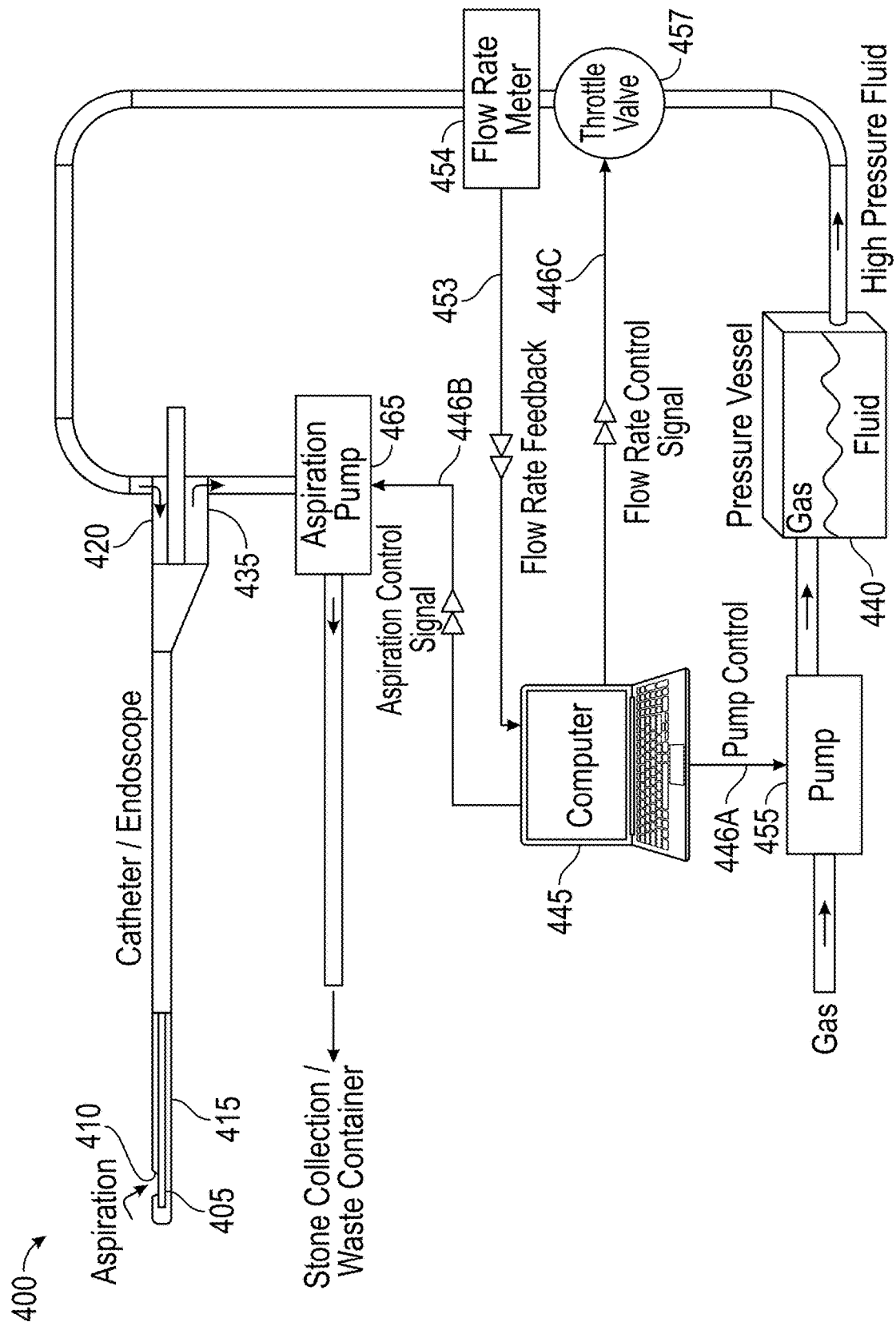

FIG. 6E shows an example implementation of system 400 including at least an open loop control of one or more pumps. In some cases, the one or more pumps can include a displacement pump and an aspiration pump. For example, the one or more pumps can include a high-pressure fluidic pump 455 and a vacuum source 465. In some examples, a flow regulator can be used in addition to or in place of the vacuum source 465, as described herein. The controller 445 can be in electrical communication with the one or more pumps. For example, the controller 445 can be configured to transmit a first control signal 446A to the high-pressure fluidic pump 455 and a second control signal 446B to the vacuum source 465 (and/or a flow regulator). In some cases, the system 400 can further include one or more valves. For example, the system 400 may include a throttle valve 457. The controller 445 can be in electrical communication with the one or more valves. For example, the controller 445 may be configured to transmit a third control signal 446C to the throttle valve 447. In some cases, the system 400 can further include one or more sensors. For example, as shown in FIG. 6E, the system 400 can include a flow rate meter 454. The flow rate meter 454 can be configured to measure a flow rate within the liquid supply lumen 420. The controller 445 can be in electrical communication with the one or more sensors. In some cases, the one or more sensors can be configured to provide a feedback signal to the controller 445. For example, the flow rate meter 454 can be configured to provide a feedback signal 453 to the controller 445. The controller 445 can adjust one or more control signals based on the feedback. Accordingly, the system 400 can provide an open loop control of the vacuum source 465 with inline fluid flow monitoring for a closed loop control of the high-pressure fluidic pump 455 and/or the throttle valve 457. Hybrid loop control implement both open loop and closed loop control. Select parts of the system may not include sensors or feedback from sensors to actively control various actuators while other select components of the system may receive feedback from sensors to actively control other various actuators. A hybrid loop control can include the advantages of both open loop and closed loop by providing accurate control to sensitive components while reducing costs.

Figure 6F:
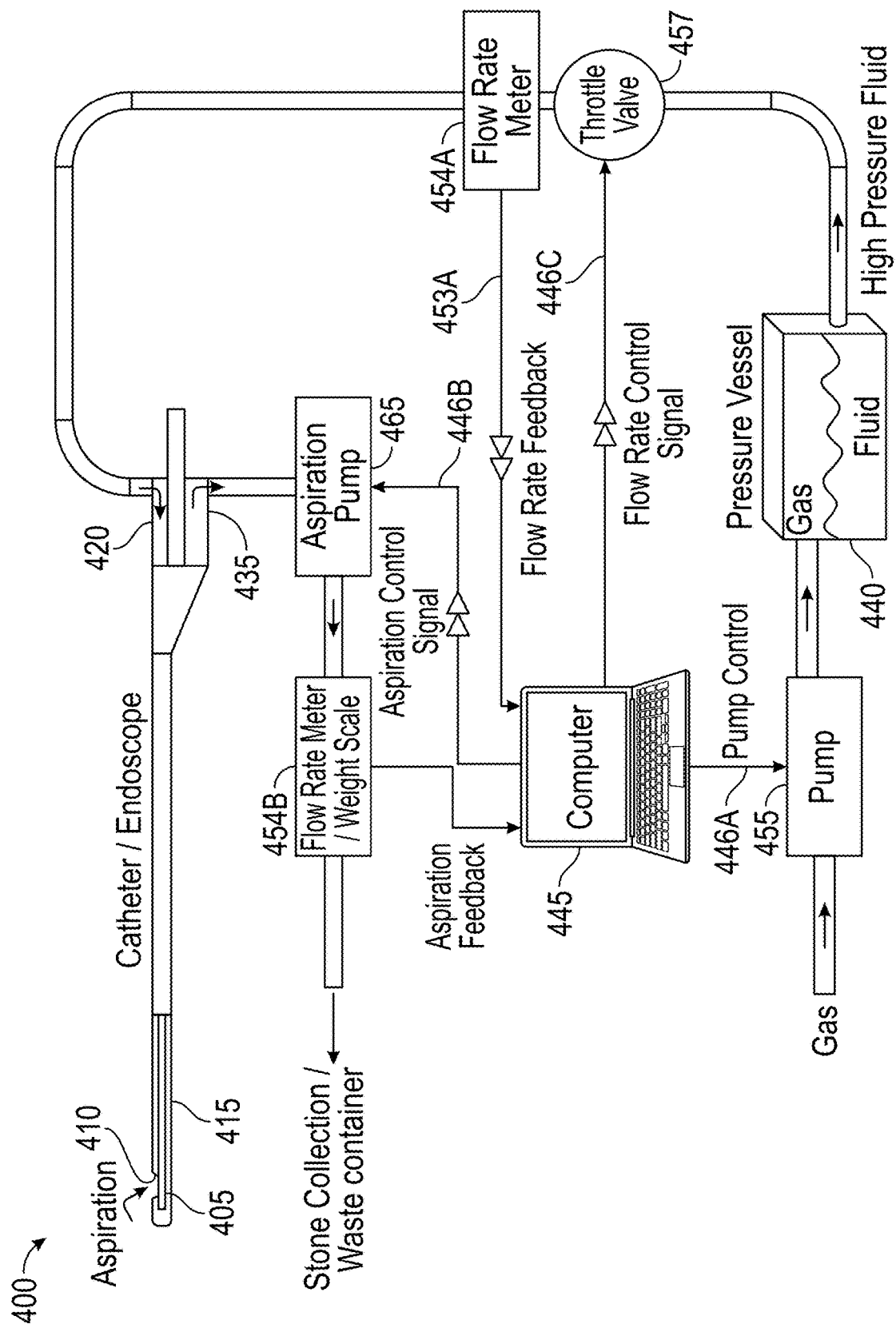

FIG. 6F shows an example implementation of system 400 including at least closed loop feedback control of one or more pumps and a pressure vessel. In some cases, the one or more pumps can include a displacement pump and an aspiration pump. For example, the one or more pumps can include a high-pressure fluidic pump 455 and a vacuum source 465. In some examples, a flow regulator can be used in addition to or in place of the vacuum source 465, as described herein. The controller 445 can be in electrical communication with the one or more pumps. For example, the controller 445 can be configured to transmit a first control signal 446A to the high-pressure fluidic pump 455 and a second control signal 446B to the vacuum source 465 (and/or a flow regulator). In some cases, the system 400 can further include one or more valves. For example, the system 400 may include a throttle valve 457. The controller 445 can be in electrical communication with the one or more valves. For example, the controller 445 may be configured to transmit a third control signal 446C to the throttle valve 447. In some cases, the system 400 can further include one or more sensors. For example, as shown in FIG. 6F, the system 400 can include a first flow rate meter 454A and a second flow rate meter 454B. The first flow rate meter 454A can be configured to measure a flow rate within the liquid supply lumen 420. The second flow rate meter 454B can be configured to measure a flow rate within the evacuation lumen 435. The controller 445 can be in electrical communication with the one or more sensors. In some cases, the one or more sensors can be configured to provide a feedback signal to the controller 445. For example, the first flow rate meter 454A can be configured to provide a first feedback signal 453A to the controller 445 and the second flow rate meter 454B can be configured to provide a second feedback signal 453B to the controller 445. The controller 445 can adjust one or more control signals based on the feedback. Accordingly, the system 400 can provide a closed loop control of the high-pressure fluidic pump 455 and the vacuum source 465 (and/or a flow regulator) via flow rate feedback and can provide open loop control of the throttle valve 457. As discussed herein, hybrid loop control can include the advantages of both open loop and closed loop by providing accurate control to sensitive components while reducing costs.

Other combinations of these features and/or other configurations are also possible. Those of ordinary skill in the art would be capable of selecting suitable open loop control systems, closed loop control systems, flow rate feedback systems, pumps, pressure vessels, and the like based upon the teachings of this specification.

Figure 7:
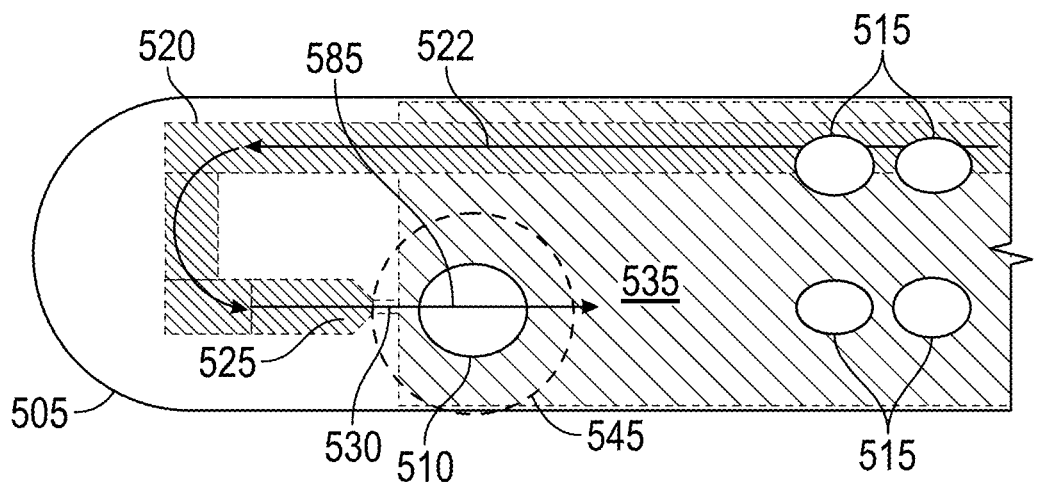
FIG. 7 is a schematic diagram of a distal end of an example liquid-jet powered Venturi-assisted medical aspiration instrument with one or more aspiration port opening sized to retain an immobilize solid deposits of interest.

Aspects of the disclosure further relate to methods of using the devices disclosed herein. FIG. 7 illustrates a distal end of an evacuation tube 505, which can be similar to the evacuation tubes 105 or 205 or any of the evacuation tubes described herein except for the differences described herein. In some cases, the methods relate to capturing a biological object such as a solid deposit 545 (e.g., a kidney stone) at a location internal to a subject (e.g., a kidney), for example, using any of the devices disclosed herein. For example, as shown in FIG. 7 the methods can include forming a liquid jet 585 with a nozzle 525 and directing the liquid jet 585 from an outlet 530 into the evacuation lumen 535 of the evacuation tube 505 and proximate to the one or more aspiration port openings 510 in a side wall of the evacuation lumen 535 of the evacuation tube 505 at the one or more aspiration port openings 510.

Venturi-created or Venturi-assisted vacuum, as described herein, is created because passing a liquid (e.g., physiological liquids such as water or saline), through a constriction (e.g., a nozzle) increases the velocity of the physiological fluid in, accordance with the principle of mass continuity, which is balanced by a drop in the static pressure, in accordance with the conservation of mechanical energy (e.g., Bernoulli's principle). As shown illustratively in FIG. 3C, this process reduces, in some cases, the pressure inside the evacuation lumen, relative to pressure of an environment outside of the device (e.g., the pelvis or calyces of the kidney), resulting in a vacuum proximate the one or more aspiration port openings.

In some cases, the Venturi-created or Venturi-assisted vacuum produces a suction force of greater than or equal to 50 mmHg and less than or equal to 600 mmHg. In some cases, the vacuum generated produces a suction force is greater than or equal to 50 mmHg, greater than or equal to 100 mmHg, greater than or equal to 200 mmHg, greater than or equal to 300 mmHg, greater than or equal to 400 mmHg, greater than or equal to 500 mmHg, or greater than or equal to 600 mmHg. In some cases, the suction force is less than or equal to 600 mmHg, less than or equal to 500 mmHg, less than or equal to 400 mmHg, less than or equal to 300 mmHg, less than or equal to 200 mmHg, less than or equal to 100 mmHg, or less than or equal to 50 mmHg. The desired suction force can be determined by balancing various factors including the requisite force to aspirate a biological object and safety to the patient. In some cases, the suction force can be selected to balance adequately aspirating biological objects, such as urinary calculi, without injuring or causing damage to the surrounding tissue. For example, the suction force may be sufficiently strong to pull loose debris and fragments of a urinary calculus toward an aspiration port opening but not so strong as to aspirate the surrounding tissue and/or mucosal wall.

In some cases, the methods can include balancing the suction force with the internal pressure at the location internal to the subject, for example, to ensure that the location internal to the subject (such as, an organ) does not collapse on itself during operation of the device. As such, in some cases, the methods include operating the device such that the pressure within the location internal to the subject is maintained within 10% (e.g., within 5%, within 1%) of an initial pressure at the location internal to the subject, while the device is in operation.

In some cases, the methods can further include capturing and retaining the biological object such as a solid deposit 545 at the one or more aspiration port openings 510. The biological object may be any suitable biological object capable of being captured using the Venturi-created or Venturi-assisted vacuum disclosed herein. For example, in some cases, the biological object is a solid deposit 545 such as a stone known to form in the kidneys, bladder, prostate gland, gallbladder, salivary glands, and pancreas (e.g., kidney stone, bladder stone, prostatic calculi, gallstones, salivary stones, biliary stones, pancreatic stones). The Venturi-created or Venturi-assisted vacuum can be used to attract the biological object toward an aspiration port opening 510. The aspiration port opening 510 can be configured to receive the biological object through the aspiration port opening, if the biological object is smaller than the aspiration port opening. The aspiration port opening 510 can capture and retain the biological object by continually attracting the biological object toward the aspiration port opening 510 if the biological object is larger than the aspiration port opening 510. In some cases, the biological object may be fixedly secured to the aspiration port opening 510 via aspiration. Other biological objects may also be captured using the Venturi-assisted and Venturi-created vacuums disclosed herein, for example, blood clots, tissue samples (e.g., such as those obtained by biopsy), tissue debris, cellular debris (e.g., endometrial cells, prostate cells), necrotic tissue, mucous, pleghym, cysts, emboli, bone marrow, fetal cells, eggs, and portions and/or components thereof. In some cases, the biological object is the byproduct of a procedure (e.g., procedures that use ablation techniques/tools) such as cardiac procedures (e.g., ablation of heart tissue), pulmonary procedures (e.g., ablation of tumors), liver procedures (e.g., ablation of tumors), kidney procedures (e.g., ablation of tumors), endometrial ablation procedures, prostate ablation procedures, brain tumor ablation procedures, or gastrointestinal procedures (e.g., polyp removal). Other types of biological objects are also possible.

In some cases, the methods also include venting into the location internal to the subject, a selectable fraction of a total volumetric flow rate of liquid aspirated by the Venturi-created or Venturi-assisted vacuum. In some cases, the fraction of the total volumetric flow rate of liquid aspirated by the Venturi-created or venture-assisted vacuum that is vented is selected to maintain the pressure and/or volume within the location internal to the subject remains substantially constant, as described herein.

In some cases, a vented liquid exits the evacuation lumen 535 into the location surrounding the evacuation tube 505 through the one or more vent port openings 515 in a side wall of the evacuation lumen 535 of the evacuation tube 505 that is located downstream of the one or more aspiration port openings 510.

In some cases, the methods further include removing the biological object such as a solid deposit 545 at a location internal to a subject, for example, using the one or more devices disclosed herein. In some cases, the methods include forming a liquid jet 585 with the nozzle 525 and directing liquid jet 585 into the evacuation lumen 535 of the evacuation tube 505 and proximate the one or more aspiration port openings 510 in a side wall of the evacuation lumen 535 in the evacuation tube 505 to generate a Venturi-created or Venturi-assisted vacuum at the one or more aspiration port openings 510.

In some cases, the methods further include using the suction force generated by the Venturi-created or Venturi-assisted vacuum to capture and retain biological object such as a solid deposit 545 at the one or more aspiration openings 510.

In some cases, the methods further include ablating the biological object such a solid deposit 545 into a plurality of (smaller) particles using an ablating instrument. In some cases, the ablating instrument can be a laser, however, other ablating instruments are also contemplated herein. Non-limiting cases of suitable ablating instruments include ultrasonic instruments, electrohydraulic instruments, and pneumatic instruments. In some cases, the plurality of particles is configured to be removed from the location internal a subject via the Venturi-based vacuum at the one or more aspiration port openings.

The described examples are not intended to be limiting in any way, and the skilled artisan will understand, based upon the teachings of this specification, that any one of the devices (e.g., instruments) and/or systems, and/or methods disclosed herein may further include one or more additional cases, such as those described in detail herein. For example, in some cases, the devices (e.g., instruments) and/or systems described herein can include an evacuation tube (e.g., evacuation tube 105, 205, 305, 405, or 505) with an outer diameter of greater than or equal to 1 mm and less than or equal to 10 mm. In some cases, the outer diameter of the evacuation tube 505 can be greater than or equal to 0.5 mm, greater than or equal to 1 mm, greater than or equal to 2 mm, greater than or equal to 3 mm, greater than or equal to 4 mm, greater than or equal to 5 mm, greater than or equal to 6 mm, greater than or equal to 7 mm, greater than or equal to 8 mm, greater than or equal to 9 mm, or greater than or equal to 9.5 mm. In some cases, the outer diameter of the evacuation tube 505 can be less than or equal to 10 mm, less than or equal to 9 mm, less than or equal to 8 mm, less than or equal to 7 mm, less than or equal to 6 mm, less than or equal to 5 mm, less than or equal to 4 mm, less than or equal to 3 mm, less than or equal to 2 mm, less than or equal to 1 mm, or less than or equal to 0.5 mm. Combinations of the above-referenced ranges are possible (e.g., greater than or equal to 1 mm and less than or equal to 10 mm). Other ranges are also possible. The diameter of the evacuation tube 505 can be determined based on a variety of factors including flow rates, desired pressures for aspiration, maneuverability, efficiency, and safety for the patient. Smaller diameters can provide higher flow velocities and correspondingly lower pressures for enhanced suction/aspiration for a given flow rate through the liquid supply lumen 520 and/or nozzle. Smaller diameters can also maintain tip deflectability for endoscopes such as ureteroscopes. Larger diameters can provide larger aspiration port openings 510 to aspirate larger biological objects, increase efficiency, and reduce the duration of a procedure. Accordingly, the outer diameter can be selected by balancing several considerations.

In some cases, the devices (e.g., instruments) and/or systems described herein can include greater than or equal to two and less than or equal to six aspiration port openings (e.g., aspiration port openings 510). In some cases, the number of aspiration port openings 510 can be greater than or equal to 2, greater than or equal to 3, greater than or equal to 4, greater than or equal to 5, or greater than or equal to 6. In some cases, the number of aspiration port openings is less than or equal to 6, less than or equal to 5, less than or equal to 4, less than or equal to 3, or less than or equal to 2. The quantity of the aspiration port openings 510 can be determined based on a variety of factors including fluid recirculation, and maneuverability of the device and/or biological object. The quantity of aspiration port openings 510 can contribute to recirculation of fluid. In some embodiments, the quantity of aspiration port openings 510 can be selected to provide adequate recirculation. The quantity of aspiration port openings 510 can also provide multiple locations for attracting biological objects including debris and fragments toward the evacuation tube 505.

In some cases, the one or more aspiration port openings (e.g., one or more aspiration port openings 510) can be placed in a particular configuration along and/or around the evacuation lumen. The one or more aspiration port openings 510 may be placed in any suitable configuration on evacuation lumen known to the skilled artisan. For example, in some cases, the one or more aspiration port openings 510 may be placed in the circular configuration around the circumference of the evacuation lumen. In such cases, the circular configuration can reduce the chance of clogging the evacuation lumen and can enable rotation of the evacuation tube 505 without affecting the suction around the evacuation tube 505. Additionally or alternatively, the aspiration port openings 510 can be in a line of sight (LOS) of an endoscopic camera and/or an ablation device as described herein. In such cases, debris and/or fragments of biological objects fragmented from the biological object can remain in full view as the ablation device fragments the biological object.

In some cases, each of the one or more aspiration port openings 510 can have an average cross-sectional dimension of greater than or equal to 0.01 mm, greater than or equal to 0.025 mm, greater than or equal to 0.05 mm, greater than or equal to 0.1 mm, greater than or equal to 0.5 mm, greater than or equal to 1 mm, greater than or equal to 1.5 mm, greater than or equal to 2 mm, greater than or equal to 4 mm, or greater than or equal to 5 mm. In some cases, each of the one or more aspiration port openings 510 can have an average cross-sectional of less than or equal to 6 mm, less than or equal to 5 mm, less than or equal to 4 mm, less than or equal to 2 mm, less than or equal to 1.5 mm, less than or equal to 1 mm, less than or equal to 0.5 mm, less than or equal to 0.1 mm, or less than or equal to 0.05 mm. Combinations of the above referenced ranges are also possible (e.g., greater than or equal to 0.01 mm and less than or equal to 6 mm, greater than or equal to 0.05 mm and less than or equal to 1 mm). Other ranges are also possible. Selecting a size for the one or more aspiration port openings 510 can be determined by balancing various factors including the size of the biological objects and available suction force. Larger aspiration port openings 510 can allow larger particles and biological materials to pass through the aspiration port openings 510. Large biological objects may become stuck and risk blocking aspiration flow. Accordingly, in some embodiments, the aspiration port openings 510 can be limited in size to prevent large biological objects from entering the evacuation lumen. Additionally or alternatively, smaller aspiration port openings 510 may help create more suction force at the distal tip due to an increased velocity of the liquid through the smaller aspiration port openings 510.

The one or more aspiration port openings 510 may be of any suitable cross-sectional shape. Non-limiting examples of suitable cross-sectional shapes include triangles, squares, rectangles (e.g., having any suitable aspect ratio) circles, ovals, polygons (e.g., pentagons, hexagons, heptagons, octagons, nonagons, dodecagons, or the like), rings, irregular shapes, or the like.

In some cases, one or more aspiration port openings 610 and/or one or more vent port openings 615 can include a mesh 600. FIG. 8A shows an evacuation tube 605 having a one or more aspiration port openings 610, one or more vent port openings 615, a liquid supply lumen 620, a nozzle 625, and an evacuation lumen 635. The evacuation tube 605 can be the same or similar to any of the evacuation tubes described herein, such as the evacuation tubes 105 or 205. In some cases, the evacuation tube 605 can be positioned within an outer sheath 660.

FIG. 8B shows one of the one or more aspiration port openings 610 without a mesh 600. Accordingly, the aspiration port opening 610A can be unobstructed. Without a mesh 600, particles can freely ingress or egress through the aspiration port opening 610A. In such cases, the only limitation on the particle sizes that can be received by the aspiration port opening 610A is the outer periphery of the aspiration port opening 610A.

FIG. 8C shows one of the one or more aspiration port opening 610 having a mesh 600. Accordingly, the aspiration port opening 610B can be at least partially obstructed. With the mesh 600, particles can be prevented from freely ingressing or egressing through the aspiration port opening 610B.

FIG. 8D shows one of the one or more vent port openings 615 without a mesh 600. Accordingly, the vent port opening 615A can be unobstructed. Without a mesh 600, particles can freely ingress or egress through the vent port opening 615A. In such cases, the only limitation on the particle sizes that can be received by the vent port opening 615A is the outer periphery of the vent port opening 615A.

FIG. 8E shows one of the one or more vent port openings 615 having a mesh 600. Accordingly, the vent port opening 615B can be at least partially obstructed. With the mesh 600, particles can be prevented from freely ingressing or egressing through the vent port opening 615B.

The mesh 600 shown in FIGS. 8C and 8E can have any suitable pore size and those of ordinary skill in the art would be capable of selecting suitable pore sizes, based upon the teachings of this specification. For example, in some cases, the mesh 600 can have a U.S. Mesh Number of greater than or equal to 35, greater than or equal to 50, greater than or equal to 75, greater than or equal to 100, greater than or equal 150, greater than or equal 200, greater than or equal to 250, greater than or equal 300, or greater than or equal 350. In some cases, the mesh 600 can have a U.S. Mesh Number of less than or equal to 400, less than or equal to 350, less than or equal to 300, less than or equal to 250, less than or equal 200, less than or equal 150, less than or equal to 100, less than or equal 75, or less than or equal to 50. Combinations of the above-referenced ranges are possible (e.g., greater than or equal to 35 and less than or equal to 400). Other ranges are also possible. As would be understood by one of ordinary skill in the art, the U.S. Mesh Number (sometimes referred to as a Tyler Mesh Size) is the number of holes per linear inch of a mesh. Each hole of the mesh may have any suitable size according to the U.S. Mesh Number standard (e.g., a diameter greater than or equal to 0.037 mm and less than or equal to 0.500 mm).

In some cases, the one or more aspiration port openings 610 can be configured to selectively retain and/or exclude a biological object such as a solid deposit (e.g., a plurality of kidney stones). Selective regulation of biological objects may be done using any suitable technique known to the skilled artisan.

In some cases, the devices (e.g., instruments) and/or systems described herein include greater than or equal to two and less than or equal to six vent port openings (e.g., the one or more vent port opening 215 as shown in FIG. 4A). In some cases, the number of the one or more vent port openings 615 can be greater than or equal to 2, greater than or equal to 3, greater than or equal to 4, greater than or equal to 5, or greater than or equal to 6. In some cases, the number of the one or more vent port openings 615 can be less than or equal to 6, less than or equal to 5, less than or equal to 4, less than or equal to 3, or less than or equal to 2.

In some cases, the one or more vent port openings 615 can be placed in a particular configuration along and/or around the evacuation lumen 635. The one or more vent port openings 615 may be placed in any suitable configuration on evacuation lumen 635 known to the skilled artisan. For example, in some cases, the one or more vent port openings 615 can be placed in a linear configuration along the length of the evacuation lumen 635. In some cases, the one or more vent port openings 615 can be placed in a circular configuration around the circumference of the evacuation lumen 635.

In some cases, each of the one or more vent port openings 615 can have an average cross-sectional dimension of greater than or equal to 0.01 mm, greater than or equal to 0.025 mm, greater than or equal to 0.05 mm, greater than or equal to 0.1 mm, greater than or equal to 0.5 mm, greater than or equal to 1 mm, greater than or equal to 1.5 mm, greater than or equal to 2 mm, greater than or equal to 4 mm, or greater than or equal to 5 mm. In some cases, each of the one or more vent port openings 615 can have an average cross-sectional of less than or equal to 6 mm, less than or equal to 5 mm, less than or equal to 4 mm, less than or equal to 2 mm, less than or equal to 1.5 mm, less than or equal to 1 mm, less than or equal to 0.5 mm, less than or equal to 0.1 mm, or less than or equal to 0.05 mm. Combinations of the above referenced ranges are also possible (e.g., greater than or equal to 0.01 mm and less than or equal to 6 mm, greater than or equal to 0.05 mm and less than or equal to 1 mm). Other ranges are also possible.

The one or more vent port openings 615 may be of any suitable cross-sectional shape. Non-limiting examples of suitable cross-sectional shapes include triangles, squares, rectangles (e.g., having any suitable aspect ratio) circles, ovals, polygons (e.g., pentagons, hexagons, heptagons, octagons, nonagons, dodecagons, or the like), rings, irregular shapes, or the like.

In some cases, one or more vent port openings 615 can include a mesh 600. The mesh 600 may have any suitable pore size and those of ordinary skill in the art would be capable of selecting suitable pore sizes, based upon the teachings of this specification.

In some cases, the devices (e.g., instruments) and/or systems described herein can include an outer sheath (e.g., outer sheath 660). In some cases, a liquid-jet forming aspiration device is disposed within the outer sheath 660. Any one of the liquid-jet forming aspiration devices (e.g., instrument 200) disclosed herein may be disposed within the outer sheath 660. In some cases, the liquid jet forming aspiration device can be a liquid jet forming aspiration catheter disposed within the outer sheath 660.

In some cases, the liquid jet forming aspiration device can be movable within the outer sheath 660. In some cases, the catheter can be capable of being moved axially and rotationally within the outer sheath 660, for example, to enable adjustment of an angular orientation of a distal end of the liquid jet forming aspiration catheter and exposure of the one or more aspiration port openings 610 to an environment external to the evacuation lumen 635 (e.g., the lumen of the pelvis or calyces of the kidney) when the instrument is in operation. For example, referring again to FIG. 4A, outer sheath 260 may be movable with respect to evacuation tube 205.

In some cases, the outer sheath 660 can be associated with an auxiliary device. For example, in some cases, the outer sheath 660 can be associated with a catheter, an endoscope, a trocar, or the like.

In some cases, the outer sheath 660 can be a dual lumen sheath. In some cases, the dual lumen sheath can be a dual lumen catheter or a dual lumen scope, such as a dual lumen endoscope.

In some cases, the outer sheath 660 can have an inner diameter of greater than or equal to 1 mm and less than or equal to 10 mm. In some cases, the inner diameter of the outer sheath 660 can be greater than or equal to 0.5 mm, greater than or equal to 1 mm, greater than or equal to 2 mm, greater than or equal to 3 mm, greater than or equal to 4 mm, greater than or equal to 5 mm, greater than or equal to 6 mm, greater than or equal to 7 mm, greater than or equal to 8 mm, greater than or equal to 9 mm, or greater than or equal to 9.5 mm. In some cases, the inner diameter of the outer sheath 660 can be less than or equal to 10 mm, less than or equal to 9 mm, less than or equal to 8 mm, less than or equal to 7 mm, less than or equal to 6 mm, less than or equal to 5 mm, less than or equal to 4 mm, less than or equal to 3 mm, less than or equal to 2 mm, less than or equal to 1 mm, or less than or equal to 0.5 mm. Combinations of the above-referenced ranges are possible (e.g., greater than or equal to 1 mm and less than or equal to 10 mm). Other ranges are also possible. In some cases, the inner diameter of the outer sheath 660 can be substantially similar to the outer diameter of the evacuation tube 605. The outer sheath 660, as disclosed herein, may be of any suitable geometry. For example, in some cases, the outer sheath 660 may be shaped like a circle, triangle, square, diamond, or the like.

In some cases, a liquid-jet forming aspiration device can be configured to fit within a catheter. The catheter may be of any suitable size known to the skilled artisan. For example, in some cases, the catheter size is between 3 Fr and 20 Fr. In some cases, the catheter size is between 2 Fr and 4 Fr. In some cases, the catheter size is 3.6 Fr.

In some cases, the controller can be adapted and configured to flow a liquid through the liquid supply lumen 620 at a flow rate of greater than or equal to between 10 mL/min and 200 mL/min. in some cases, the controller can be adapted and configured to flow a liquid through the liquid supply lumen 620 at a flow rate of greater than or equal to 10 mL/min, greater than or equal to 20 mL/min, greater than or equal to 30 mL/min, greater than or equal to 40 mL/min, greater than or equal to 50 mL/min, greater than or equal to 60 mL/min, greater than or equal to 70 mL/min, greater than or equal to 80 mL/min, greater than or equal to 90 mL/min, or greater than or equal to 100 mL/min. In some cases, the controller can be adapted and configured to flow of liquid through the liquid supply lumen 620 at a flow rate of less than or equal to 100 mL/min, less than or equal to 90 mL/min, less than or equal to 80 mL/min, less than or equal to 70 mL/min, less than or equal to 60 mL/min, less than or equal to 50 mL/min, less than or equal to 40 mL/min, less than or equal to 30 mL/min, less than or equal to 20 mL/min, or less than or equal to 10 mL/min. The flow rate through the liquid supply lumen 620 can be selected by balancing various factors including resulting suction force, heat transfer, fluid management, and risk of injury to the patient. Providing an insufficient flow rate can result in generating insufficient suction to aspirate one or more biological objects and/or providing insufficient heat transfer from the ablation device to the liquid for regulating and maintaining temperatures within the system. Accordingly, the system may be unable to remove biological objects and/or may result in injury to the patient. By comparison, providing an excessively high flow rate can overpower a vacuum source such that the outlet flow rate caused by the vacuum source cannot match the flow rate of the inlet flow rate through the liquid supply lumen 620. Thus, providing an excessively high flow rate risks overexpansion of the anatomical structure receiving the system which may result in injury to the patient. Furthermore, providing an excessively high flow rate can pose risks of injury to the patient because it may be difficult to detect a discrepancy between inflow and outflow and respond to the discrepancy in a timely manner.

In some cases, the devices (e.g., instruments) and/or systems described herein include a liquid supply lumen (e.g., liquid supply lumen 620 of FIG. 8A). In some cases, the liquid supply lumen 620 can include an inlet configured to receive a liquid at a pressure of greater than or equal to 500 psi and less than or equal to 15,000 psi. In some cases, the inlet can be configured to receive a liquid at a pressure of greater than or equal to 500 psi, greater than or equal to 1000 psi, greater than or equal to 2500 psi, greater than or equal to 5000 psi, greater than or equal to 7500 psi, greater than or equal to 10,000 psi, greater than or equal to 12,500 psi, or greater than or equal to 15,000 psi. In some cases, the inlet can be configured to receive a liquid at a pressure of less than or equal to 15,000 psi, less than or equal to 12,500 psi, less than or equal to 10,000 psi, less than or equal to 7500 psi, less than or equal to 5000 psi, less than or equal to 2500 psi, less than or equal to 1000 psi, or less than or equal to 500 psi. The pressure within the liquid supply lumen 620 can be determined by balancing various factors including material strength, liquid flow rates, maneuverability, visibility, requisite suction force, and safety to the patient. A liquid flow rate is measured as a volume of liquid passing a location for a given period of time. As described herein, velocity and pressure can be inversely related. Accordingly, the size of the liquid supply lumen 620 can be inversely proportional to the pressure that can be contained within the liquid supply lumen 620 to provide a given target flow rate. For example, the higher the pressure, the smaller the liquid supply lumen 620 can be to provide the same target flow rate as a larger liquid supply lumen 620. In some cases, smaller liquid supply lumens 620 may be more flexible than larger liquid supply lumens 620. Accordingly, maneuverability of the system can be increased by implementing a smaller liquid supply lumen 620. Excessively high pressures within the liquid supply lumen 620 can cause the liquid jet to cavitate inside the evacuation tube 605 resulting in introducing bubbles into the field of view and impairing visibility. Insufficient pressure can result in a low flow rate that is ineffective to produce adequate suction.

FIGS. 9A-9F, show an instrument 700 having an evacuation tube 705 coupled to an inverter cap 706. As described herein, an evacuation tube can refer to a catheter body. For example, the evacuation tube 705 can be an outer wall of a catheter. In some cases, the inverter cap 706 can be a high-pressure fluid invertor. In some cases, the inverter cap 706 can be disposed at the distal end of the instrument 700. In some cases, the inverter cap 706 can be dome-shaped. The dome shape of the inverter cap 706 may advantageously provide a rounded and smooth end that may contact the patient's internal tissue. The rounded and smooth geometry of the inverter cap 706 may prevent injury to the patient's internal tissue from axial contact. Additionally, the inverter cap 706 can have an internal geometry to assist with redirecting the liquid jet-flow from the liquid supply lumen 720 to the evacuation lumen 735. For example, the inverter cap 706 can have an internal concave structure configured to redirect a fluid flow 180 degrees.

Figure 9A:
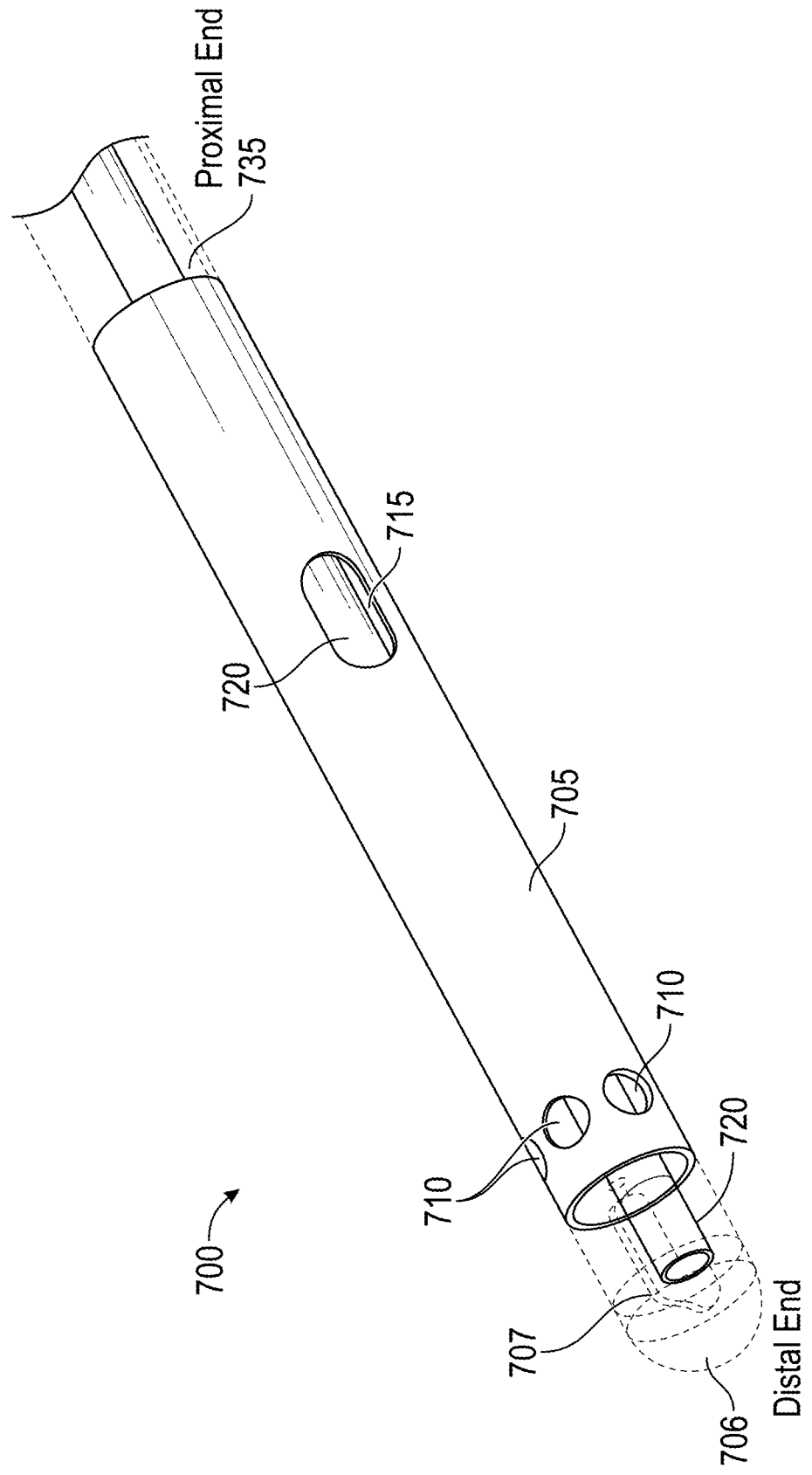
FIGS. 9A-9F show as (partially transparent to show internal detail) an illustration of a distal end of an example liquid-jet powered medical aspiration instrument with a plurality of circumferentially disposed aspiration ports, as well as several cross-sectional views of the instrument (FIGS. 9B-9D) and detailed views of an inverter plate (FIG. 9E) and an inverter cap (FIG. 9F) downstream of a high pressure liquid carrying tube and upstream of a liquid-jet-forming nozzle.

FIG. 9A shows a perspective view of a distal end of the instrument 700. The instrument 700 can be the same or similar to other instruments described herein, such as the instrument 100 or 200. For example, the instrument 700 can include an evacuation tube 705 having a plurality of aspiration port openings 710, one or more vent port openings 715, a liquid supply lumen 720, and an evacuation lumen 735. The aspiration port openings 710, the one or more vent port openings 715, the liquid supply lumen 720, and the evacuation lumen 735 can be the same or similar to the aspiration port openings, the one or more vent port openings, the liquid supply lumens, and the evacuation lumens described herein with respect to other cases. The instrument 700 can include the inverter cap 706. In some cases, the instrument 700 can further include an inverter plate 707. In some cases, the inverter plate 707 can be disposed within the evacuation lumen proximally positioned to the inverter cap 706. For example, the inverter plate 707 can be positioned between the evacuation tube 705 and the inverter cap 706. In some cases, the inverter cap 706 can be fixedly attached to the inverter plate 707. For example, the inverter cap 706 may be laser welded to the inverter plate 707. In some cases, the inverter plate 707 can be an annular structure configured to surround the liquid supply lumen 720.

Figure 9B:
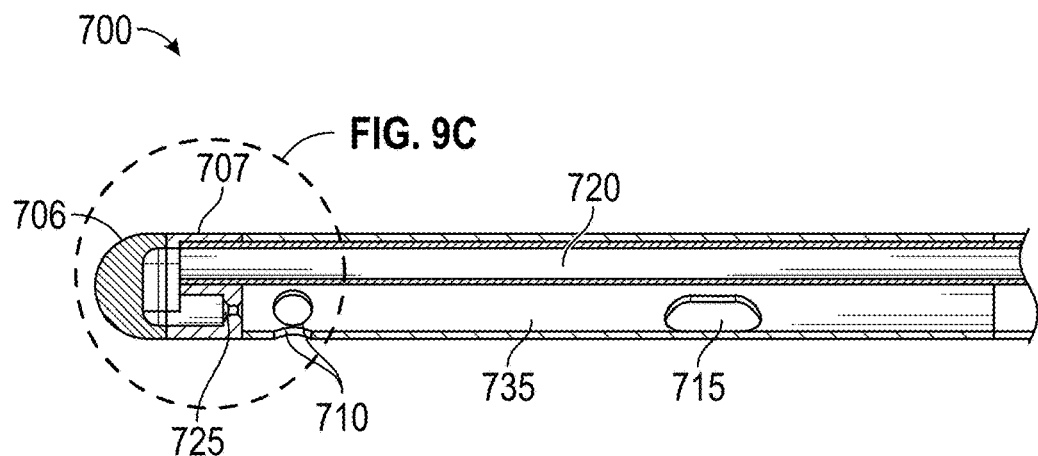
Figure 9C:
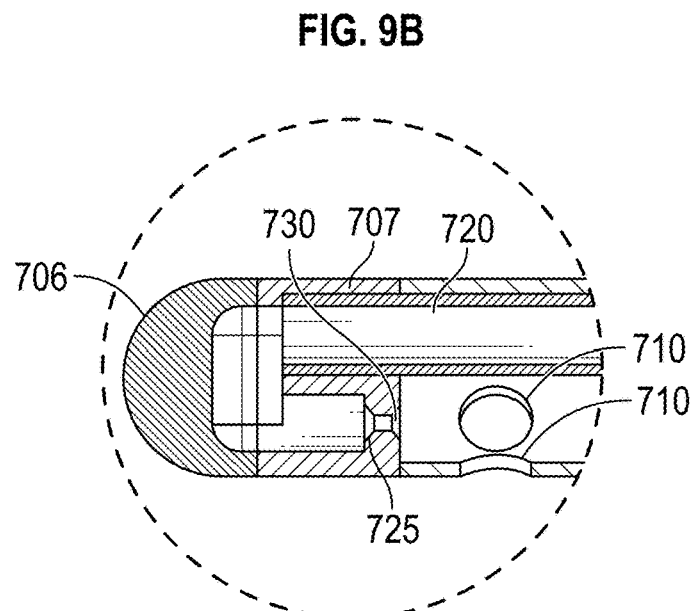
Figure 9D:
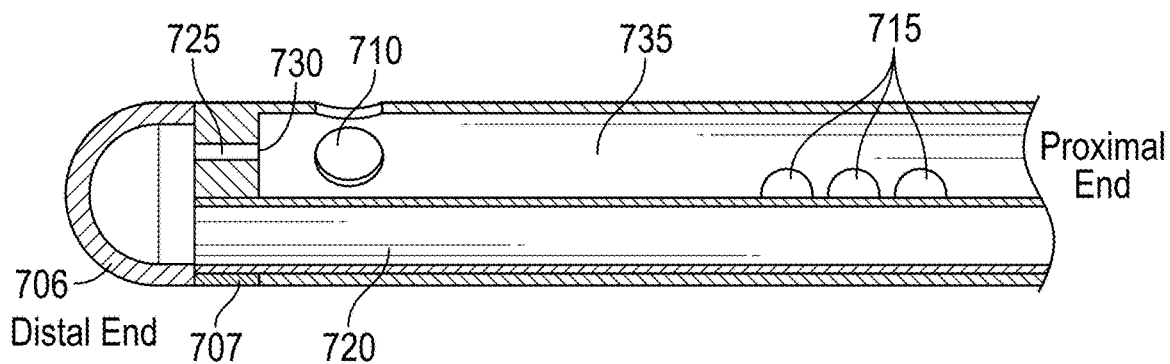

FIGS. 9B-9D show side cross-sectional views of the distal end of the instrument 700. As shown in FIG. 9B, the instrument 700 can include a nozzle 725. The nozzle 725 may include any suitable cross-sectional geometry known to the skilled artisan. Non-limiting cross-sectional geometries contemplated herein include cone geometry, bell or contoured geometry, and the annular or plug geometry.

In some cases, the nozzle 725 can include a cross-sectional dimension of greater than or equal to 50 µm or less than or equal to 200 µm. In some cases, the nozzle cross-sectional diameter can be greater than or equal to 50 µm, greater than or equal to 75 µm, greater than or equal to 100 µm, greater than or equal to 125 µm, greater than or equal to 150 µm, greater than or equal to 175 microns, or greater than or equal to 200 µm. In some cases, the nozzle cross-sectional diameter can be less than or equal to 200 µm, less than or equal to 150 µm, less than or equal to 125 µm, less than or equal to 100 µm, less than or equal to 75 µm, or less than or equal to 50 µm. In some cases, the nozzle 725 may have a cross-sectional dimension that tapers along at least a portion of the length of the nozzle 725. The size of the cross-sectional dimension of the nozzle 725 can be determined by balancing various factors including liquid flow rates, requisite suction force, and safety to the patient. As described herein, a liquid flow rate is measured as a volume of liquid passing a location for a given period of time. A larger cross-sectional dimension can provide a greater volume than a smaller cross-sectional dimension. A deficiently small cross-sectional dimension can result in inadequate liquid flow rates to create suction in a larger cross-sectional lumen such as the evacuation tube 705. By comparison, an excessively large cross-sectional dimension can require greater flow rates to generate a flow rate having adequate velocity to produce a liquid jet.

In some cases, the nozzle 725 can be configured to rotate about an axis. In some cases, the nozzle 725 is configured to rotate to any angle between +90° and −90°, relative to the axis of rotation. In some cases, rotating the nozzle 725 can change the direction of the liquid jet that is formed by passing a high-pressure fluid through the nozzle 725.

The nozzle 725 can further include an outlet 730 for directing a fluid flow from the liquid supply lumen 720 to the evacuation lumen 735. The outlet 730 may include any suitable cross-sectional shape. Non-limiting examples of suitable cross-sectional shapes include triangles, squares, rectangles (e.g., having any suitable aspect ratio) circles, ovals, polygons (e.g., pentagons, hexagons, heptagons, octagons, nonagons, dodecagons, or the like), rings, irregular shapes, or the like.

As shown in FIG. 9C, the outlet 730 can be positioned at the proximal end of a nozzle 725.

Figure 9E:
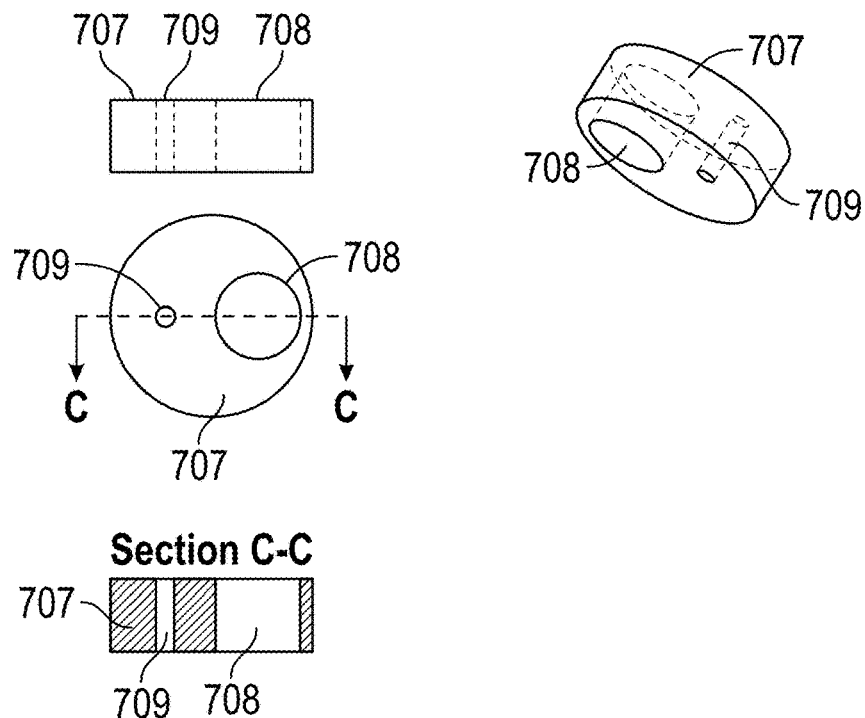

FIG. 9E shows various views of the inverter plate 707. As shown in FIG. 9E, the inverter plate 707 can have an annular structure with one or more openings extending therethrough. For example, the one or more openings can include a first opening 708 and a second opening 709. In some cases, the first opening 708 can be configured to receive and/or be part of the liquid supply lumen 720. In some cases, the second opening 709 can be configured to receive and/or be part of the nozzle 725.

Figure 9F:
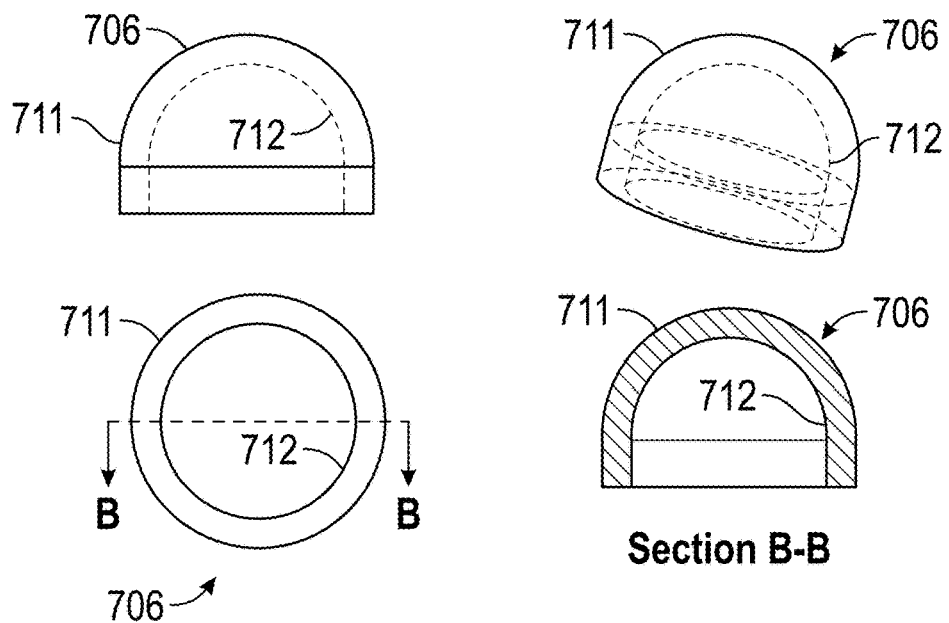

FIG. 9F shows various views of the inverter cap 706. As shown in FIG. 9F, the inverter cap 706 can have a dome-shaped body. In some cases, the inverter cap 706 can have a first surface 711 and a second surface 712. The first surface 711 can be an outer surface and the second surface 712 can be an inner surface. In some cases, the second surface 712 can be configured to redirect a fluid flow. For example, fluid from the liquid supply lumen 720 may enter the volume defined by the second surface 712 and be redirected by the dome shaped second surface 712 toward the nozzle 725.

In some cases, the instrument can include one or more feedback mechanisms. In some cases, the feedback mechanism can be configured to control one or more instrument parameters in response to a change in temperature or pressure. Other parameters may also trigger the feedback mechanism, such as for example, a change in the suction force generated by the device. In some cases, the feedback mechanism can include one or more sensors to detect the proximity of the biological object, thereby aiding in accurate targeting. In some cases, the feedback mechanism adjusts the vacuum force in real-time based on the size and nature of the biological object being captured. In some cases, the feedback mechanism regulates the operating temperature of the device to maintain the optimal temperature within the location internal to the subject.

Figure 10A:
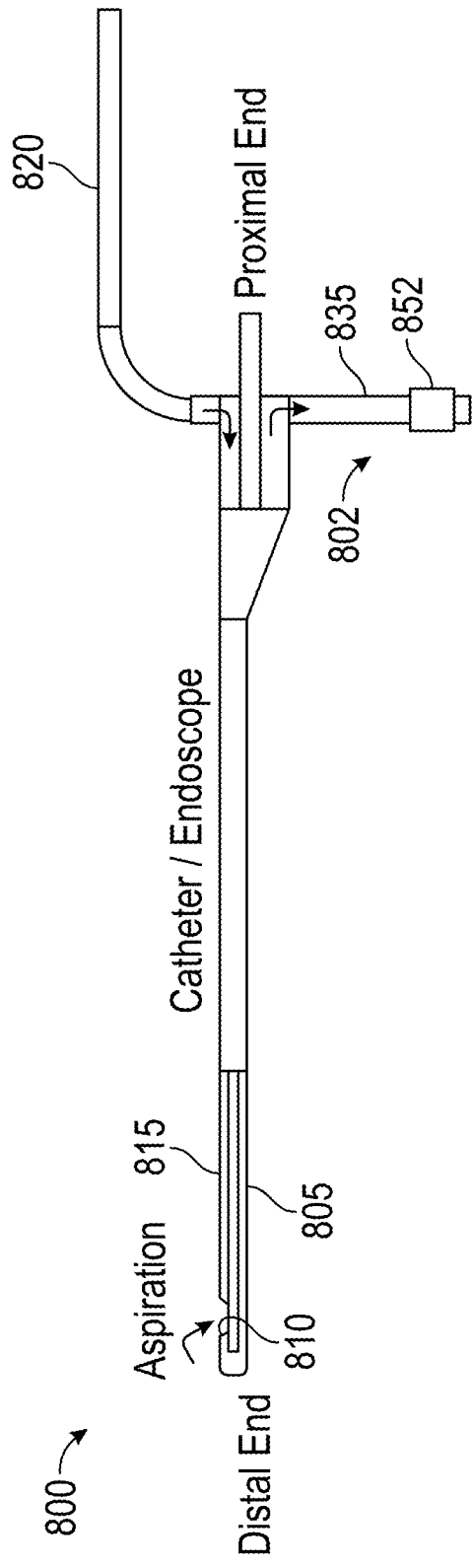
FIGS. 10A-10B are schematic diagrams of an example operation system for integrated sensing.
Figure 10B:
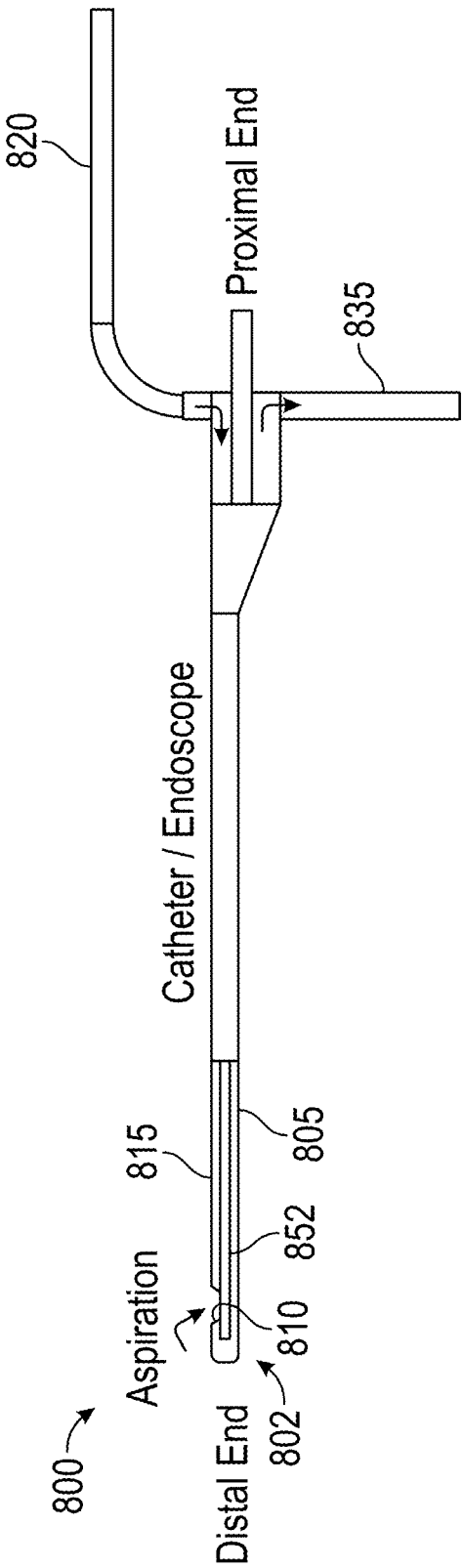

FIGS. 10A-10B, shows an instrument 800. The instrument 800 can be the same or similar to the instruments described herein, such as the instrument 100 or 200. For example, the instrument 800 can include an evacuation tube 805, one or more aspiration port openings 810, and one or more vent port openings 815. The evacuation tube 805 can be in fluid communication with a fluid supply via a first flow channel 820 and can be in fluid communication with a fluid waste channel 835. In some cases, the instrument 800 can further include an integrated sensing system 802. In some cases, the integrated sensing system 802 can include one or more sensors 852 (e.g., temperature, pressure, etc.).

FIG. 10A illustrates an example wherein the one or more sensors 852 can be positioned at a proximal side of the evacuation tube 805. For example, the one or more sensors 852 can be disposed along the fluid waste channel 835. Accordingly, the one or more sensors 852 can be configured to monitor the pressure and/or temperature of the waste fluid. Positioning the one or more sensors 852 at the proximal side of the evacuation tube 805 can result in accurate readings of the pressure within the anatomical structure (urinary tract and/or kidney (i.e., intrarenal pressure)) by intermittently starting and stopping the vacuum source. For example, the pressure at the proximal side of the evacuation tube 805 and distal to the vacuum source can have a substantially similar pressure as the pressure at the distal end of the evacuation tube 805 when the flow is paused. In some cases, positioning the one or more sensors 852 can be at a common elevation or height as the distal end of the evacuation tube 805. In some cases, positioning the one or more sensors 852 at the proximal side of the evacuation tube 805 can enable a controller to detect a formation of an obstruction or clog at the distal end of the evacuation tube 805. In some cases, positioning the one or more sensors 852 at the proximal side of the evacuation tube 805 can enable a controller to detect an imbalance in inflow and outflow from the anatomical structure.

FIG. 10B illustrates another case wherein the one or more sensors 852 can be positioned at distal side of the evacuation tube 805. In some cases, the instrument 800 can include a separate, smaller lumen e.g., to introduce and mount a pressure sensor, temperature sensor, proximity sensor, or any other sensor. In some cases, the additional lumen/channel houses the wiring, optical fibers, etc. In some cases, a signal travels through the inside or along the outside of the catheter and connects to a computer.

Figure 11:
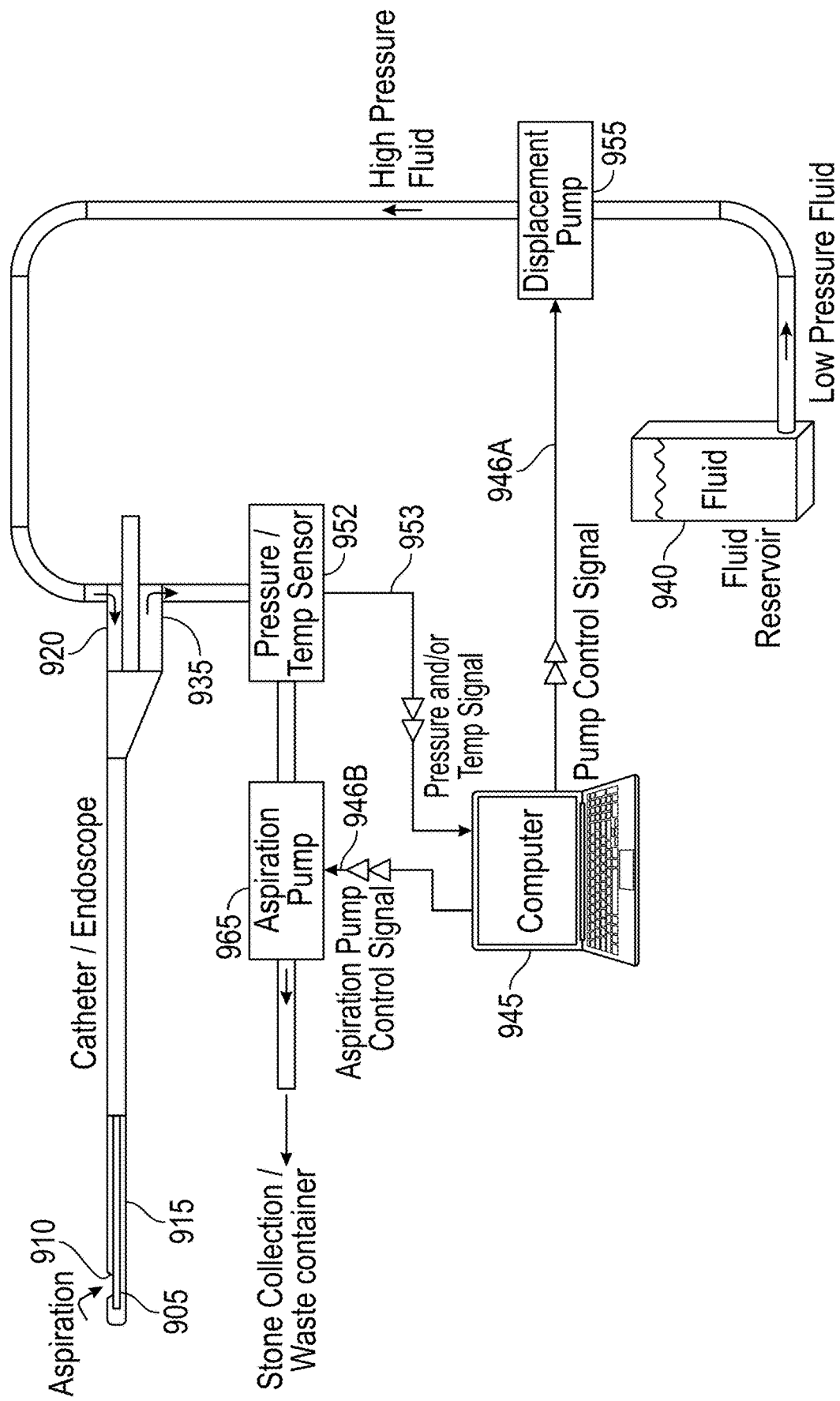
FIG. 11 is a schematic diagram of an example operation system with integrated sensing.

FIG. 11 shows a system 900 including inline pressure monitoring for monitoring pressure at an aspiration site and/or to detect occlusions in an aspiration line. The system 900 can include a controller 945 can be configured to adjust one or more pumps (e.g., inflow/outflow) to advantageously allow for optimal regulation of parameters and targeting of stones. The system 900 can be similar to the system 400 described herein. For example, the system 900 can include an evacuation tube 905, one or more aspiration port openings 910, one or more vent port openings 915, a liquid supply lumen 920, an evacuation lumen 935, a fluid source 940, a first control signal 946A, a second control signal 946B, one or more sensors 952, a feedback signal 953, a high-pressure fluidic pump 955, and a vacuum source 965. The one or more sensors 952 can be configured to monitor inline pressure at an aspiration site and/or detect occlusions in the evacuation lumen 935.

In some cases, the instrument can include an automated aspiration system and/or energy sources. In some cases, the automated aspiration system and/or energy sources can include a biological object engagement system that, upon detecting and/or capturing a biological object, subsequent procedures for manipulation and aspiration are triggered without manual intervention. In some cases, the automated aspiration system and/or energy sources are integrated with a sensing mechanism capable of detecting when the biological object is securely held by the catheter, prompting the automated advancement and manipulation of the energy source for object manipulation. In some cases, the sensing mechanism employs optical, ultrasonic, pressure, or tactile sensors to confirm the biological object's position and ensure its secure retention within the aspiration port.

Figure 12:
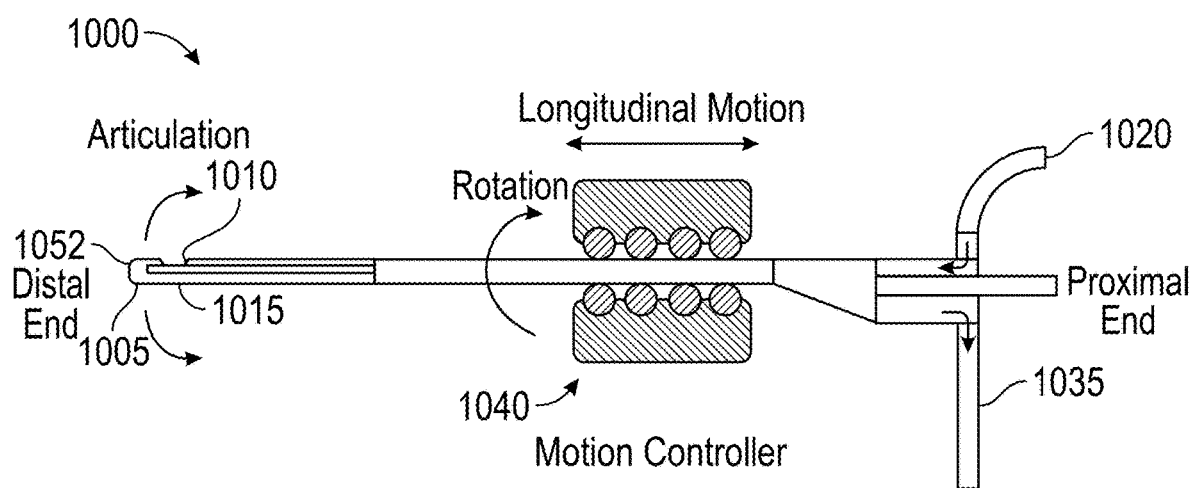
FIG. 12 is a schematic diagram of an example implementation for controlling motorized movement and automated manipulation of a solid deposit.

For example, as illustrated in FIG. 12, a system 1000 can include an instrument similar to those described herein, such as the instrument 100 or 200. For example, the system 1000 can include an evacuation tube 1005, one or more aspiration port openings 1010, one or more vent port openings 1015, a liquid supply lumen 1020, and an evacuation lumen 1035. In some cases, the system 1000 can further include an external motorized apparatus 1040. The external motorized apparatus 1040 can be configured to control one or both of the longitudinal and rotational movements of the catheter, as well as its articulation, whether it's of the catheter itself or the entire ureteroscope. In some cases, the system 1000 can be integrated with one or more sensors 1052 (e.g., built into the distal tip of the sheath, scope, catheter) or by computer vision (e.g., based on images received by a camera positioned proximal a distal tip), advantageously enabling it to determine the most effective way to manipulate stones. In some cases, the automated process involves advancing the evacuation tube 1005 intelligently towards a solid deposit such as a stone, securing the solid deposit to the evacuation tube 1005 via aspiration, retracting the solid deposit towards the ablation source, performing ablation on the solid deposit to break the solid deposit into fractured segments of debris, then suctioning the debris via aspiration into the evacuation lumen 1035, and, optionally, repeating the process as necessary. In some cases, computer vision (e.g., based on analyzing the endoscope video in real-time) can be used to determine the location of the debris relative to both the evacuation tube 1005 and an ablation source. In some cases, the motorized system senses, rotates, translates, and/or articulates as needed to find/attract a biological object such as a solid deposit, ablate, aspirate, and, optionally, repeat (e.g., thus enabling a complete closed-loop automated system).

In some cases, the automated aspiration system 1000 and/or energy sources can include one or more feedback loops that modulates the energy source's intensity and duration based on the size of the solid deposit, the composition of the solid deposit, and positioning data obtained from the sensing mechanism. In some cases, the automated aspiration system 1000 and/or energy sources can include a controller programmed to automate the sequence of capturing, manipulating, and aspirating the solid deposit, based on pre-defined criteria or real-time feedback.

In some cases, the automated aspiration system 1000 and/or energy sources can include one or more sensors 1052 that continuously monitor the manipulation process, adjusting the energy source parameters or pausing the process if the manipulation of the solid deposit is deemed complete or if potential complications are detected.

In some cases, the automated aspiration system 1000 and/or energy sources can be overridden or adjusted at any stage of the procedure, allowing for manual control when deemed necessary.

In some cases, the automated aspiration system 1000 can be configured to retrieve and process imaging and/or sensor feedback data to guide the energy source, ensuring optimal positioning and alignment for effective manipulation of the solid deposit.

In some cases, the automated aspiration system 1000 and/or energy sources can include one or more clearance mechanisms that, upon sensing successful manipulation and breaking down of the solid deposit, activates the aspiration process to remove fragments from the internal location.

In some cases, the automated aspiration system 1000 and/or energy sources can be configured with machine learning capabilities, allowing the automated aspiration system 1000 to adapt and enhance its engagement with solid deposits and manipulation procedures based on accumulated data from multiple procedures.

In some cases, the automated aspiration system 1000 can include a high-pressure fluid source connected to a nozzle that can operate in either a constant or pulsatile flow mode, as required for optimal engagement and manipulation of the solid deposit.

In some cases, the automated aspiration system 1000 can include a pump or a vacuum coupled to a proximal end of the evacuation lumen 1035 can be capable of operating with a constant or pulsatile flow, allowing for adaptability in aspiration based on the characteristics and size of the fragments or debris of the solid deposit.

In some cases, the automated aspiration system 1000 can be configured to be integrated with a controller that can switch between constant and pulsatile flow modes for both the fluid supply via the liquid supply lumen 1020 and the pump or vacuum connected at a proximal end of the evacuation lumen 1035, based on real-time feedback or pre-set procedural requirements.

In some cases, the automated aspiration system 1000 and/or energy sources can include a user interface to manually select between constant and pulsatile flow modes for fluid supply via the liquid supply lumen 1020 and evacuation via the evacuation lumen 1035, based on the specific needs of the procedure.

In some cases, the devices and/or systems described herein can include one or more clog detection and removal mechanisms. In some cases, the one or more clog detection and removal mechanisms include one or more sensors configured to detect obstructions and/or clogs at the one or more aspiration port openings 1015. In some cases, the sensors can be selected from the group consisting of pressure sensors, flow sensors, acoustic sensors, optical sensors, and combinations thereof.

In some cases, upon detection of a clog, the instrument can activate a clog removal mechanism utilizing the energy source to directly target and break down the clog at the aspiration port opening(s) 1015. In some cases, the clog removal mechanism can modulate the liquid jet dynamics, including altering jet pulse frequency, pressure, or flow rate, to dislodge the obstruction.

In some cases, the one or more clog detection and removal mechanisms can include a flexible wire or probe configured to be manually or automatically advanced through the evacuation lumen 1035 to mechanically dislodge or break apart the obstruction upon clog detection.

In some cases, the one or more clog detection and removal mechanisms can be configured to be integrated with a controller programmed to reverse or modulate the vacuum or peristaltic flow direction at the proximal end of the evacuation lumen 1035 in response to detected clogs.

In some cases, upon detection of a clog, the clog removal mechanism combines multiple strategies including energy application, jet modulation, and mechanical interventions to ensure comprehensive clog management.

In some cases, at least a portion of the devices and/or systems described herein can have a particular articulation and/or curvature (e.g., the evacuation tube 1005, the liquid supply lumen 1020, the evacuation lumen 1035, the sheath). In some cases, the devices can include an evacuation tube 1005 including a curved geometry, for example, to facilitate enhanced navigation and positioning within the location internal to the subject. In some cases, the devices and/or systems can include an articulation mechanism integrated with the evacuation tube 1005, enabling manual or automated bending or flexing of the evacuation tube 1005 to enhance retrieval or manipulation of the solid deposit. In some cases, the articulation mechanism consists of one or more joints, pivot points, or flex regions, allowing for multi-directional movement of the distal end of the instrument. In some cases, the articulation mechanism can enable precise orientation of the solid deposit relative to the energy source, optimizing the effectiveness of object manipulation or breakdown.

In some cases, the devices and/or systems can further include a control interface at the proximal end, permitting a user to adjust the articulation of the instrument in real-time during a procedure.

FIGS. 13A-13E illustrate a scope 1100. The scope 1100 can be a custom endoscope. However, any suitable scope known to the skilled artisan may be used as contemplated herein. The scope 1100 can include similar components as described herein. For example, the scope 1100 can include an evacuation tube 1105 (which can be similar to any of the evacuation tubes described herein) with one or more aspiration port openings 1110, one or more vent port openings 1115, a liquid supply lumen 1120, and an evacuation lumen 1135. The evacuation tube 1105 can be integrated into a custom ureteroscope. In some cases, the scope 1100 can further include an ablation instrument 1150. The ablation instrument 1150 can be an ablation tool configured to break apart and fragment a solid deposit 1145 into one or more smaller pieces (e.g., debris). As described herein, the ablation instrument 1150 can be a laser or laser fiber, an ultrasound ablation tool (such as, HIFU) or the like. For example, as shown in FIGS. 13A-13E, the ablation instrument 1150 may be a laser fiber. In some cases, an outer sheath can be provided with the custom scope 1100. A device disposed within an outer sheath may allow for simultaneous imaging, irrigation, manipulation of the solid deposit 1145, and aspiration during procedures, according to some cases. In some cases, integrating the devices and/or systems disclosed herein with the scope 1100 can provide synchronized control or articulating mechanisms, allowing simultaneous operation of imaging, aspiration, irrigation, and object manipulation.

Figure 13A:
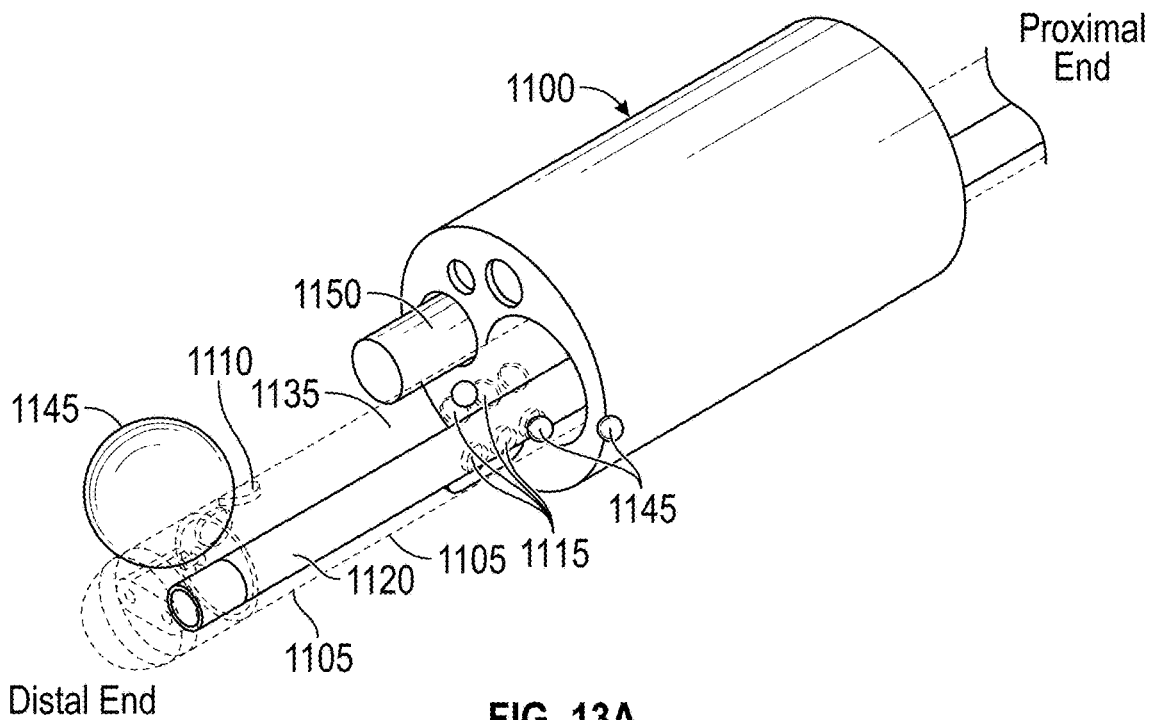
FIGS. 13A-13E are illustrations of various views of an ureteroscope including an aspiration-ablation system.

FIG. 13A shows a perspective view of the scope 1100. As shown in FIG. 13A, the evacuation tube 1105 can extend distally from the scope 1100. The evacuation tube 1105 can be configured to aspirate one or more solid deposits 1145. The one or more solid deposits 1145 can include large solid deposits that are too large to pass through the one or more aspiration port openings 1110 and/or through the evacuation lumen 1135 and small solid deposits that can pass through the one or more aspiration port openings 1110 and/or through the evacuation lumen 1135. In some cases, the one or more aspiration port openings 1110 may secure the large solid deposits 1145 in place for the ablation instrument 1150 to ablate and fracture the large solid deposit 1145 into fragments of debris. The ablation instrument 1150 can be positioned laterally offset from the longitudinal axis of the evacuation tube 1105 and aligned with the solid deposit 1145. In some cases, the ablation instrument 1150 can have diameter of about 0.7 mm.

Figure 13B:
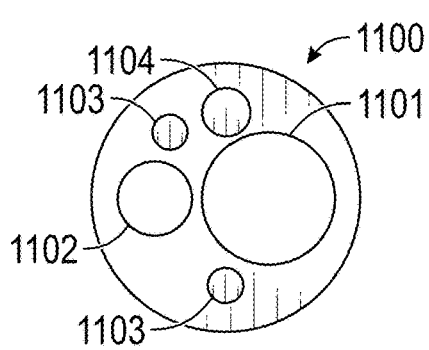

FIG. 13B shows a front view of the scope 1100. The scope 1100 can include a plurality of openings extending through the scope 1100. In some cases, the plurality of openings can include a first opening 1101 and a second opening 1102. The first opening 1101 can be sized to receive the evacuation tube 1105. For example, the dimensions of the first opening 1101 can correlate to the outer dimensions of the evacuation tube 1105. In some cases, the first opening 1101 can be sized larger than the outer dimensions of the evacuation tube 1105. For example, the diameter of the first opening 1101 can be about 1.4 mm (4.2 French). The second opening 1102 can be sized to receive the ablation instrument 1150. For example, the dimensions of the second opening 1102 can correlate to the outer dimensions of the ablation instrument 1150. In some cases, the second opening 1102 can be sized larger than the outer dimensions of the ablation instrument 1150. For example, the diameter of the second opening 1102 can be about 0.8 mm (2.4 French). The scope 1100 can further include one or more lighting elements 1103. The one or more lighting elements 1103 can be configured to provide light into the urinary system of a subject. For example, the one or more lighting elements 1103 can be light-emitting diodes (LED). In some cases, the one or more lighting elements 1103 can be distal facing and/or positioned on a distal face of the scope 1100. The scope 1100 can further include an optical element 1104. In some cases, the optical element 1104 can be configured to provide an optical view of the distal end of the scope 1100 to a physician. For example, the optical element 1104 can be a camera.

Figure 13C:
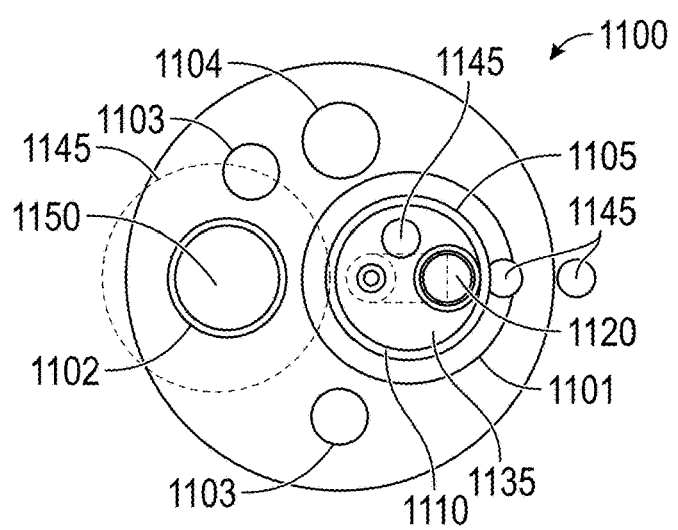

FIG. 13C shows another front view of the scope 1100 with the evacuation tube 1105, a plurality of solid deposits 1145, and the ablation instrument 1150. As shown in FIG. 13C, a solid deposit 1145 can be secured to the evacuation tube 1105 via aspiration at the one or more aspiration port openings 1110. The one or more aspiration port openings 1110 can be positioned on a side of the evacuation tube 1105 facing the ablation instrument 1150. In some cases, the longitudinal axis of the ablation instrument can be parallel to the longitudinal axis of the evacuation tube 1105. Accordingly, the ablation instrument 1150 can be configured to ablate and/or fragment the solid deposit 1145 secured to the side of the evacuation tube 1105. As shown in FIG. 13C, the first opening 1101 can be larger than the evacuation tube 1105. In some cases, the space between the first opening 1101 and the outer dimension of the evacuation tube 1105 can provide an irrigation fluid. For example, an irrigation fluid such as a saline solution can be provided into the urinary system of the subject via the space between the first opening 1101 and the evacuation tube 1105. The irrigation fluid can be used to inflate and/or expand organs of the urinary system.

Figure 13D:
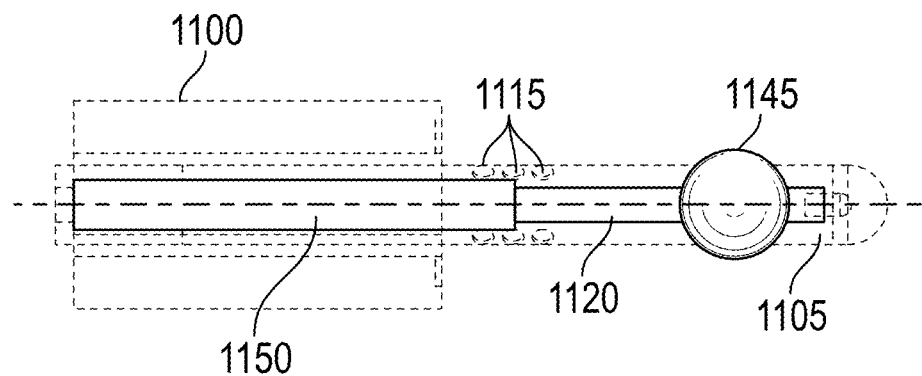

FIG. 13D shows a side elevation view of the scope 1100 with the evacuation tube 1105, a solid deposit 1145, and the ablation instrument 1150. As shown in FIG. 13D, the longitudinal axes of the evacuation tube 1105 and the ablation instrument 1150 can be co planar. The longitudinal axis of the ablation instrument 1150 can intersect the solid deposit 1145. Accordingly, the ablation instrument 1150 can emit energy along its longitudinal axis to break up and fragment the solid deposit 1145 into debris.

Figure 13E:
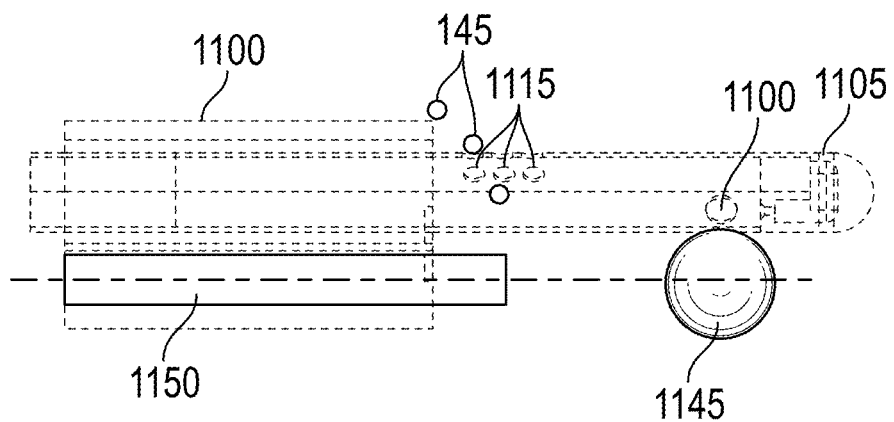

FIG. 13E shows a top view of the scope 1100 with the evacuation tube 1105, a plurality of solid deposits 1145, and the ablation instrument 1150. As shown in FIG. 13E, the longitudinal axis of the ablation instrument 1150 can intersect a solid deposit 1145 secured to the evacuation tube 1105 via the one or more aspiration port openings 1110.

Figure 14A:
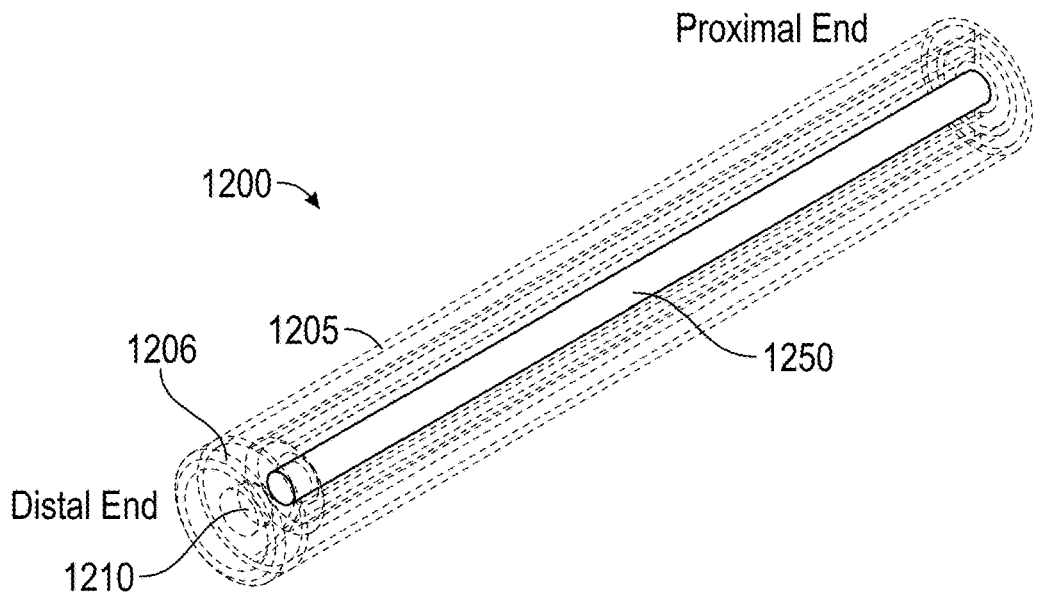
FIG. 14A-14C are illustrations of an ureteroscope having concentric lumens.
Figure 14B:
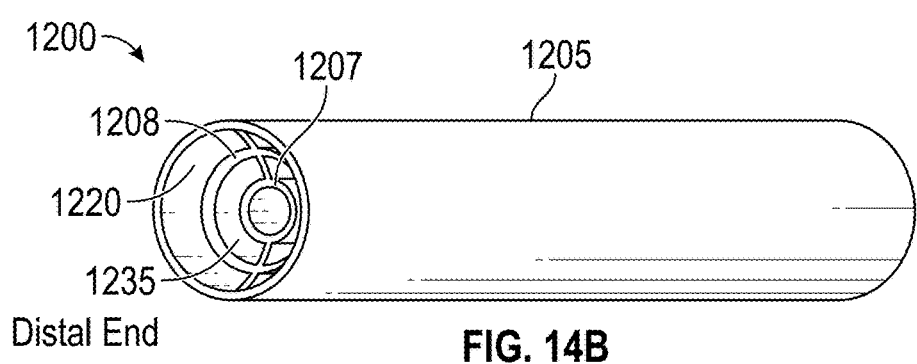
Figure 14C:
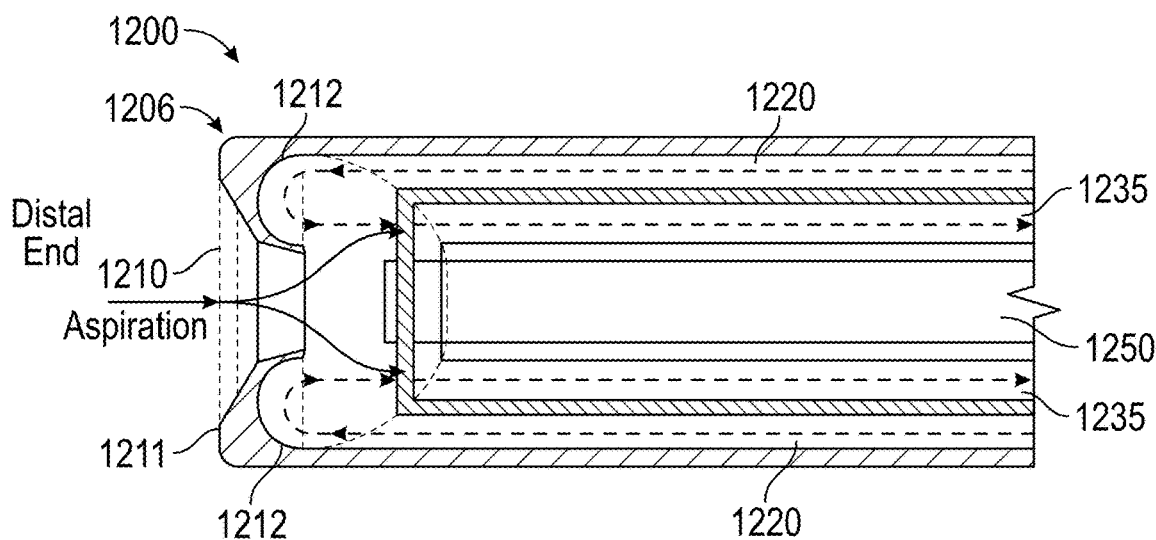

FIGS. 14A-14C illustrate an instrument 1200 having a concentric design. The instrument 1200 can be similar to any of the instruments described herein, such as the instruments 100 or 200, except for the differences described herein. In some cases, the instrument 1200 can include a concentric device design for energy delivery and aspiration at the distal end.

In some cases, the instrument 1200 can include an evacuation tube 1205 having a plurality of radially nested inner tubes. For example, the evacuation tube 1205 can include at least one inner tube. As shown in FIGS. 14A-14C, the evacuation tube 1205 can have a first inner tube 1207 and a second inner tube 1208. The first inner tube 1207 can be radially nested and disposed within the second inner tube 1208. The second inner tube 1208 can be radially nested and disposed within an outer body portion of the evacuation tube 1205. Accordingly, the evacuation tube 1205 can include a plurality of longitudinal volumes extending from a proximal end to a distal end.

As shown in FIGS. 14A-14C, the plurality of volumes can include a first interior volume, a second interior volume and a third interior volume. The first volume can be defined by the walls of the first inner tube 1207. In some cases, the first volume can be generally defined by the cross-sectional area and the length of the first inner tube 1207. For example, the first volume can be defined as: $\pi r_{1207}^2 L_{1207}$, wherein $r_{1207}$ is the radius of the first inner tube 1207 and $L_{1207}$ is the length of the first inner tube 1207. The second volume can be defined by the space between the walls of the second inner tube 1208 and the first inner tube 1207. In some cases, the second volume can be generally defined by the cross-sectional area of the second inner tube 1208, the length of the second inner tube 1208, the cross-sectional area of the first inner tube 1207, and the length of the first inner tube 1207 less any support structures. For example, the second volume can be defined as: $(\pi r_{1208}^2 L_{1208}) - (\pi r_{1207}^2 L_{1207}) - nt\Delta r L_{1208}$, wherein $r_{1208}$ is the radius of the second inner tube 1208, $L_{1208}$ is the length of the second inner tube 1208, $r_{1207}$ is the radius of the first inner tube 1207, $L_{1207}$ is the length of the first inner tube 1207, n is the number of support structures, t is the thickness of the support structures, and $\Delta r$ is the radial distance between the first inner tube 1207 and the second inner tube 1208. The third volume can be defined by the space between the walls of the outer body portion of the evacuation tube 1205 and the walls of the second inner tube 1208. In some cases, the third volume can be generally defined by the cross-sectional area of the evacuation tube 1205, the length of the evacuation tube 1204, the cross-sectional area of the second inner tube 1208, and the length of the second inner tube 1208 less any support structures. For example, the third volume can be defined as: $(\pi r_{1205}^2 L_{1205}) - (\pi r_{1208}^2 L_{1208}) - nt\Delta r L_{1205}$, wherein $r_{1205}$ is the radius of the evacuation tube 1205, $L_{1205}$ is the length of the evacuation tube 1205, $r_{1208}$ is the radius of the second inner tube 1208, $L_{1208}$ is the length of the second inner tube 1208, n is the number of support structures, t is the thickness of the support structures, and $\Delta r$ is the radial distance between the second inner tube 1208 and the evacuation tube 1205.

The plurality of longitudinal volumes can be configured to function as a liquid supply lumen, an evacuation lumen or aspiration lumen, and/or an access lumen for providing an ablation instrument 1250. For example, one of the plurality of volumes can be in fluid communication with an aspiration source such as a vacuum or aspiration pump. In some cases, the volume in fluid communication with an aspiration source can be an evacuation lumen 1235. For example, the second volume may be an evacuation lumen 1235. A different one of the plurality of volumes can be in fluid communication with a fluid source and may be configured to receive a pressurized fluid. In some cases, the volume in fluid communication with the fluid source can be a liquid supply lumen 1220. For example, the third volume may be a liquid supply lumen 1220. A different one of the plurality of volumes can be configured to receive an ablation instrument

1250. For example, the first volume may be a lumen configured to receive an ablation instrument 1250.

The instrument 1200 can further include an optional inverter cap 1206. The inverter cap 1206 can be configured to redirect a fluid flow toward the evacuation tube 1205. As described herein, the inverter cap 1206 can be configured to redirect a fluid flow 180 degrees. In some cases, the inverter cap 1206 can have an annular structure with a central lumen extending therethrough. In some implementations, a fluid supply lumen 1220 can be shaped so as to redirect the fluid flow toward the proximal end (see, for instance, FIG. 3A) without the use of the inverter cap 1206.

The central lumen can include an aspiration port opening 1210. As shown in FIGS. 14A-14C, the aspiration port opening 1210 can be positioned at a distal face of the instrument 1200. In some cases, the aspiration port opening 1210 can be a funnel shape wherein the aspiration port opening 1210 is larger on the distal side than the proximal side. The inverter cap 1206 can include a first surface 1211 and a second surface 1212 opposite the first surface 1211. In some cases, the first surface 1211 be positioned on a distal end of the inverter cap 1206 and the second surface 1212 can be on a proximal end of the inverter cap 1206. The second surface 1212 can include an annular groove extending annularly along the second surface 1212. The annular groove can be rounded. For example, the annular groove can be a semi-circle. Accordingly, a fluid entering the second surface 1212 can be redirected by the annular groove. The inverter cap 1206 can be coupled to the distal end of the evacuation tube 1205. In some cases, the annular groove can be axially displaced from the second volume and the third volume of the evacuation tube 1205. For example, the annular groove of the second surface 1212 can be axially displaced by a distance X. Accordingly, a fluid flow from one of the second or third volumes can be redirected into the other of the second or third volumes. For example, a fluid flow from the liquid supply lumen 1220 can be redirected by the annular groove of the second surface 1212 into the evacuation lumen 1235. The axial displacement can also allow external fluid and solid deposits to be aspirated through the evacuation lumen 1235.

The instrument 1200 can further include an ablation instrument 1250. In some cases, the ablation instrument 1250 can be housed within the first inner tube 1207. The ablation instrument 1250 can be an ablation tool configured to break apart and fragment a solid deposit into one or more smaller pieces (e.g., debris). As described herein, the ablation instrument 1250 can be a laser or laser fiber, an ultrasound ablation tool (such as, HIFU) or the like. For example, as shown in FIGS. 14A-14C, the ablation instrument 1250 may be a laser fiber. Accordingly, the first volume defined by the wall of the first inner tube 1207 can be filled by the ablation instrument 1250 configured to fragment a solid deposit. In some cases, the ablation instrument 1250 can emit energy through the first inner tube 1207 while the second inner tube 1208 provides aspiration thereby facilitating simultaneous energy delivery and aspiration.

In some cases, the radially nested tubes can include an outer tube and an inner tube. The outer tube can be similar to the outer body portion of the evacuation tube 1205 and the inner tube can be the same as the second inner tube 1208 described above. Accordingly, the evacuation tube 1205 can be similar to the evacuation tube 1205 described above without the first inner tube 1207. In such embodiments, the plurality of volumes can include an inner volume and an outer volume. The inner volume can be generally defined by the cross-sectional area of the inner tube and the length of the inner tube. For example, the outer volume can be defined as: $\pi r_{inner}^2 L_{inner}$, wherein $r_{inner}$ is the radius of the inner tube and $L_{inner}$ is the length of the inner tube. The outer volume can be generally defined by the cross-sectional area of the evacuation tube 1205, the length of the evacuation tube 1204, the cross-sectional area of the inner tube, and the length of the inner tube less any support structures. For example, the outer volume can be defined as: $(\pi r_{outer}^2 L_{outer}) - (\pi r_{inner}^2 L_{inner}) - n t \Delta r$, wherein $r_{outer}$ is the radius of the evacuation tube 1205, $L_{outer}$ is the length of the evacuation tube 1205, $r_{inner}$ is the radius of the inner tube, $L_{inner}$ is the length of the inner tube, n is the number of support structures, t is the thickness of the support structures, and $\Delta r$ is the radial distance between the inner tube and the evacuation tube 1205.

The effective cross-sectional areas of the volumes within the evacuation tube 1205 can be different. In some cases, the effective cross-sectional area of the volume between the evacuation tube 1205 and an inner tube can be less than the effective cross-sectional area of the inner tube. For example, the third volume described above can have an effective cross-sectional area of: $(\pi r_{1205}^2) - (\pi r_{1208}^2) - n t \Delta r$ and the second volume described above can have an effective cross-sectional area of $(\pi r_{1208}^2) - (\pi r_{1207}^2) - n t \Delta r$, wherein $r_{1205}^2 - r_{1208}^2$ is less than $r_{1208}^2 - r_{1207}^2$. Additionally or alternatively, the outer volume described above can have an effective cross-sectional area of: $(\pi r_{outer}^2) - (\pi r_{inner}^2) - n t \Delta r$ and the inner volume described above can have an effective cross-sectional area of: $(\pi r_{outer}^2) - (\pi r_{inner}^2)$, wherein $r_{outer}^2 - r_{inner}^2$ is less than $r_{inner}^2$. Accordingly, a flow rate passing from the third volume and/or outer volume into the second volume and/or inner volume passes from a constricted lumen to an expanded lumen. In such cases, a supply lumen can include a first effective cross-sectional area and an evacuation lumen and/or aspiration lumen can include a second effective cross-sectional area greater than the first effective cross-sectional area, wherein a flow of liquid can be ejected from a volume of the supply lumen with the first effective cross-sectional area into a volume of the catheter body with the second effective cross-sectional area.

In some cases, the concentric design of the instrument 1200 illustrated in FIGS. 14A-14C can be modified such that the ablation instrument 1250 can emit energy through the second inner tube 1208 and the aspiration can be facilitated through the first inner tube 1207, thereby enabling the solid deposit to be suctioned, retained, and cleared from the distal end of the evacuation tube 1205 while the ablation instrument 1250 is active. Additionally or alternatively, the concentric design of the instrument 1200 illustrated in FIGS. 14A-14C can be modified to include only two radially nested tubes including an inner tube and an outer tube as described above. In such cases, the ablation instrument may be positioned in the inner volume or the outer volume.

The concentric design of the instrument 1200 can offer multiple advantages. The concentric design of the instrument 1200 can allow for an uninterrupted energy source operation while the aspiration process captures, retains, and clears solid deposits. In some cases, clearance of fragments, debris, and dust can be enhanced by applying vacuum at the site of energy application near the aspiration port opening. For example, a high velocity flow from the liquid supply lumen into the evacuation lumen and/or aspiration lumen can be provided at the site of energy application as shown in FIGS. 14A-14C. Additionally, temperatures due to the ablation instrument 1250 may be reduced by passing the fluid flow from the liquid supply lumen into the evacuation lumen proximally to (such as, in front of) the ablation instrument 1250. The concentric design of the instrument 1200 can provide a liquid supply lumen, an evacuation lumen and/or aspiration lumen, and an ablation instrument 1250 within a single working channel of a ureteroscope. Accordingly, the concentric design of the instrument 1200 may be compatible with existing ureteroscopes having a single working channel. Coupling the discrete lumens in the concentric configuration can case manipulation of the instrument 1200 by controlling a single assembly rather than managing separate components. Furthermore, positioning the ablation instrument 1250 at the aspiration port opening can minimize clogging and the risk of obstructing the evacuation lumen since fragments and debris cannot pass around the ablation instrument 1250 until they are small enough to fit through the gap at the distal end of the instrument 1200.

Figure 15:
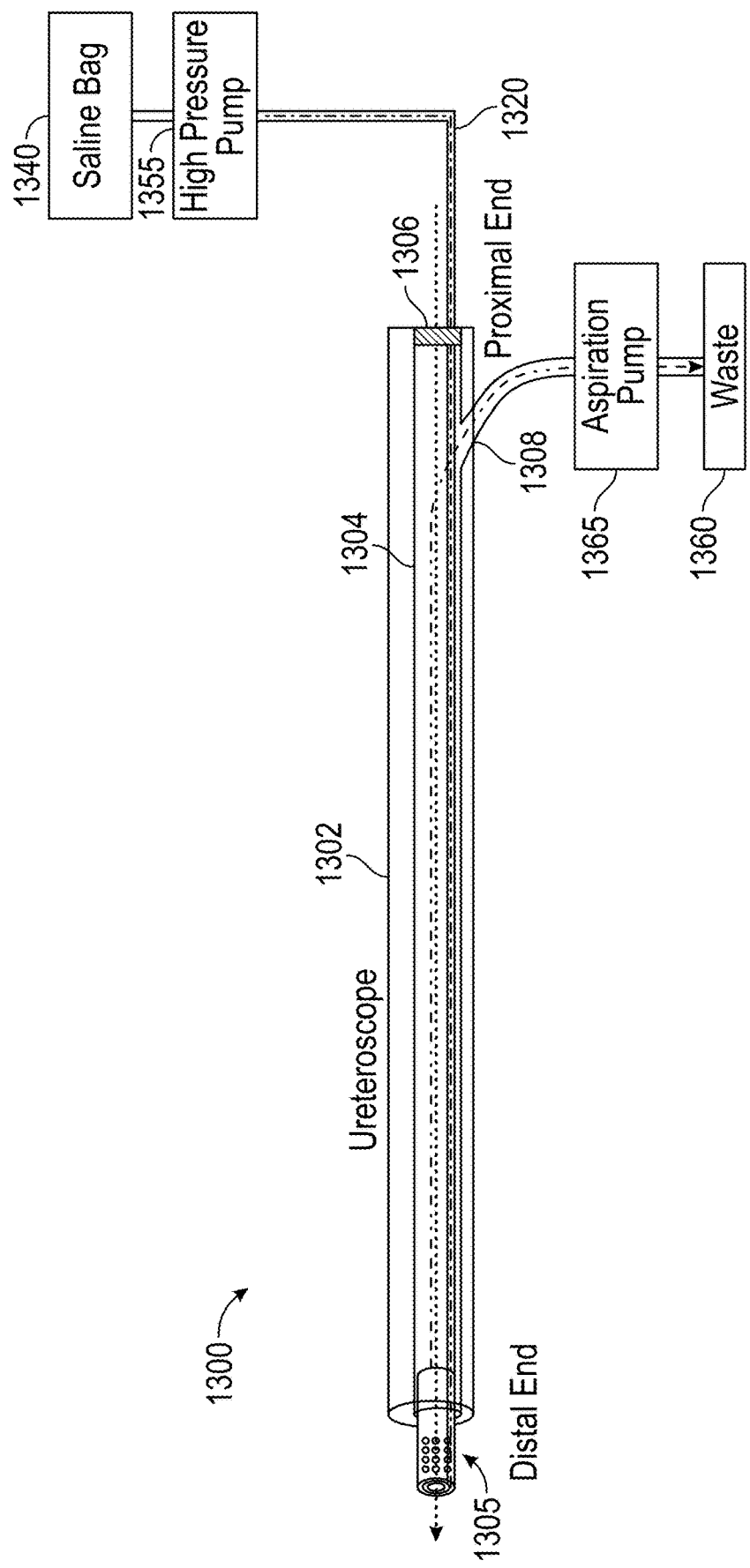
FIG. 15 is a schematic diagram of a ureteroscope system.

FIG. 15 shows a schematic of a ureteroscope system 1300, which can be similar to any of the systems described herein. While the system 1300 is described in the context of ureteroscopy, the system 1300 or any of the systems described herein can be used for any medical procedure that utilizes a catheter.

The ureteroscope system 1300 can include a ureteroscope 1302. The ureteroscope 1302 can include on or more lumens 1304. The ureteroscope 1302 can include one or more inlets 1306 and one or more outlets 1308 in fluid communication with the one or more lumens 1304. In some examples, the one or more inlets 1306 can be configured to deliver energy emitted from an ablation instrument and/or a liquid supply lumen 1320 in fluid communication with a fluid source 1340 via a high-pressure fluidic pump 1355. In some examples, the one or more inlets 1306 may be sealed to prevent egress from the one or more lumens 1304. The one or more outlets 1308 can be in fluid communication with the one or more lumens 1304. In some examples, the one or more outlets 1308 can be configured to provide an opening to evacuate from the ureteroscope 1302 waste material to a waste container 1360. The waste material can include biological objects. In some examples, the ureteroscope system 1300 can include an aspiration pump 1365 to assist with aspirating the waste material to the waste container 1360.

The ureteroscope system 1300 can further include an evacuation tube 1305. The evacuation tube 1305 can be any of the evacuation tubes described herein, such as the evacuation tube 105 or 205. For example, the evacuation tube 1305 can have a concentric design as described with regards to FIGS. 14A-14C.

The ureteroscope 1302 can be introduced to a portion of a subject's urinary system. For example, the ureteroscope 1302 can be introduced to one of the subject's kidneys. The high-pressure fluidic pump 1355 can be activated to provide a high flow rate of fluid flow through the liquid supply lumen 1320 to the distal end of the evacuation tube 1305. The evacuation tube 1305 can redirect the fluid from the liquid supply lumen 1320 toward an evacuation lumen within the one or more lumens 1304.

As described herein, the redirection of fluid can induce a Venturi effect to provide a low pressure at the distal end of the ureteroscope 1302. While aspiration pump 1365 can provide suction to the proximal end of the ureteroscope 1302, the additional suction provided by the liquid jet at the proximal end of the ureteroscope 1302 can facilitate consistent maintenance of a suction level necessary to capture a kidney stone (or more generally a biological object) at or near the distal tip of the evacuation tube 1305 and allow for efficient and safe removal the kidney stone. Energy from an ablation source can be used to fracture the kidney stone into debris that are aspirated through the one or more lumens 1304 into the waste container 1310.

Figure 16A:
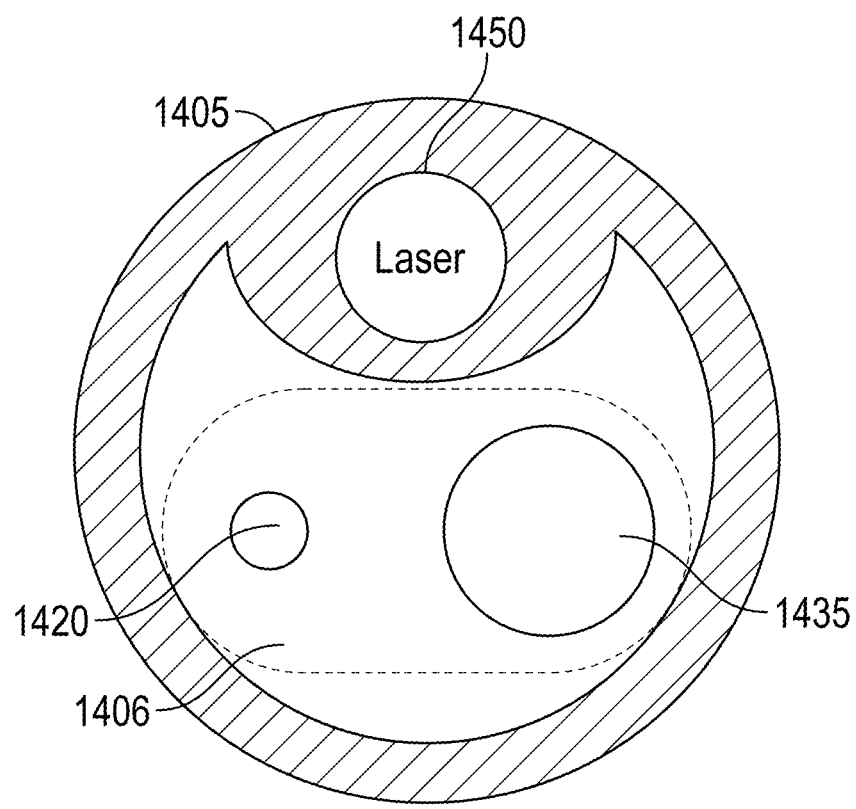
FIGS. 16A-16B are schematic diagrams of an example implementation of an evacuation tube including an aspiration-ablation system.
Figure 16B:
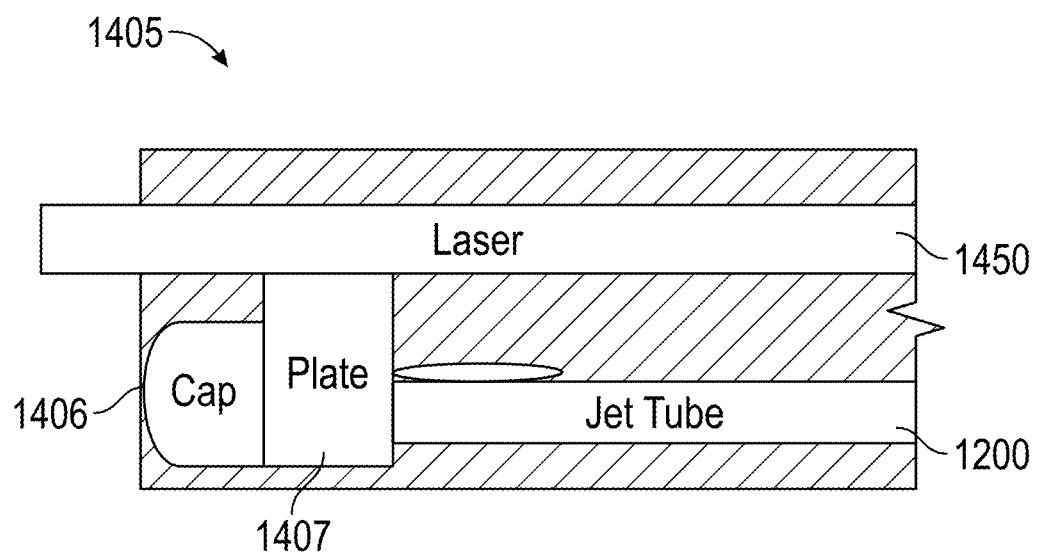

FIGS. 16A-16B illustrate an evacuation tube 1405 with an ablation instrument (e.g., a laser fiber) disposed within the evacuation tube 1405 itself. The evacuation tube 1405 can be part of a custom endoscope. The evacuation tube 1405 can be similar to any of the evacuation tubes described herein. For example, the evacuation tube 1405 can include one or more aspiration port openings, one or more vent port openings, a liquid supply lumen 1420, and an evacuation lumen 1435. In some examples, the evacuation tube 1405 can further include an ablation instrument 1450. The ablation instrument 1450 can be an ablation tool configured to break apart and fragment a solid deposit into one or more smaller pieces (e.g., debris). As described herein, the ablation instrument 1450 can be a laser or laser fiber, an ultrasound ablation tool (such as, HIFU) or the like. Integrating an ureteroscope as described herein with the evacuation tube 1405 can provide synchronized control or articulating mechanisms, allowing simultaneous operation of imaging, aspiration, irrigation, and object manipulation.

FIG. 16A shows a front view of the evacuation tube 1405. As shown in FIG. 16A, the evacuation tube 1405 can include a liquid supply lumen 1420 and an evacuation lumen 1435. The liquid supply lumen 1420 can be the same or similar to the liquid supply lumen s described herein. The evacuation lumen 1435 can be the same or similar to the evacuation lumens described herein. The evacuation tube 1405 can further include an inverter cap 1406. The inverter cap 1406 can be configured to redirect fluid flow from the liquid supply lumen 1420 toward the evacuation lumen 1435.

FIG. 16B shows a side cross-sectional view of the evacuation tube 1405. As shown in FIG. 16B, the evacuation tube 1405 can further include an inverter plate 1407. The inverter plate 1407 can have an annular structure with one or more openings extending therethrough. The one or more openings can be configured to receive and/or be part of the liquid supply lumen and/or the evacuation lumen 1435.

Accordingly, in some cases, the ablation instrument 1450 described herein (e.g., a laser) can be disposed within a portion of the evacuation tube 1405 and/or evacuation lumen 1435. In some cases, the ablation instrument 1450 may be manipulated (e.g., via a motorized apparatus) to move and/or rotate within the evacuation tube 1405. In some cases, the ablation instrument 1450 may be retracted (e.g., behind the inverter cap 1406 and/or inverter plate 1407 relative to the distal end of the evacuation tube 1405) such that a liquid may flow through an opening in which the ablation instrument 1450 was inserted. In some cases, the opening configured to receive the ablation instrument 1450 can be converted to an aspiration port opening upon retraction of the ablation instrument 1450 within the evacuation tube 1405.

Example Implementations

Examples of the implementations of the present disclosure can be described in view of the following example clauses. The features recited in the below example implementations can be combined with additional features disclosed herein. Furthermore, additional inventive combinations of features are disclosed herein, which are not specifically recited in the below example implementations, and which do not include the same features as the specific implementations below. For sake of brevity, the below example implementations do not identify every inventive aspect of this disclosure. The below example implementations are not intended to identify key features or essential features of any subject matter described herein. Any one or more features of one of the example clauses listed below can be combined by any of the one or more features of any one or more other example clauses listed below or any of the features described herein.

Clause 1. A system for use in a removal procedure of a biological object from a urinary tract, the system comprising: a catheter body comprising a proximal end and a distal end configured to be inserted into the urinary tract, the catheter body comprising one or more openings configured to receive at least a portion of the biological object; an evacuation lumen positioned at least partially within the catheter body, wherein the evacuation lumen is in fluid communication with the one or more openings; and a supply lumen positioned at least partially within the catheter body and configured to transport a liquid from a liquid source to the distal end of the catheter body, the supply lumen configured to eject the liquid as a liquid jet outside the supply lumen and create a vacuum at the one or more openings via a Venturi effect; wherein the vacuum created via the Venturi effect is configured to attract the biological object toward the one or more openings and the system is configured to remove a plurality of fragments of the biological object from the urinary tract through the evacuation lumen toward the proximal end of the catheter body with a regulated fluid flow.

Clause 2. The system of clause 1, further comprising a plurality of vent port openings formed in the catheter body and fluidically connected to the evacuation lumen, the plurality of vent port openings configured to resupply into the urinary tract at least some of the liquid ejected from the supply lumen to maintain a fluid balance and pressure balance in the urinary tract.

Clause 3. The system of any of clauses 1 to 2, wherein the supply lumen comprises a first portion that directs a flow of the liquid from the proximal end of the catheter body toward the distal end of the catheter body and a second portion that redirects the flow of the liquid toward the proximal end of the catheter body.

Clause 4. The system of any of clauses 1 to 3, further comprising a controller configured to regulate a flow rate of the liquid by the supply lumen to maintain a temperature in the urinary tract at or below a temperature threshold indicative of safe operating temperature.

Clause 5. The system of clause 4, further comprising a temperature sensor configured to monitor a temperature proximal to the catheter body, and wherein the controller is configured to regulate the flow rate of the liquid in the supply lumen based on the temperature.

Clause 6. The system of any of clauses 1 to 5, wherein the catheter body is configured to receive an ablation device configured to fragment the biological object into the plurality of fragments.

Clause 7. The system of any of clauses 1 to 6, further comprising a vacuum source in fluid communication with the evacuation lumen to regulate fluid flow through the evacuation lumen.

Clause 8. A system for use in a removal procedure of a biological object from a urinary tract, the system comprising: a catheter body comprising a proximal end and a distal end configured to be inserted into the urinary tract, the catheter body comprising one or more openings configured to receive at least a portion of the biological object; an evacuation lumen positioned at least partially within the catheter body, the evacuation lumen in fluid communication with the one or more openings, the evacuation lumen configured to be in fluid communication with a vacuum source, the vacuum source configured to supply vacuum at a first vacuum level to facilitate aspiration of a plurality of fragments of the biological object and transportation of the plurality of fragments of the biological object from the one or more openings toward the proximal end of the catheter body; and a supply lumen positioned at least partially within the catheter body and configured to transport a liquid from a liquid source to the distal end of the catheter body, the supply lumen configured to eject the liquid as a liquid jet outside the supply lumen and create a vacuum at the one or more openings at a second vacuum level via a Venturi effect to attract the biological object toward the one or more openings Clause 9. The system of clause 8, further comprising a plurality of vent port openings formed in the catheter body and fluidically connected to the evacuation lumen, the plurality of vent port openings configured to resupply into the urinary tract at least some of the liquid ejected from the supply lumen to maintain a fluid balance and pressure balance in the urinary tract.

Clause 10. The system of any of clauses 8 to 9, wherein the supply lumen comprises a first portion that directs a flow of the liquid from the proximal end of the catheter body toward the distal end of the catheter body and a second portion that redirects the flow of the liquid toward the proximal end of the catheter body.

Clause 11. The system of any of clauses 8 to 10, further comprising a controller configured to regulate a flow rate of the liquid by the supply lumen to maintain a temperature in the urinary tract at or below a temperature threshold indicative of safe operating temperature.

Clause 12. The system of clause 11, further comprising a temperature sensor configured to monitor a temperature proximal to the catheter body, and wherein the controller is configured to regulate the flow rate of the liquid in the supply lumen based on the temperature.

Clause 13. The system of any of clauses 8 to 12, wherein the catheter body is configured to receive an ablation device configured to fragment the biological object into the plurality of fragments.

Clause 14. The system of any of clauses 8 to 13, wherein the vacuum created by the Venturi effect is configured to attract the biological object toward the one or more openings.

Clause 15. The system of any of clauses 8 to 14, wherein the vacuum source is configured to regulate fluid flow in the evacuation lumen.

Clause 16. A system for use in a removal procedure of a biological object from a urinary tract, the system comprising: a catheter body comprising a proximal end and a distal end configured to be inserted into the urinary tract, the catheter body comprising an opening at a tip of the distal end of the catheter body configured to receive at least a portion of the biological object; a supply lumen positioned at least partially within the catheter body and configured to transport a liquid from the proximal end toward the distal end of the catheter body, eject the liquid, and cause a vacuum to be created at the opening to aspirate a plurality of fragments of the biological object; and an evacuation lumen positioned at least partially within the catheter body in fluid communication with the opening, wherein the evacuation lumen is configured to transport the plurality of fragments of the biological object from the distal end toward the proximal end of the catheter body, wherein the catheter body is configured to receive an ablation device configured to fragment the biological object into the plurality of fragments, and wherein the supply lumen is configured to direct liquid to flow toward the distal end of the catheter body and be redirected at the distal end to flow toward the proximal end of the catheter body.

Clause 17. The system of clause 16, wherein the evacuation lumen is configured to allow positioning of the ablation device within the evacuation lumen and downstream of the opening.

Clause 18. The system of any of clauses 16 to 17, wherein the evacuation lumen is configured to support the ablation device along a center axis of the catheter body.

Clause 19. The system of any of clauses 16 to 18, wherein the evacuation lumen comprises an ablation device tube configured to support the ablation device.

Clause 20. The system of clause 19, wherein the plurality of fragments are configured to be transported through an annular space formed between an interior surface of the catheter body and an outer surface of the ablation device tube.

Clause 21. The system of any of clauses 16 to 20, wherein the supply lumen is configured to transport the liquid from the proximal end toward the distal end of the catheter body through a first cross-sectional area of the supply lumen and eject the liquid at the distal end into a second cross-sectional area greater than the first cross-sectional area thereby causing the vacuum to be created at the opening.

Clause 22. A system for use in a removal procedure of a biological object from a urinary tract, the system comprising: a catheter body comprising a proximal end and a distal end configured to be inserted into the urinary tract, the catheter body comprising one or more openings configured to receive the biological object; an evacuation lumen positioned at least partially within the catheter body in fluid communication with the one or more openings, wherein the evacuation lumen is configured to aspirate a plurality of fragments of the biological object and transport the plurality of fragments of the biological object from the one or more openings toward the proximal end of the catheter body; a supply lumen positioned at least partially within the catheter body and configured to transport a liquid to the distal end of the catheter body, the supply lumen comprising a first portion that directs a flow of the liquid from the proximal end of the catheter body toward the distal end of the catheter body and a second portion that redirects the flow of the liquid toward the proximal end of the catheter body, wherein the second portion is configured to eject the liquid outside the supply lumen and create vacuum at the one or more openings via a Venturi effect to facilitate attracting the biological object at the one or more openings; and a plurality of vents formed in the catheter body and fluidically connected to the evacuation lumen, the plurality of vents configured to resupply into the urinary tract at least some of the liquid ejected from the supply lumen and aspirated by the evacuation lumen.

Clause 23. The system of clause 22, wherein the second portion is positioned proximal to the distal end of the catheter body.

Clause 24. The system of any of clauses 22 to 23, further comprising a controller configured to regulate a flow rate of the liquid by the supply lumen to maintain a temperature in the urinary tract at or below a temperature threshold indicative of safe operating temperature.

Clause 25. The system of clause 24, further comprising a temperature sensor configured to monitor a temperature, and wherein the controller is configured to regulate the flow rate of the liquid in the supply lumen based on the temperature.

Clause 26. The system of clause 25, wherein the catheter body is configured to receive an ablation device configured to fragment the biological object into the plurality of fragments Clause 27. The system of clause 26, further comprising a liquid source configured to supply fluid to the supply lumen.

Clause 28. The system of clause 27, further comprising a controller configured to regulate a flow rate of the liquid by the supply lumen to maintain a pressure in the urinary tract at or below a pressure threshold indicative of safe operating pressure.

Clause 29. The system of clause 28, further comprising a pressure sensor configured to monitor a pressure, and wherein the controller is configured to regulate the flow rate of the liquid in the supply lumen based on the pressure.

Clause 30. A method of removing a biological object from a urinary tract, the method comprising: creating a vacuum with a catheter positioned in the urinary tract, wherein the catheter includes a proximal end and a distal end, an evacuation lumen positioned at least partially within a catheter body of the catheter, and a supply lumen configured to transport a liquid to a distal end of the catheter, wherein the vacuum is created at one or more openings in the catheter body to attract the biological object toward the one or more openings, and wherein the vacuum is created, via a Venturi effect, by transporting the liquid through the supply lumen and ejecting the liquid as a liquid jet outside the supply lumen, optionally, through a constriction; and regulating a fluid flow in the evacuation lumen as at least a portion of the biological object enters the evacuation lumen; wherein the vacuum and regulation of the fluid flow facilitate attracting the biological object toward the one or more openings and removing the biological object from the urinary tract through the evacuation lumen and toward the proximal end of the catheter.

Clause 31. The method of clause 30, further comprising breaking the biological object attracted toward the one or more openings with an ablation device.

Clause 32. The method of clause 31, wherein the ablation device is positioned within the evacuation lumen.

Clause 33. The method of any of clauses 30 to 32, further comprising resupplying at least a portion of the liquid to the urinary tract through a plurality of vent port openings formed in the catheter body.

Clause 34. The method of clause 33, wherein the plurality of vent port openings are configured to resupply at least the portion of the liquid into the urinary tract to maintain a fluid balance and pressure balance in the urinary tract.

Clause 35. The method of any of clauses 30 to 34, wherein creating the vacuum comprises directing a flow of the liquid from the proximal end of the catheter body toward the distal end of the catheter body and redirecting the flow of the liquid proximally.

Clause 36. The method of clause 35, wherein the supply lumen directs the flow of liquid toward the distal end of the catheter body through a first cross-sectional area and redirects the flow of the liquid toward the proximal end of the catheter body at the distal end of the catheter body into a second cross-sectional area greater than the first cross-sectional area.

Clause 37. The method of any of clauses 30 to 36, wherein regulating the fluid flow comprises applying a vacuum source to the evacuation lumen at the proximal end of the catheter.

Clause 38. A method of removing a biological object from a urinary tract, the method comprising: creating a vacuum with a catheter positioned in the urinary tract, wherein the catheter includes a proximal end and a distal end, an evacuation lumen positioned at least partially within a catheter body of the catheter, and a supply lumen configured to transport a liquid to a distal end of the catheter, wherein the vacuum is created at an opening in the catheter body to attract the biological object toward the opening, and wherein the vacuum is created, via a Venturi effect, by transporting the liquid through the supply lumen and ejecting the liquid outside the supply lumen, optionally, through a constriction; aspirating at least a portion of the biological object through the opening and transporting at least the portion of the biological object along the evacuation lumen toward the proximal end of the catheter; and maintaining a fluid balance and pressure balance in the urinary tract by resupplying into the urinary tract at least some of the liquid ejected from the supply lumen.

Clause 39. The method of clause 38, wherein resupplying into the urinary tract at least some of the liquid ejected from the supply lumen is performed through a plurality of vents formed in the catheter body.

Clause 40. The method of any of clauses 38 to 39, wherein maintaining the fluid balance and pressure balance in the urinary tract comprises operating a vacuum source in fluid communication with the evacuation lumen to regulate a flow rate.

Clause 41. The method of clause 40, wherein the vacuum source is in fluid communication with the proximal end of the catheter.

Clause 42. The method of any of clauses 40 to 41, further comprising controlling the vacuum source with a controller configured to maintain a temperature in the urinary tract at or below a temperature threshold indicative of safe operating temperature.

Clause 43. The method of clause 42, wherein the controller is in electrical communication with one or more sensors.

Clause 44. The method of any of clauses 42 to 43, wherein controlling the vacuum source with a controller comprises receiving feedback from one or more sensors.

Clause 45. The method of clause 44, wherein the one or more sensors comprise one or more temperature sensors or one or more pressure sensors.

Clause 46. A method of removing a biological object from a urinary tract, the method comprising: creating a vacuum with a catheter positioned in the urinary tract, wherein the catheter includes a proximal end and a distal end, an evacuation lumen positioned at least partially within a catheter body of the catheter, and a supply lumen configured to transport a liquid to a distal end of the catheter, wherein the vacuum is created at an opening in the catheter body to attract the biological object toward the opening, and wherein the vacuum is created by transporting the liquid through the supply lumen from the proximal end to the distal end, redirecting the liquid toward the proximal end, and ejecting the liquid outside the supply lumen into the evacuation lumen; aspirating at least a portion of the biological object through the opening and transporting the biological object along the evacuation lumen toward the proximal end of the catheter; and maintaining a fluid balance and pressure balance in the urinary tract by resupplying into the urinary tract at least some of the liquid ejected from the supply lumen.

Clause 47. The method of clause 46, wherein the liquid is provided to the supply lumen as a liquid jet.

Clause 48. The method of clause 47, wherein the liquid is a first liquid and ejecting the liquid jet into the evacuation lumen induces fluid flow of a second liquid from a volume external to the catheter into the evacuation lumen.

Clause 49. The method of any of clauses 46 to 48, wherein maintaining the fluid balance and pressure balance in the urinary tract comprises operating a vacuum source in fluid communication with the evacuation lumen to regulate a flow rate.

Clause 50. The method of clause 49, wherein the vacuum source is in fluid communication with the proximal end of the catheter.

Clause 51. The method of any of clauses 49 to 50, further comprising controlling the vacuum source with a controller configured to maintain a temperature in the urinary tract at or below a temperature threshold indicative of safe operating temperature.

Clause 52. The method of clause 51, wherein the controller is in electrical communication with one or more temperature sensors.

Clause 53. The method of any of clauses 51 to 52, wherein controlling the vacuum source with a controller comprises receiving feedback from one or more temperature sensors.

Clause 54. The method of any of clauses 49 to 53, further comprising controlling the vacuum source with a controller configured to maintain a pressure in the urinary tract at or below a pressure threshold indicative of safe operating pressure.

Clause 55. The method of clause 54, wherein the controller is in electrical communication with one or more pressure sensors.

Clause 56. The method of any of clauses 54 to 55, wherein controlling the vacuum source with a controller comprises receiving feedback from one or more pressure sensors.

Clause 57. The method of any of clauses 46 to 56, wherein redirecting the liquid toward the proximal end comprises redirecting a distal flow direction in a radially outward supply lumen to a proximal flow direction in a radially inward aspiration lumen.

Clause 58. The method of clause 57, wherein the radially outward supply lumen comprises a first volume with a first cross sectional area less than the radially inward aspiration lumen comprising a second volume with a second cross sectional area.

Clause 59. The method of clause 58, wherein the catheter comprises a third volume at a proximal end of the catheter in fluid communication with an exterior volume, wherein redirecting the distal flow direction to the proximal flow direction ejects a flow of the liquid through the third volume inducing a second fluid in the exterior volume to flow in the proximal flow direction through the radially inward aspiration lumen.

Clause 60. A medical instrument, for use at a location internal to a subject, the medical instrument comprising: a liquid supply lumen configured to receive and transport a pressurized liquid to a nozzle positioned at an end of the liquid supply lumen when connected to a source of the liquid; an evacuation tube providing an evacuation lumen and comprising at least one aspiration port in the form of one or more openings in a side wall of the evacuation tube configured so that the liquid ejected from the nozzle is directed past the aspiration port to generate a venturi-created or Venturi-assisted vacuum for capturing a biological object at the location internal to the subject, when the instrument is in operation.

Clause 61. The medical instrument as in clause 60, wherein at least one vent port comprising one or more openings in the side wall of the evacuation tube positioned downstream of the at least one aspiration port and configured to eject at least a portion of the liquid flowing along the evacuation lumen.

Clause 62. A Venturi-assisted medical instrument system for use at the location internal to a subject, wherein the location is at least partially filled with a surrounding liquid, the Venturi-assisted system comprising the medical instrument of clause 60, a high-pressure fluidic pump comprising the source of the liquid, an optional vacuum source connected at a proximal end of the evacuation lumen, and a controller programmed and configured to operate the high-pressure pump system, and the optional vacuum source, when present, such that the pressure and/or volume of the location internal to the subject remains substantially constant during operation of the system.

Clause 63. The Venturi-assisted medical instrument system as in clause 62, further comprising an optional peristaltic pump connected at a proximal end of the evacuation lumen.

Clause 64. The Venturi-assisted medical instrument system as in any of clauses 60 to 63, wherein the controller is programmed and configured to operate the high pressure pump system, and the optional peristaltic pump, when present, such that the pressure and/or volume of the location internal to the subject remains substantially constant during operation of the system.

Clause 65. The Venturi-assisted medical instrument system as in any of clauses 60 to 64, wherein the optional vacuum source and the optional peristaltic pump may be operated simultaneously in parallel or in series.

Clause 66. A system for use in a removal procedure of a biological object from a urinary tract, the system comprising: a catheter body comprising a proximal end and a distal end configured to be inserted into the urinary tract, the catheter body comprising one or more openings configured to receive at least a portion of the biological object; an evacuation lumen positioned at least partially within the catheter body, the evacuation lumen in fluid communication with the one or more openings, the evacuation lumen configured to be in fluid communication with a means for regulating a fluid flow in the evacuation lumen; and a supply lumen positioned at least partially within the catheter body and configured to transport a liquid from a liquid source to the distal end of the catheter body, the supply lumen configured to eject, from a constriction in the supply lumen, the liquid as a liquid jet outside the supply lumen and create a vacuum at the one or more openings Clause 67. The system of clause 66, further comprising a plurality of vent port openings formed in the catheter body and fluidically connected to the evacuation lumen, the plurality of vent port openings configured to resupply into the urinary tract at least some of the liquid ejected from the supply lumen to maintain a fluid balance and pressure balance in the urinary tract.

Clause 68. The system of any of clauses 66 to 67, wherein the supply lumen comprises a first portion that directs a flow of the liquid from the proximal end of the catheter body toward the distal end of the catheter body and a second portion that redirects the flow of the liquid toward the proximal end of the catheter body.

Clause 69. The system of any of clauses 66 to 67, further comprising a controller configured to regulate a flow rate of the liquid by the supply lumen to maintain a temperature in the urinary tract at or below a temperature threshold indicative of safe operating temperature.

Clause 70. The system of clause 69, further comprising a temperature sensor configured to monitor a temperature proximal to the catheter body, and wherein the controller is configured to regulate the flow rate of the liquid in the supply lumen based on the temperature.

Clause 71. The system of any of clauses 66 to 70, wherein the catheter body is configured to receive an ablation device configured to fragment the biological object into a plurality of fragments.

Clause 72. The system of any of clauses 66 to 71, wherein the vacuum is configured to attract the biological object toward the one or more openings.

Clause 73. The system of any of clauses 66 to 72, wherein the means for regulating the fluid flow comprises a vacuum source.

Clause 74. A system for use in a removal procedure of a biological object from a urinary tract, the system comprising: a catheter body comprising a proximal end and a distal end configured to be inserted into the urinary tract, the catheter body comprising one or more openings configured to receive at least a portion of the biological object; an evacuation lumen positioned at least partially within the catheter body, wherein the evacuation lumen is in fluid communication with the one or more openings; and a supply lumen positioned at least partially within the catheter body and configured to transport a liquid from a liquid source to the distal end of the catheter body, the supply lumen configured to eject, from a constriction in the supply lumen, the liquid as a liquid jet outside the supply lumen and create a vacuum at the one or more openings.

Clause 75. The system of clause 74, further comprising a plurality of vent port openings formed in the catheter body and fluidically connected to the evacuation lumen, the plurality of vent port openings configured to resupply into the urinary tract at least some of the liquid ejected from the supply lumen to maintain a fluid balance and pressure balance in the urinary tract.

Clause 76. The system of any of clauses 74 to 75, wherein the supply lumen comprises a first portion that directs a flow of the liquid from the proximal end of the catheter body toward the distal end of the catheter body and a second portion that redirects the flow of the liquid toward the proximal end of the catheter body.

Clause 77. The system of any of clauses 74 to 76, further comprising a controller configured to regulate a flow rate of the liquid by the supply lumen to maintain a temperature in the urinary tract at or below a temperature threshold indicative of safe operating temperature.

Clause 78. The system of clause 77, further comprising a temperature sensor configured to monitor a temperature proximal to the catheter body, and wherein the controller is configured to regulate the flow rate of the liquid in the supply lumen based on the temperature.

Clause 79. The system of any of clauses 74 to 78, wherein the catheter body is configured to receive an ablation device configured to fragment the biological object into a plurality of fragments.

Clause 80. The system of any of clauses 74 to 79, further comprising a vacuum source in fluid communication with the evacuation lumen to regulate fluid flow through the evacuation lumen.

Clause 81. A medical instrument, for use at a location internal to a subject, the medical instrument comprising: a liquid supply lumen configured to receive and transport a pressurized liquid to a nozzle positioned at an end of the liquid supply lumen when connected to a source of the liquid; an evacuation tube providing an evacuation lumen and comprising at least one aspiration port in the form of one or more openings in a side wall of the evacuation tube configured so that the liquid ejected from the nozzle is directed past the aspiration port to generate a venturi-created or Venturi-assisted vacuum for capturing a biological object at the location internal to the subject, when the instrument is in operation.

Clause 82. The medical instrument as in clause 81, wherein at least one vent port comprising one or more openings in the side wall of the evacuation tube positioned downstream of the at least one aspiration port and configured to eject at least a portion of the liquid flowing along the evacuation lumen.

Clause 83. A Venturi-assisted medical instrument system for use at the location internal to a subject, wherein the location is at least partially filled with a surrounding liquid, the Venturi-assisted system comprising the medical instrument of any of clauses 81 to 82, a high-pressure fluidic pump comprising the source of the liquid, an optional vacuum source connected at a proximal end of the evacuation lumen, and a controller programmed and configured to operate the high-pressure pump system, and the optional vacuum source, when present, such that the pressure and/or volume of the location internal to the subject remains substantially constant during operation of the system.

Clause 84. The Venturi-assisted medical instrument system as in clause 83, further comprising an optional peristaltic pump connected at a proximal end of the evacuation lumen.

Clause 85. The Venturi-assisted medical instrument system as in any of clauses 83 to 84, wherein the controller is programmed and configured to operate the high pressure pump system, and the optional peristaltic pump, when present, such that the pressure and/or volume of the location internal to the subject remains substantially constant during operation of the system.

Clause 86. The Venturi-assisted medical instrument system as in any of clauses 83 to 85, wherein the optional vacuum source and the optional peristaltic pump may be operated simultaneously in parallel or in series.

Other Variations

While certain examples have been described in the context of ureteroscopy, the approaches described herein can be used for any medical procedure that utilizes a catheter, such as any medical procedure directed to removing a biological object from within the body. While certain examples have been described in the context of removing solid deposits, the approaches described herein can be used for removing any biological object, which may not necessarily be a solid.

The foregoing description details certain examples of the systems, devices, and methods disclosed herein. It will be appreciated, however, that no matter how detailed the foregoing appears in text, the systems, devices, and methods can be practiced in many ways. It should be noted that the use of particular terminology when describing certain features or aspects of the disclosure should not be taken to imply that the terminology is being re-defined herein to be restricted to including any specific characteristics of the features or aspects of the technology with which that terminology is associated.

It will be appreciated by those skilled in the art that various modifications and changes may be made without departing from the scope of the described technology. Such modifications and changes are intended to fall within the scope of the examples. It will also be appreciated by those of skill in the art that parts included in one example are interchangeable with other examples; one or more parts from a depicted example can be included with other depicted examples in any combination. For example, any of the various components described herein and/or depicted in the Figures may be combined, interchanged or excluded from other examples.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

Conditional language used herein, such as, among others, "can," "could", "might," "may," "e.g.," and the like, unless specifically stated otherwise, or otherwise understood within the context as used, is generally intended to convey that certain implementation include, while other implementations do not include, certain features, elements and/or states. Thus, such conditional language is not generally intended to imply that features, elements and/or states are in any way required for one or more implementations or that one or more implementations necessarily include logic for deciding, with or without author input or prompting, whether these features, elements and/or states are included or are to be performed in any particular implementation. The term "each," as used herein, in addition to having its ordinary meaning, can mean any subset of a set of elements to which the term "each" is applied.

It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to examples containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

All references cited herein are incorporated herein by reference in their entirety. To the extent publications and patents or patent applications incorporated by reference contradict the disclosure contained in the specification, the specification is intended to supersede and/or take precedence over any such contradictory material.

The term "comprising" as used herein is synonymous with "including," "containing," or "characterized by," and is inclusive or open-ended and does not exclude additional, unrecited elements or method steps.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, or within less than 0.01% of the stated value.

It is noted that some examples above may be described as a process, which is depicted as a flowchart, a flow diagram, a structure diagram, or a block diagram. Although a flowchart may describe the operations as a sequential process, many of the operations can be performed in parallel, or concurrently, and the process can be repeated. In addition, the order of the operations may be rearranged. A process is terminated when its operations are completed. A process may correspond to a method, a function, a procedure, a subroutine, a subprogram, etc. When a process corresponds to a software function, its termination corresponds to a return of the function to the calling function or the main function.

Various components illustrated in the figures or described herein may be implemented as software and/or firmware on a processor, controller, ASIC, FPGA, and/or dedicated hardware. The software or firmware can include instructions stored in a non-transitory computer-readable memory. The instructions can be executed by a processor, controller, ASIC, FPGA, or dedicated hardware. Hardware components, such as controllers, processors, ASICs, FPGAs, and the like, can include logic circuitry. Furthermore, the features and attributes of the specific examples disclosed above may be combined in different ways to form additional implementations, all of which fall within the scope of the present disclosure.

The above description discloses several methods and materials of the present disclosure. This disclosure is susceptible to modifications in the methods and materials, as well as alterations in the fabrication methods and equipment. Such modifications will become apparent to those skilled in the art from a consideration of this disclosure or practice of the examples disclosed herein. Consequently, it is not intended that this disclosure be limited to the specific examples disclosed herein, but that it covers all modifications and alternatives coming within the true scope and spirit of the disclosure as embodied in the attached claims.

What is claimed is:

1. A system for use in a removal procedure of a biological object from a urinary tract, the system comprising:
    a catheter body comprising a proximal end and a distal end configured to be inserted into the urinary tract, the catheter body comprising one or more openings at least partially facing an axial direction of the catheter body, wherein the one or more openings are configured to receive at least a portion of the biological object;
    an evacuation lumen positioned at least partially within the catheter body, wherein the evacuation lumen is in fluid communication with the one or more openings and wherein the evacuation lumen is configured to receive an ablation device; and
    a supply lumen positioned entirely within the catheter body and configured to transport a liquid from a liquid source to the distal end of the catheter body, the supply lumen configured to eject the liquid as a liquid jet outside the supply lumen and create a vacuum at the one or more openings via a Venturi effect,
    wherein the vacuum created via the Venturi effect is configured to attract the biological object toward the one or more openings and the system is configured to remove a plurality of fragments of the biological object from the urinary tract through the evacuation lumen toward the proximal end of the catheter body with a regulated fluid flow.

2. The system of claim 1, further comprising a plurality of vent port openings formed in the catheter body and fluidically connected to the evacuation lumen, the plurality of vent port openings configured to resupply into the urinary tract at least some of the liquid ejected from the supply lumen to maintain a fluid balance and pressure balance in the urinary tract.

3. The system of claim 1, wherein the supply lumen comprises a first portion that directs a flow of the liquid from the proximal end of the catheter body toward the distal end of the catheter body and a second portion that redirects the flow of the liquid toward the proximal end of the catheter body.

4. The system of claim 1, further comprising a controller configured to regulate a flow rate of the liquid by the supply lumen to maintain a temperature in the urinary tract at or below a temperature threshold indicative of safe operating temperature.

5. The system of claim 4, further comprising a temperature sensor configured to monitor a temperature proximal to the catheter body, and wherein the controller is configured to regulate the flow rate of the liquid in the supply lumen based on the temperature.

6. The system of claim 1, further comprising a vacuum source in fluid communication with the evacuation lumen to regulate fluid flow through the evacuation lumen.

7. A system for use in a removal procedure of a biological object from a urinary tract, the system comprising:
    a catheter body comprising a proximal end and a distal end configured to be inserted into the urinary tract, the catheter body comprising one or more openings at least partially facing an axial direction of the catheter body, wherein the one or more openings are configured to receive at least a portion of the biological object;
    an evacuation lumen positioned at least partially within the catheter body, the evacuation lumen in fluid communication with the one or more openings, wherein the evacuation lumen is configured to receive an ablation device and further configured to be in fluid communication with a vacuum source, the vacuum source configured to supply vacuum at a first vacuum level to the evacuation lumen to facilitate aspiration of a plurality of fragments of the biological object and transportation of the plurality of fragments of the biological object from the one or more openings toward the proximal end of the catheter body; and
  a supply lumen positioned entirely within the catheter body and configured to transport a liquid from a liquid source to the distal end of the catheter body, the supply lumen configured to eject the liquid as a liquid jet outside the supply lumen and create a vacuum at the one or more openings at a second vacuum level via a Venturi effect to attract the biological object toward the one or more openings.

8. The system of claim 7, further comprising a plurality of vent port openings formed in the catheter body and fluidically connected to the evacuation lumen, the plurality of vent port openings configured to resupply into the urinary tract at least some of the liquid ejected from the supply lumen to maintain a fluid balance and pressure balance in the urinary tract.

9. The system of claim 7, wherein the supply lumen comprises a first portion that directs a flow of the liquid from the proximal end of the catheter body toward the distal end of the catheter body and a second portion that redirects the flow of the liquid toward the proximal end of the catheter body.

10. The system of claim 7, further comprising a controller configured to regulate a flow rate of the liquid by the supply lumen to maintain a temperature in the urinary tract at or below a temperature threshold indicative of safe operating temperature.

11. The system of claim 10, further comprising a temperature sensor configured to monitor a temperature proximal to the catheter body, and wherein the controller is configured to regulate the flow rate of the liquid in the supply lumen based on the temperature.

12. The system of claim 7, wherein the vacuum created by the Venturi effect is configured to attract the biological object toward the one or more openings.

13. The system of claim 7, wherein the vacuum source is configured to regulate fluid flow in the evacuation lumen.

14. A system for use in a removal procedure of a biological object from a urinary tract, the system comprising:
  a catheter body comprising a proximal end and a distal end configured to be inserted into the urinary tract, the catheter body comprising an opening at a tip of the distal end of the catheter body at least partially facing an axial direction of the catheter body, wherein the opening is configured to receive at least a portion of the biological object;
  a supply lumen positioned entirely within the catheter body and configured to transport a liquid from the proximal end toward the distal end of the catheter body, eject the liquid, and cause a vacuum to be created at the opening to aspirate a plurality of fragments of the biological object; and
  an evacuation lumen positioned at least partially within the catheter body in fluid communication with the opening, wherein the evacuation lumen is configured to transport the plurality of fragments of the biological object from the distal end toward the proximal end of the catheter body,
  wherein the evacuation lumen is configured to receive an ablation device configured to fragment the biological object into the plurality of fragments, and
  wherein the supply lumen is configured to direct liquid to flow toward the distal end of the catheter body and be redirected at the distal end to flow toward the proximal end of the catheter body.

15. The system of claim 14, wherein the evacuation lumen is configured to allow positioning of the ablation device within the evacuation lumen and downstream of the opening.

16. The system of claim 14, wherein the evacuation lumen is configured to support the ablation device along a center axis of the catheter body.

17. The system of claim 14, wherein the evacuation lumen comprises an ablation device tube configured to support the ablation device.

18. The system of claim 17, wherein the plurality of fragments are configured to be transported through an annular space formed between an interior surface of the catheter body and an outer surface of the ablation device tube.

19. The system of claim 14, wherein the supply lumen is configured to transport the liquid from the proximal end toward the distal end of the catheter body through a first cross-sectional area of the supply lumen and eject the liquid at the distal end into a second cross-sectional area greater than the first cross-sectional area thereby causing the vacuum to be created at the opening.

20. A system for use in a removal procedure of a biological object from a urinary tract, the system comprising:
  a catheter body comprising a proximal end and a distal end configured to be inserted into the urinary tract, the catheter body comprising one or more openings at least partially facing an axial direction of the catheter body, wherein the one or more openings are configured to receive the biological object;
  an evacuation lumen positioned at least partially within the catheter body in fluid communication with the one or more openings, wherein the evacuation lumen is configured to aspirate a plurality of fragments of the biological object and transport the plurality of fragments of the biological object from the one or more openings toward the proximal end of the catheter body;
  a supply lumen positioned entirely within the catheter body and configured to transport a liquid to the distal end of the catheter body, the supply lumen comprising a first portion that directs a flow of the liquid from the proximal end of the catheter body toward the distal end of the catheter body and a second portion that redirects the flow of the liquid toward the proximal end of the catheter body, wherein the second portion is configured to eject the liquid outside the supply lumen and create vacuum at the one or more openings via a Venturi effect to facilitate attracting the biological object at the one or more openings; and
  a plurality of vents formed in the catheter body and fluidically connected to the evacuation lumen, the plurality of vents configured to resupply into the urinary tract at least some of the liquid ejected from the supply lumen and aspirated by the evacuation lumen.

21. The system of claim 20, wherein the second portion is positioned proximal to the distal end of the catheter body.

22. The system of claim 20, further comprising a controller configured to regulate a flow rate of the liquid by the supply lumen to maintain a temperature in the urinary tract at or below a temperature threshold indicative of safe operating temperature.

23. The system of claim 22, further comprising a temperature sensor configured to monitor a temperature, and wherein the controller is configured to regulate the flow rate of the liquid in the supply lumen based on the temperature.

24. The system of claim 23, wherein the evacuation lumen is configured to receive an ablation device configured to fragment the biological object into the plurality of fragments.

25. The system of claim 24, further comprising a liquid source configured to supply fluid to the supply lumen.

26. The system of claim 25, further comprising a controller configured to regulate a flow rate of the liquid by the supply lumen to maintain a pressure in the urinary tract at or below a pressure threshold indicative of safe operating pressure.

27. The system of claim 26, further comprising a pressure sensor configured to monitor a pressure, and wherein the controller is configured to regulate the flow rate of the liquid in the supply lumen based on the pressure.

* * * * *

UNITED STATES PATENT AND TRADEMARK OFFICE
CERTIFICATE OF CORRECTION

| | | |
|---|---|---|
| PATENT NO. | : 12,419,656 B2 | Page 1 of 1 |
| APPLICATION NO. | : 18/933999 | |
| DATED | : September 23, 2025 | |
| INVENTOR(S) | : Surag Mantri | |

It is certified that error appears in the above-identified patent and that said Letters Patent is hereby corrected as shown below:

In the Specification

In Column 8, Line 20, delete "car" and insert --ear--.

In Column 10, Lines 16-17, delete "pyclolymphatic" and insert --pyelolymphatic--.

In Column 47, Line 8, delete "case" and insert --ease--.

Signed and Sealed this
Eleventh Day of November, 2025

John A. Squires
*Director of the United States Patent and Trademark Office*